(12) United States Patent
Epple et al.

(10) Patent No.: US 7,034,147 B2
(45) Date of Patent: Apr. 25, 2006

(54) NUCLEOSIDE ANALOG LIBRARIES

(75) Inventors: Robert Epple, San Diego, CA (US); William Greenberg, San Diego, CA (US); Romas Kudirka, La Crescenta, CA (US)

(73) Assignee: IRM LLC, Hamilton (BM)

( * ) Notice: Subject to any disclaimer, the term of this patent is extended or adjusted under 35 U.S.C. 154(b) by 353 days.

(21) Appl. No.: 10/379,607

(22) Filed: May 8, 2003

(65) Prior Publication Data

US 2003/0225205 A1 Dec. 4, 2003

Related U.S. Application Data

(63) Continuation-in-part of application No. 10/306,253, filed on Nov. 27, 2002, now abandoned.
(60) Provisional application No. 60/335,229, filed on Nov. 29, 2001.

(51) Int. Cl.
 *C07H 21/00* (2006.01)
(52) U.S. Cl. .......................................... 536/25.3; 435/6
(58) Field of Classification Search ................ 536/25.3; 435/6
See application file for complete search history.

(56) References Cited

U.S. PATENT DOCUMENTS

| 5,869,696 A | 2/1999 | Reddy et al. |
| 6,372,885 B1 | 4/2002 | Johnson et al. |
| 6,417,195 B1 | 7/2002 | Lebl |

OTHER PUBLICATIONS

U.S. Appl. No. 10/379,607, filed Feb. 2003, Epple et al.*
Gough, G. R. et al.; "2'(3')–0–Benzoyluridine 5' Linked to Glass: An All Purpose Support for Solid Phase Synthesis of Oligodeoxyribonucleotides"; *Tetrahedron Letters*: 1983; pp. 5321–5324; vol. 24, No. 48; Great Britain.
Rosemeyer, Helmut and Frank Seela; "Polymer–Linked 6–Azauridine 5'–Monophosphate, a Resin of High Bioaffinity to Orotidine–5'–phosphate Decarboxylase"; *J. Med. Chem.*; 1979; pp. 1545–1547; vol. 22, No. 12.

* cited by examiner

*Primary Examiner*—James O. Wilson
*Assistant Examiner*—Howard V. Owens
(74) *Attorney, Agent, or Firm*—Townsend and Townsend and Crew LLP

(57) ABSTRACT

The present invention provides combinatorial libraries of nucleoside analog compounds and methods of making the libraries. In addition, the present invention provides methods of assaying the libraries for agonists or antagonists of a broad array of targets of therapeutic importance.

18 Claims, 39 Drawing Sheets

Puromycin
Protein synthesis inhibitor

Tunicamycin
Glycosyltransferase inhibitor

Sinefungin
Methyltransferase inhibitor

Pentostatin
anticancer agent

AZT
antiviral agent

CHA
adenosine kinase inhibitor

NUCLEOSIDE ANALOG LIBRARIES

CROSS-REFERENCES TO RELATED APPLICATIONS

This application is a CIP of Ser. No. 10/306,253 filed Nov. 27, 2002 now abandoned, which claims priority to U.S. Provisional Patent Application No. 60/335,229 filed Nov. 29, 2001, the teachings of which are incorporated herein by reference in their entirety for all purposes.

FIELD OF THE INVENTION

This invention pertains to the field of nucleoside analog libraries. The present invention also pertains to the field synthesis of nucleoside analog libraries and assaying the libraries for therapeutically useful compounds.

BACKGROUND OF THE INVENTION

It is estimated that nucleosides interact with roughly one third of the protein classes in the human genome, including polymerases, kinases, reductases, motor proteins, and structural proteins (Venter et al., *Science* 291: 1304–1351 (2001)). In addition, nucleosides play a central role in cell metabolism (FIG. 1).

The binding motifs of these nucleosides are associated with a broad array of targets of therapeutic importance in biological systems. The introduction of diverse moieties into the carbohydrate and/or the base subunits of nucleosides is a promising strategy for the identification of specific receptor ligands, enzyme inhibitors and nucleoside function modifiers. Naturally occurring nucleoside analogs demonstrate selective activities such as protein synthesis inhibition (puromycin), glycosyl transferase inhibition (tunicamycin) and methyltransferase inhibition (sinefungin) (FIG. 2). Synthetic nucleoside analogs are known to be therapeutically useful as antipsychotics, cardiotonics, diuretics, analgesic, anti-inflammatory agents, anticonvulsants, antihypertensives, antibiotics, antivirals, and anticancer agents (FIG. 3). Many of these nucleoside analogs are either on the market or in advanced clinical stages.

The increasing resistance of pathogens, the often severe side effects of nucleosides in chemotherapy and the lack of selective ligands for adenosine receptor subclasses despite extensive medicinal chemistry research emphasizes the need for nucleoside analogs in high number and diversity. The availability of high throughput screening capabilities together with the combinatorial synthesis of small organic molecule libraries offers a unique opportunity to accelerate the discovery of novel pharmaceutical targets and leads, especially with biologically privileged scaffolds like nucleosides in hand.

It is known that extracellular purines (e.g. adenosine, ADP and ATP) and pyrimidines (e.g. UDP and UTP) mediate diverse biological effects via cell-surface receptors termed purine receptors. Their complex and multifunctional role in modulating cellular and tissue function can be conceptualized as a purinergic cascade. Agonists of purine receptors with increased stability and selectivity may be achieved by synthesizing analogs of natural nucleosides. Analogs can be produced by modifications to the nitrogenous base rings and the 5' position of the nucleoside moiety.

Thus, there is a need in the art for efficient and rapid methods for synthesizing nucleoside analogs. While solid phase oligonucleotide synthesis is well established, there remains a need for more efficient methods for solid phase synthesis of nucleoside analogs. The present invention fulfills these and other needs.

SUMMARY OF THE INVENTION

The present invention provides novel libraries of nucleoside analogs and efficient methods for making the libraries. In addition, the present invention provides methods of assaying the libraries to identify compounds with beneficial therapeutic effects.

As such, in one aspect, the present invention provides a compound having the formula:

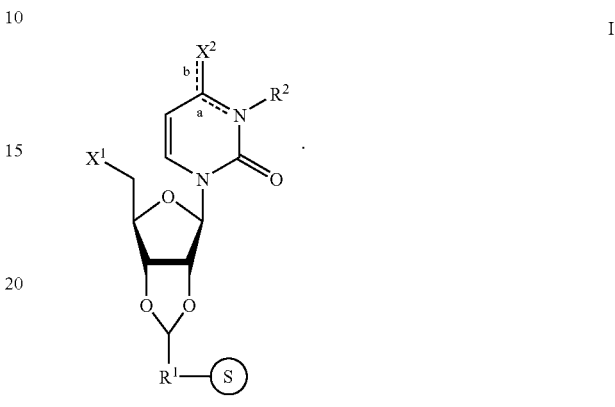

I

In this aspect, the 5' substituent $X^1$ is typically selected from an optionally substituted azidyl or a hydroxyl. The ring substituent $X^2$ is typically selected from an optionally substituted triazolyl, or together with a double bond attached to the ring form a carbonyl. The linker moiety $R^1$ functions to link the sugar ring to the solid support. The nitrogen-linked (N-linked) ring substituent $R^2$ is typically selected from hydrogen, an optionally substituted alkyl, an optionally substituted heteroalkyl, an optionally substituted aryl, an optionally substituted heteroaryl, an optionally substituted heterocycloalkyl, or is absent. The dashed bonds denoted by a and b are single or double bonds. Typically, where a is a single bond, b is a double bond and where a is a double bond, b is a single bond. Finally, the substituent S is a solid phase, such as a solid support.

In another aspect, the present invention provides a compound having the formula:

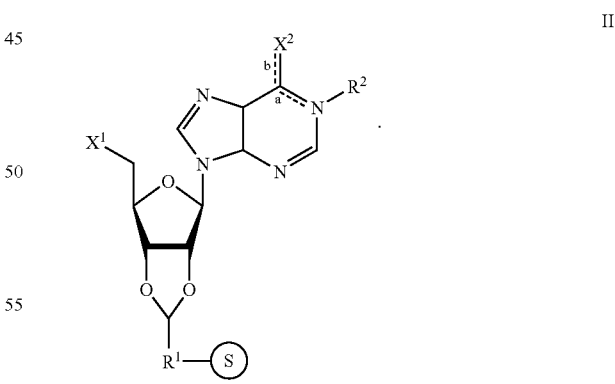

II

In this aspect, the 5' substituent $X^1$ is typically selected from an optionally substituted azidyl or a hydroxyl. The ring substituent $X^2$ is typically selected from chloro, or together with a double bond attached to the ring form a carbonyl. The linker moiety $R^1$ functions to link the sugar ring to the solid phase (e.g. solid support). The N-linked ring substituent $R^2$ is typically selected from hydrogen, an optionally substituted alkyl, an optionally substituted heteroalkyl, an optionally substituted aryl, an optionally substituted heteroaryl, an optionally substituted heterocycloalkyl, or is absent. The dashed bonds denoted by a and b are single or double bonds. Typically, where a is a single bond, b is a double bond and where a is a double bond, b is a single bond. The substituent S is a solid phase.

In yet another aspect, the present invention provides a library of at least 500 compounds having the formula:

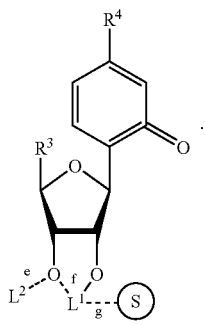

III

In this aspect, the ring substituent $R^3$ is typically selected from $-SR^5$, $-NR^6R^7$, $-NR^8-NR^9R^{10}$, $-NR^{11}-OR^{12}$ or $-OR^{13}$. The substituents $R^5$, $R^6$, $R^7$, $R^8$, $R^9$, $R^{10}$, $R^{11}$, $R^{12}$ and $R^{13}$ are typically selected from hydrogen, an optionally substituted alkyl, an optionally substituted heteroalkyl, an optionally substituted aryl, an optionally substituted heteroaryl, or an optionally substituted heterocycloalkyl.

The substituent $R^4$ is typically selected from:

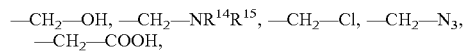

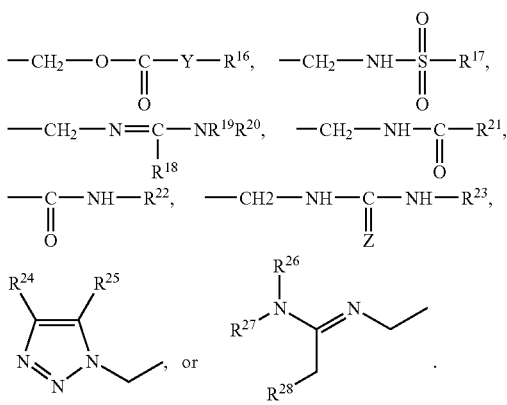

The substituents $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, and $R^{28}$ are each independently selected from hydrogen, an optionally substituted alkyl, an optionally substituted heteroalkyl, an optionally substituted aryl, an optionally substituted heteroaryl, or an optionally substituted heterocycloalkyl. The substituent Z that is double bonded to carbon is typically an oxygen or sulfur. The substituent Y is typically an oxygen or a secondary amine.

The dashed bonds denoted by e, f and g are single bonds or are absent. If e is a single bond then f is absent and g is absent. In addition, if e is absent then f is a single bond and g is a single bond.

$L^1$ is a linker moiety or hydrogen. $L^1$ is hydrogen when e is a single bond. $L^1$ is a linker moiety when e is absent. $L^2$ is hydrogen or is absent. $L^2$ is hydrogen when e is a single bond. $L^2$ is absent when e absent.

S is an optionally present solid phase, such as a solid phase support.

In another aspect, the present invention provides a library of at least 500 compounds having the formula:

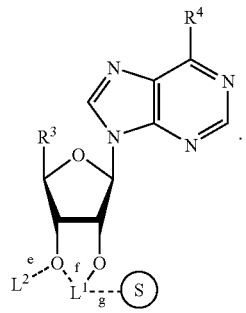

IV

In this aspect, the ring substituent $R^3$ is typically selected from $-SR^5$, $-NR^6R^7$, $-NR^8-NR^9R^{10}$, $-NR^{11}-OR^{12}$ or $-OR^{13}$. The substituents $R^5$, $R^6$, $R^7$, $R^8$, $R^9$, $R^{10}$, $R^{11}$, $R^{12}$ and $R^{13}$ are typically selected from hydrogen, an optionally substituted alkyl, an optionally substituted heteroalkyl, an optionally substituted aryl, an optionally substituted heteroaryl, or an optionally substituted heterocycloalkyl.

The substituent $R^4$ is typically selected from:

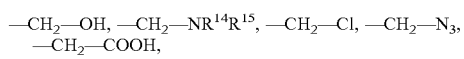

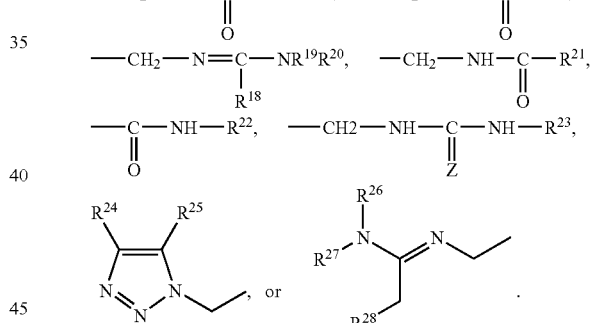

The substituents $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, and $R^{28}$ are typically selected from hydrogen, an optionally substituted alkyl, an optionally substituted heteroalkyl, an optionally substituted aryl, an optionally substituted heteroaryl, or an optionally substituted heterocycloalkyl. The substituent Z that is double bonded to carbon is typically an oxygen or sulfur. The substituent Y is typically an oxygen or a secondary amine.

The dashed bonds denoted by e, f and g are single bonds or are absent. If e is a single bond then f is absent and g is absent. In addition, if e is absent then f is a single bond and g is a single bond.

$L^1$ is a linker moiety or hydrogen. $L^1$ is hydrogen when e is a single bond. $L^1$ is a linker moiety when e is absent. $L^2$ is hydrogen or is absent. $L^2$ is hydrogen when e is a single bond. $L^2$ is absent when e absent.

S is an optionally present solid phase, such as a solid phase support.

In another aspect, the present invention provides a method of preparing a combinatorial chemistry library typically comprising pyrimidine nucleoside analog compounds. The combinatorial chemistry library of compounds has the formula:

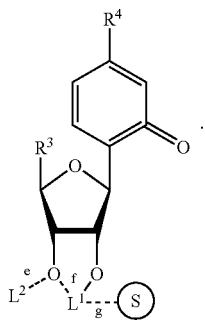

III

In this aspect, a combinatorial chemistry intermediate is subjected to at least one diversity generating reaction to form the combinatorial chemistry library of compounds. The chemistry intermediate has the formula:

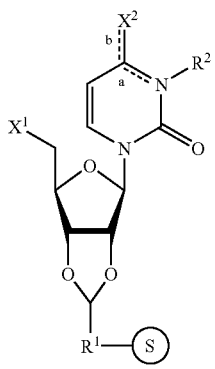

I

In another aspect, the present invention provides a method of preparing a combinatorial chemistry library typically comprising purine nucleoside analog compounds. The combinatorial chemistry library of compounds has the formula:

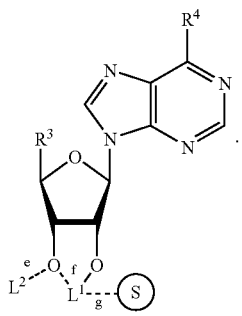

IV

In this aspect, a combinatorial chemistry intermediate is subjected to at least one diversity generating reaction to form the combinatorial chemistry library of compounds. The chemistry intermediate has the formula:

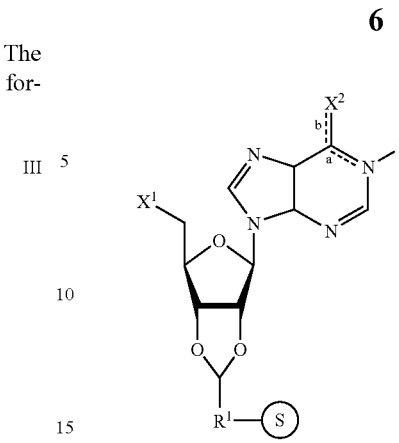

II

In another aspect, the present invention provides a method of screening a library of compounds for an agonist of a purine receptor, the method comprising:
(i) preparing a library of compounds of Formula III; and
(ii) screening the library by contacting the purine receptor with the library.

In another aspect, the present invention provides a method of screening a library of compounds for an agonists of a purine receptor, the method comprising:
(i) preparing a library of compounds of Formula IV; and
(ii) screening the library by contacting the purine receptor with the library.

These and other aspects, objects and advantages will become more apparent when read with the detailed description and figures which follow.

DETAILED DESCRIPTION OF THE INVENTION

Definitions

Figure 1:
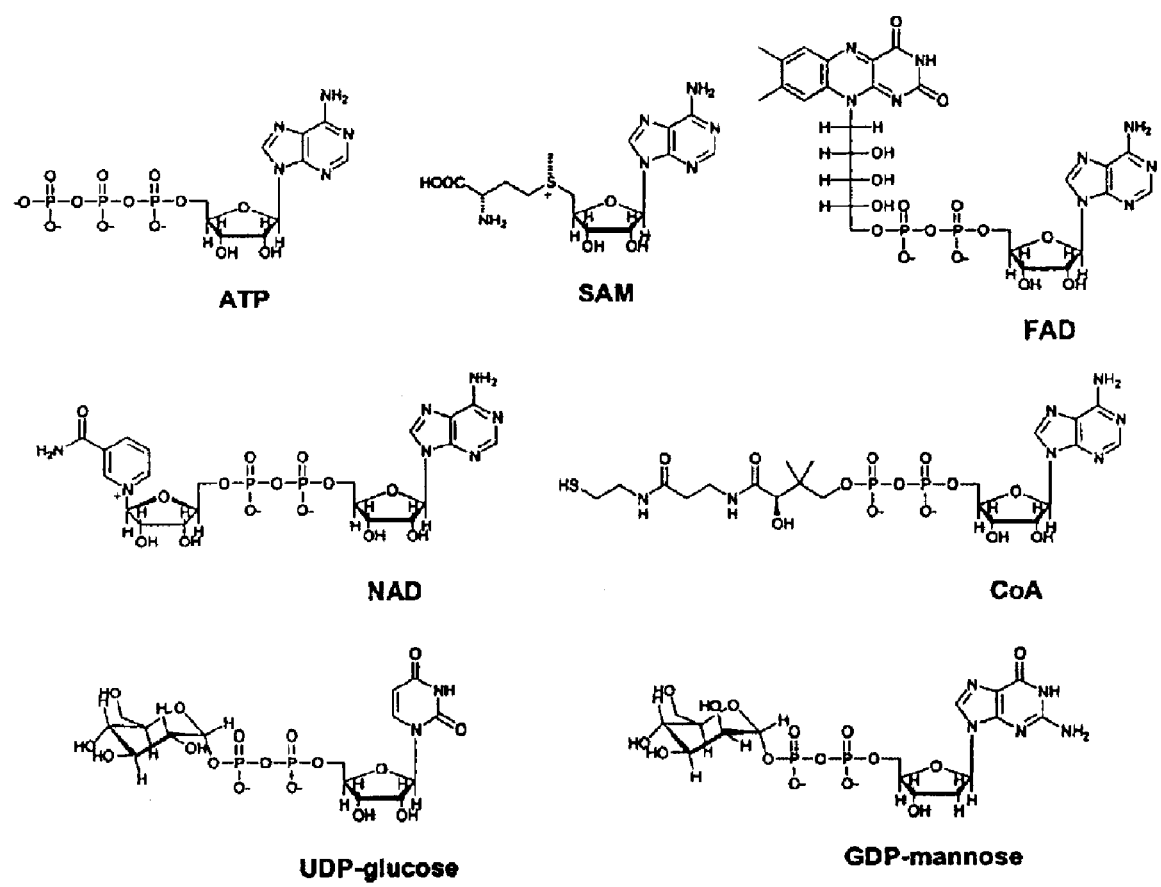
FIG. 1 illustrates exemplary nucleosides in cell metabolism.
Figure 2:
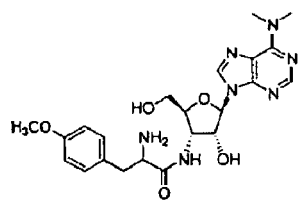
FIG. 2 illustrates exemplary naturally occurring nucleoside analogs with demonstrated selective activities.
Figure 2:
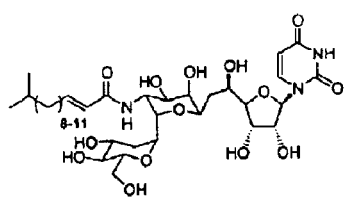
Figure 2:
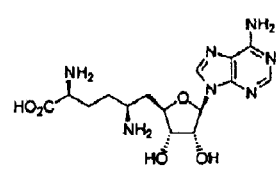
Figure 3:
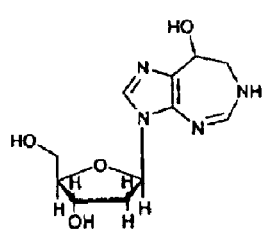
FIG. 3 illustrates exemplary synthetic nucleoside analogs.
Figure 3:
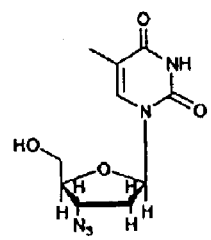
Figure 3:
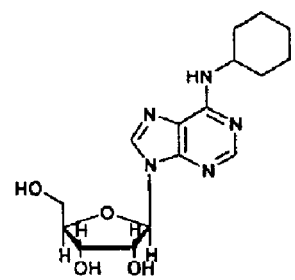

Unless defined otherwise, all technical and scientific terms used herein have the same meaning as commonly understood by one of ordinary skill in the art to which this invention belongs. Generally, the nomenclature used herein and the laboratory procedures in nucleic acid chemistry and screening assays described below are those well known and commonly employed in the art. Standard techniques are used for nucleic acid and nucleoside synthesis and screening assays. Generally, purification steps are performed according to the manufacturer's specifications. The techniques and procedures are generally performed according to conventional methods in the art and various general references (see, generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference) which are provided throughout this document. The nomenclature used herein and the laboratory procedures in analytical chemistry and organic synthetic chemistry described below are those well known and commonly employed in the art. Standard techniques are used for chemical syntheses and chemical analyses.

"Analyte", as used herein means any compound or molecule of interest for which a diagnostic test is desired. An analyte can be, for example, a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, and the like, without limitation.

"Moiety" refers to the radical of a molecule that is attached to another moiety.

It is within the scope of the present invention to include one or more sites that are cleaved by the action of a "cleavage agent" other than an enzyme. Cleavage agents include, but are not limited to, acids, bases, light (e.g., nitrobenzyl derivatives, phenacyl groups, benzoin esters), and heat. Many cleaveable groups are known in the art. See, for example, Jung et al., *Biochem. Biophys. Acta*, 761: 152–162 (1983); Joshi et al., *J. Biol. Chem.*, 265: 14518–14525 (1990); Zarling et al., *J. Immunol.*, 124: 913–920 (1980); Bouizar et al., *Eur. J. Biochem.*, 155: 141–147 (1986); Park et al., *J. Biol. Chem.*, 261: 205–210 (1986); Browning et al., *J. Immunol.*, 143: 1859–1867 (1989).

For the purpose of the present invention, the term "combinatorial library" means an intentionally created collection of molecules based upon a logical design and involving the selective combination of building blocks by means of iterative synthesis used to make the compounds described herein. Each molecular species in the library is referred to as a member of the library. The combinatorial library of the present invention represents a collection of molecules of sufficient number and diversity of design to afford a rich molecular population from which to identify biologically active members. A "combinatorial library," as defined above, involves successive rounds of chemical syntheses based on a common starting structure. Typically, the syntheses are performed in parallel. The combinatorial libraries can be screened in any variety of assays, such as those detailed below as well as others useful for assessing their biological activity. Compounds disclosed in previous work that are not in an intentionally created collection are not part of a "combinatorial library" of the invention. In addition, compounds that are in an unintentional or undesired mixture are not part of a "combinatorial library" of the invention.

The term "in parallel" or "synthesis in parallel" as used herein refers to the process of making a combinatorial library in which successive rounds of chemical syntheses are performed based on a common starting structure. A successive round of chemical synthesis is also referred to herein as a diversity generating reaction. A synthesis in parallel typically involves performing at least two different diversity generating reactions upon compounds with a common structure to from at least two different resulting compounds from the common structure. Successive rounds of diversity generating reactions may then be performed on the resulting compounds to form a larger library of compounds (see, e.g. Exemplary Syntheses 3–8 below).

As used herein, a "solid phase" such as a "solid support" is any form of bead, resin or the like, typically used in the art of solid phase synthesis to provide a "handle" whereby a reactant can be made available for synthetic manipulation without the risk of loss yield typically experienced when such syntheses are conducted in solution; the terms "solid support" and "resin" are used interchangeably. The term "solid support" or, "support," refer to a solid particulate, material to which a nucleic acid, nucleic acid analog, nucleoside or nucleoside analog can be synthesized. Supports used in solid phase synthesis are typically substantially inert and nonreactive with the solid phase synthesis reagents. Methods of using solid supports in solid phase synthesis are well known in the art and may include, but are not limited to, those described in U.S. Pat. Nos. 4,415,732, 4,458,066; 4,500,707, 4,668,777; 4,973,679, and 5,132,418 issued to Caruthers, and U.S. Pat. No. 4,725,677 and Re. 34,069 issued to Koster, and are herein incorporated by reference.

The term "functionalized resin" means any resin, crosslinked or otherwias, where functional groups have been introduced into the resin, as is common in the art. Such resins include, for example, those functionalized with amino, alkylhalo, formyl or hydroxyl groups. Such resins which can serve as solid supports are well known in the art and include, for example, 4-methylbenzhydrylamine-copoly (styrene-1% divinylbenzene) (MBHA), 4-hydroxymethylphenoxymethyl-copoly(styrene-1% divinylbenzene), 4-oxymethyl-phenyl-acetamido-copoly (styrene-1% divinylbenzene(Wang), 4-(oxymethyl)-phenylacetamido methyl (Pam), and TENTAGEL™, from Rapp Polymere Gmbh, trialkoxy-diphenyl-methyl ester-copoly(styrene-1% divinylbenzene)(RINK) all of which are commercially available. Other functionalized resins are known in the art and can be used without departure from the scope of the present invention. Such resins may include those described in Jung et al., *Combinatorial Peptide and Nonpeptide Libraries, A Handbook* (1996) or Bunin et al., *The Combinatorial Index* (1998) and are incorporated herein by reference.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY $5^{TH}$ ED., Longman Scientific and Technical Ltd., Essex, 1991, pp. 809–816; and Heller, *Acc. Chem. Res.* 23: 128 (1990).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. C$_1$–C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

Unless otherwise noted, the use of general chemical terms, such as "alkyl," "azides," "amines," "thiols," "alkoxides," "hydrazines," and "hydroxyamines," are equivalent to their optionally substituted forms. For example, "azides," as used herein, includes optionally substituted azides.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, an optionally substituted heteroalkyl, an optionally substituted aryl, e.g., aryl substituted with 1–3 halogens, an optionally substituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(R'R"R'")—NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$–C$_4$)alkoxy, and fluoro(C$_1$–C$_4$)alkyl, in a number ranging from zero to the total number of open valences on the aromatic ring system; and where R', R", R'" and R"" are preferably independently selected from hydrogen, an optionally substituted alkyl, an optionally substituted heteroalkyl, an optionally substituted aryl and optionally substituted heteroaryl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR—. The substituents R, R', R" and R'" are preferably independently selected from hydrogen or optionally substituted (C$_1$–C$_6$)alkyl.

As used herein, "nucleic acid" means either DNA, RNA, single-stranded, double-stranded, or more highly aggregated hybridization motifs, and any chemical modifications thereof. Modifications include, but are not limited to, those which provide other chemical groups that incorporate additional charge, polarizability, hydrogen bonding, electrostatic interaction, and functionality to the nucleic acid ligand bases or to the nucleic acid ligand as a whole. Such modifications include, but are not limited to, peptide nucleic acids, phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodouracil; backbone modifications, methylations, unusual base-pairing combinations such as the isobases isocytidine and isoguanidine and the like. Modifications can also include 3' and 5' modifications such as capping.

The term "hydroxy" is used herein to refer to the group —OH.

The term "amino" is used to describe primary amines, —NRR', wherein R and R' are independently H, alkyl, aryl or substituted analogues thereof. "Amino" encompasses "alkylamino" denoting secondary and tertiary amines and "acylamino" describing the group RC(O)NR'.

The term "nucleoside" refers to an organic compound comprising a nitrogen-containing purine or pyrimidine base or purine or pyrimidine base analog linked to a sugar. The sugar is typically ribose or deoxyribose.

Compounds

The present invention provides a family of nucleoside analog compounds. In one aspect, the invention provides a compound having the formula:

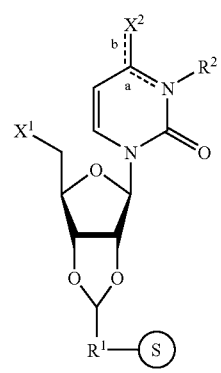

I

In this aspect, the 5' substituent X$^1$ is typically selected from an optionally substituted azidyl or hydroxyl. The ring substituent X$^2$ is typically selected from an optionally substituted triazolyl, or together with a double bond attached to the ring form a carbonyl.

The linker moiety R$^1$ functions to link the sugar ring to the solid support. Linkers are known in the art as moieties which serve to connect a solid support to functional groups (e.g., hydroxyl groups) of initial synthon molecules in solid phase synthetic techniques. Suitable linkers are disclosed in Eckstein et al., *Oligonucleotides and Analogues: A Practical Approach*, (1991). One of skill in the art will recognize that a variety of linker molecules, both acid sensitive and base sensitive, are useful in the present invention.

The nitrogen-linked (N-linked) ring substituent R$^2$ is typically selected from hydrogen, an optionally substituted alkyl, an optionally substituted heteroalkyl, an optionally substituted aryl, an optionally substituted heteroaryl, an optionally substituted heterocycloalkyl, or is absent.

The dashed bonds denoted by a and b are single or double bonds. Typically, where a is a single bond, b is a double bond and where a is a double bond, b is a single bond.

The substituent S is a solid phase. The term "solid phase" is intended to include solid supports, beads, pellets, disks, fibers, gels, resins and other particles. Solid phases are well known substrates which are capable of serving in solid phase synthetic methodologies (see, Definitions section above). Examples of useful solid phases include, for example, PMMA supports, polyacrylamide supports, cellulose supports, latex supports, controlled pore glass supports, geysen pins, optionally functionalized polystyrene supports, optionally substituted copolymers of polyethylene glycol (PEG)-polystyrene (PS) (Castelhano et al., U.S. Pat. No. 6,376,667)) which are herein incorporated by reference, Tentagel™ beads (Ohlmeyer et al., *Proc Natl Acad Sci* 90:10922–10926 (1993), glass, microscope slides, micro titer dishes, and tea bags, Wang resin, Rapp resin, cellulose beads, silica gels, glass particles coated with hydrophobic polymer, etc., i.e., material having a rigid or semi-rigid surface, and soluble supports such as low molecular weight non-cross-linked polystyrene.

In an exemplary embodiment, the solid phase is an optionally derivatized macroporous (macroreticular) polystyrene based resin (Sano et al., *Biochem. Biophys. Acta* 244: 201–205 (1971)).

In another exemplary embodiment, the 5' substituent $X^1$ is azidyl, the ring substituent $X^2$ is triazolyl, the N-linked ring substituent $R^2$ is absent, and the dashed bond a is a double bond and the dashed bond b is a single bond.

In another exemplary embodiment, the 5' substituent $X^1$ is azidyl, the dashed bond b is a double bond together with the ring substituent $X^2$ form a carbonyl, the N-linked ring substituent $R^2$ is hydrogen, and the dashed bond a is a single bond.

In another exemplary embodiment, the 5' substituent $X^1$ is hydroxyl, the ring substituent $X^2$ is triazolyl, the N-linked ring substituent $R^2$ is absent, and the dashed bond a is a double bond and the dashed bond b is a single bond.

In another exemplary embodiment, the linker moiety $R^1$ has the formula:

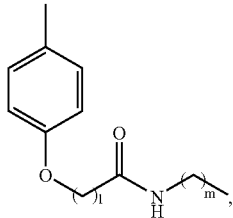

wherein the parenthetical subscripts l and m are integers typically selected from about 1 to about 50.

In another aspect, the invention provides a compound having the formula:

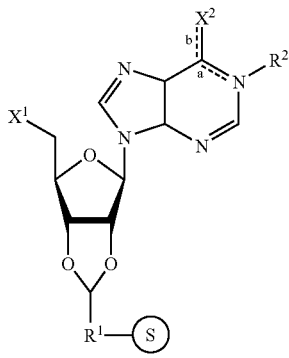

II

In this aspect, the 5' substituent $X^1$ is typically selected from an optionally substituted azidyl or hydroxyl. The ring substituent $X^2$ is typically selected from chloro, or together with a double bond attached to the ring form a carbonyl.

The linker moiety $R^1$ functions to link the sugar ring to the solid support. Linker moieties are well known in the art and are described above.

The nitrogen-linked (N-linked) ring substituent $R^2$ is typically selected from hydrogen, an optionally substituted alkyl, an optionally substituted heteroalkyl, an optionally substituted aryl, an optionally substituted heteroaryl, an optionally substituted heterocycloalkyl, or is absent.

The dashed bonds denoted by a and b are single or double bonds. Typically, where a is a single bond, b is a double bond and where a is a double bond, b is a single bond.

S is a solid phase and is described above. In an exemplary embodiment, the solid phase is an optionally derivatized macroporous (macroreticular) polystyrene based resin.

In another exemplary embodiment, the 5' substituent $X^1$ is azidyl, the ring substituent $X^2$ is chloro, the N-linked ring substituent $R^2$ is absent, and the dashed bond a is a double bond and the dashed bond b is a single bond.

In another exemplary embodiment, the 5' substituent $X^1$ is azidyl, the ring substituent $X^2$ is chloro, the N-linked ring substituent $R^2$ is absent, and the dashed bond a is a double bond and the dashed bond b is a single bond.

In another exemplary embodiment, the 5' substituent $X^1$ is azidyl, the dashed bond b is a double bond together with the ring substituent $X^2$ form a carbonyl, the N-linked ring substituent $R^2$ is hydrogen, and the dashed bond a is a single bond.

In another exemplary embodiment, the 5' substituent $X^1$ is hydroxyl, the ring substituent $X^2$ is chloro, the N-linked ring substituent $R^2$ is absent, and the dashed bond a is a double bond and the dashed bond b is a single bond.

In another exemplary embodiment, the linker moiety $R^1$ has the formula:

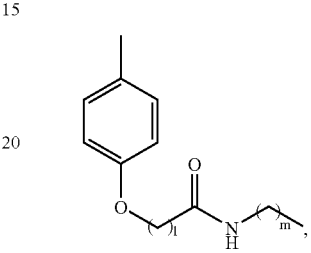

wherein the parenthetical subscripts l and m are integers typically selected from about 1 to about 50.

Exemplary Syntheses

The compounds of the invention are synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention, it is not intended to define the scope of reactions or reaction sequences that are useful in preparing the compounds of the present invention.

Exemplary Synthesis 1

Figure 4:
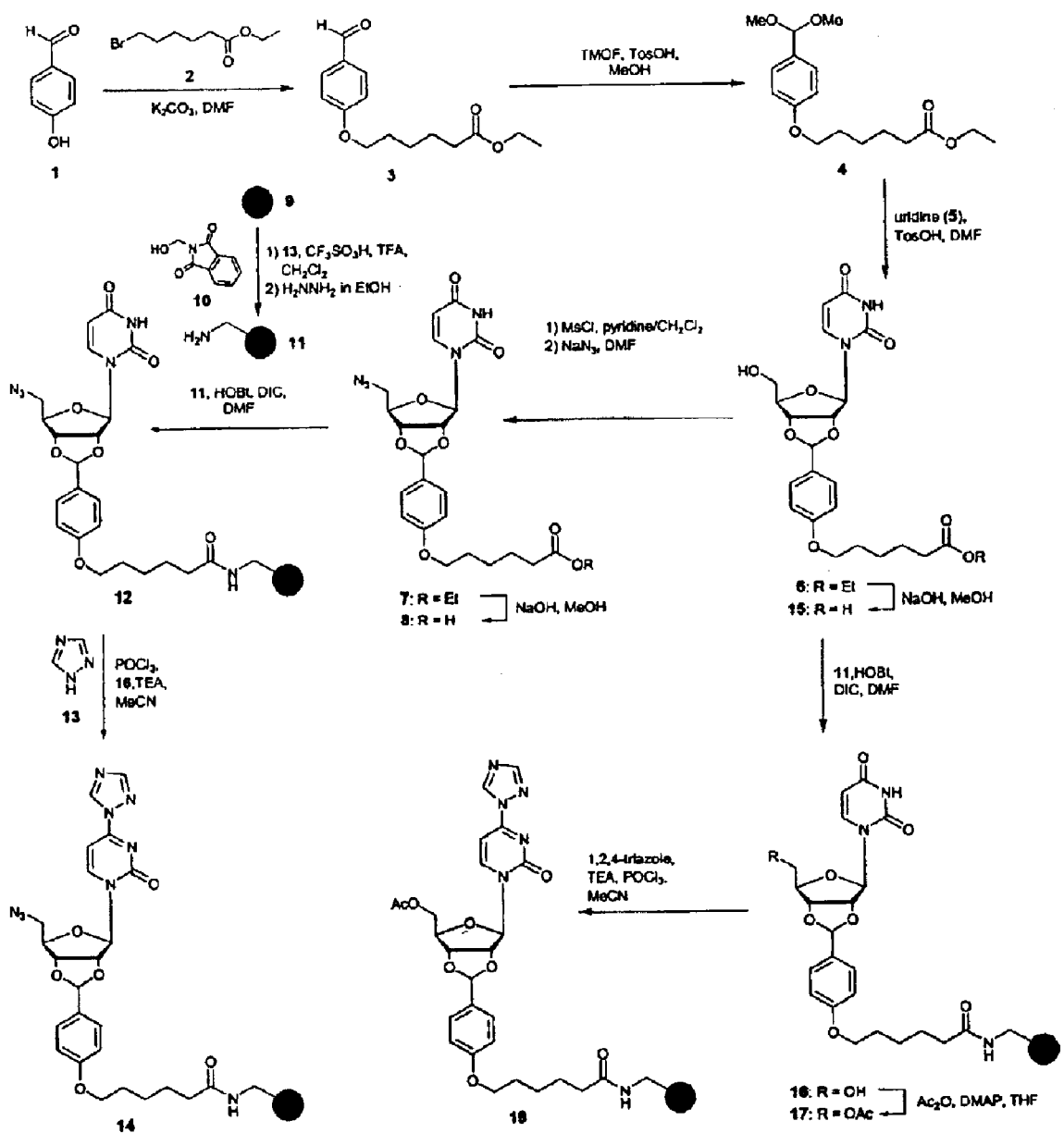
FIG. 4 is an exemplary chemical scheme for the synthesis of solid phase pyrimidine nucleoside analogs.

In the first exemplary synthesis (FIG. 4), solid phase nucleoside pyrimidine analog compounds are provided. The synthesis begins by reacting p-hydroxybenzaldehyde 1 with ethyl-6-bromohexanoate 2 to afford the aldehyde 3, which is activated to the dimethoxyacetal 4. Transketalization with uridine 5 gives the benzylidene 6, which is contacted with the mesylate leaving group at the 5'-position and substituted with azide to yield the 5'-azide 7.

Leaving groups for use in nucleophilic substitution reactions are well known in the art. One skilled in the art will recognize that a variety of leaving groups are useful in the present invention such as, for example, halides, brosylates, tosylates, nosylates, triflates, nonaflates and tresylates.

The 5'-azido ester 7 is then saponified to the carboxylic acid 8. Friedel-Crafts alkylation of unmodified low-crosslinked polystyrene based macroporous solid support 9 with N-(hydroxymethyl)phtalimide 10 and subsequent deprotection by hydrazinolysis yields the aminomethyl-functionalized resin 11.

The aminomethyl substitution level is determined by Fmoc-quantitation following standard procedures. The carboxylic acid 8 is then coupled to the aminomethyl resin 11 using diisopropylcarbodiimide (DIC) and N-hydroxybenzotriazole (HOBt) activation to afford resin 12.

Activation of amine groups to form amide bond are well known in the art (see, e.g., Stewart et al., *Solid Phase Peptide Synthesis*, 2nd Ed., 1984). One of skill in the art will recognize that a variety of coupling reagents are useful in the present invention, including, but not limited to, phosphonium reagents (e.g. benzotriazol-1-yl-oxytripyrrolidinophosphonium hexafluorophosphate (PyBOP), benzotriazole-1-yl-oxy-tris-(dimethylamino)-phosphonium hexafluorophosphate (BOP)), tetramethyluronium reagents (e.g. O-benzotriazol-1-yl-N,N,N',N'-tetramethyluronium hexafluorophosphate (HBTU), O-benzotriazol-1-yl-tetramethyltetrafluoroborate (TBTU), 1H-benzotriazolium 1-(bis(dimethylamino)methylene)-5chloro-, hexafluorophosphate (1-),3-oxide (HCTU), 1-H-benzotriazolium-1-(bis(dimethylamino)methylene)-5chloro-,tetrafluoroborate(1-),3-oxide (TCTU)), and carbodiimide reagents (e.g. dicyclohexylcarbodiimide (DCC,) and M-ethyl-N'-(3dimethylaminopropyl) carbodiimide (EDC)). Those of skill in the art will know of other coupling reagents useful in the present invention.

The uridine 12 is activated with triazole 13 in the presence of phosphorus oxychloride ($POCl_3$) in basic media yielding the solid phase 4-triazolo activated pyrimidine 14.

Alternatively, benzylidene 6 is saponified to the carboxylic acid 15 and loaded on to the aminomethyl resin 11 to give 16. Protection of the 5'-hydroxyl group with acetic anhydride ($Ac_2O$) in the presence of 4-dimethylaminopyridine (DMAP) affords the 5'-acetyl derivative 17, which is activated to the solid phase 4-triazolo-5'-acetyl pyrimidine 18.

Exemplary Synthesis 2

Figure 5:
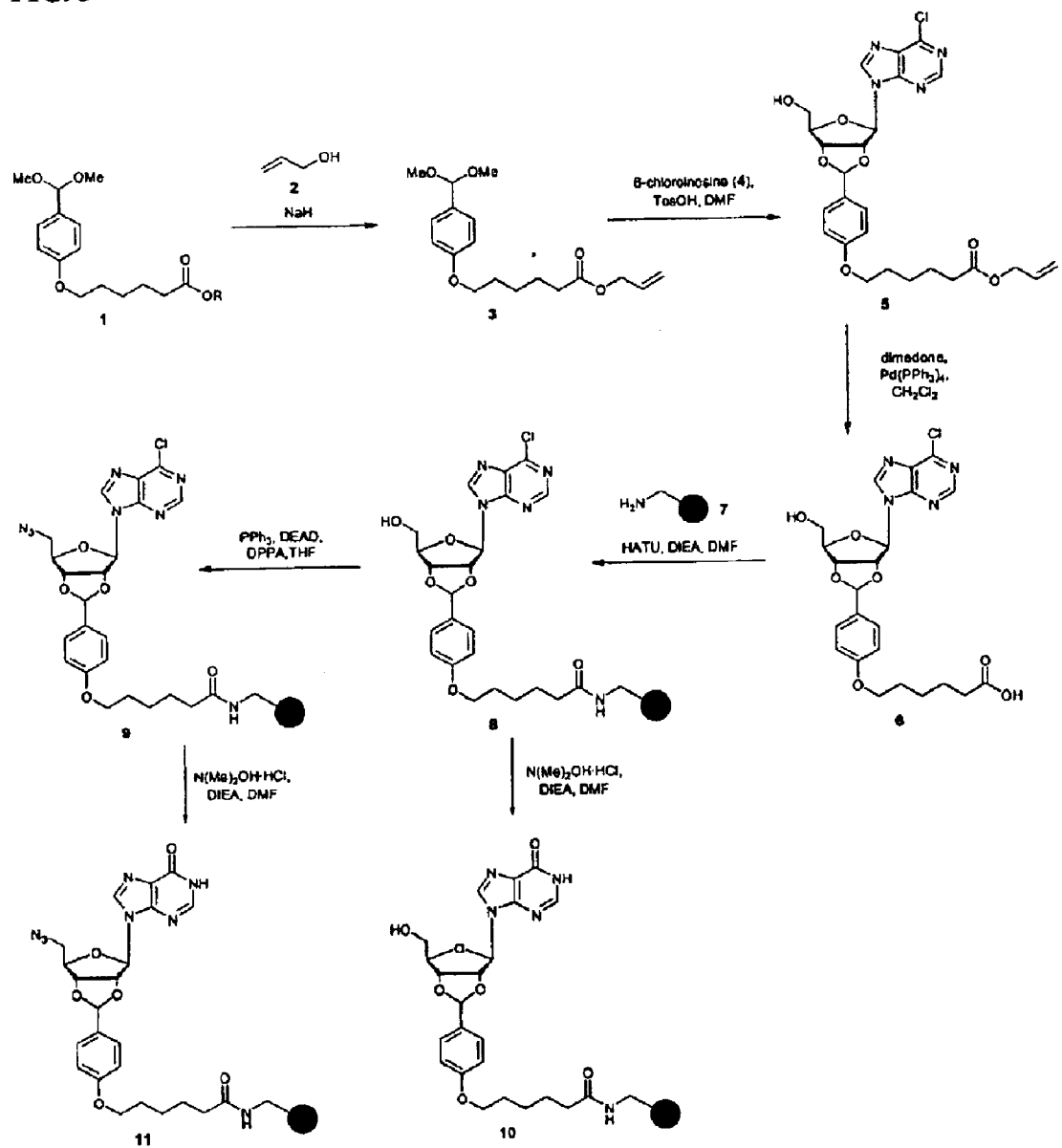
FIG. 5 is an exemplary chemical scheme for the synthesis of solid phase purine nucleoside analogs.

In the second exemplary synthesis (FIG. 5), the purine compounds 8, 9, 10 and 11 are provided. The synthesis begins with the transesterification of the ethyl ester 1 with allyl alcohol 2 to the allyl ester 3.

Next, transketalization of the dimethoxyacetal 3 with 6-chloroinosine 4 gives the 6-chloroinosine allyl ester 5. Palladium catalyzed saponification of 5 yields the carboxylic acid derivative 6. The coupling of 6 onto the aminomethyl functionalized macroporous resin 7 to give the solid phase purine 8 is carried out using N-((Dimethylamino)-1H-1,2,3-triazolo(4,5-b)pyridin-1-ylmethylene)-N-methylmethanaminium hexafluorophosphate N-oxide (HATU) activation. Solid phase 5'-azide 9 is generated from 8 using Mitsunobu conditions with diphenyl phosphoryl azide (DPPA). Finally, the treatment of 8 and 9 with N,N-dimethyl hydroxylamine affords the corresponding solid phase inosine compounds 10 and 11.

Exemplary Synthesis 3

Figure 6:
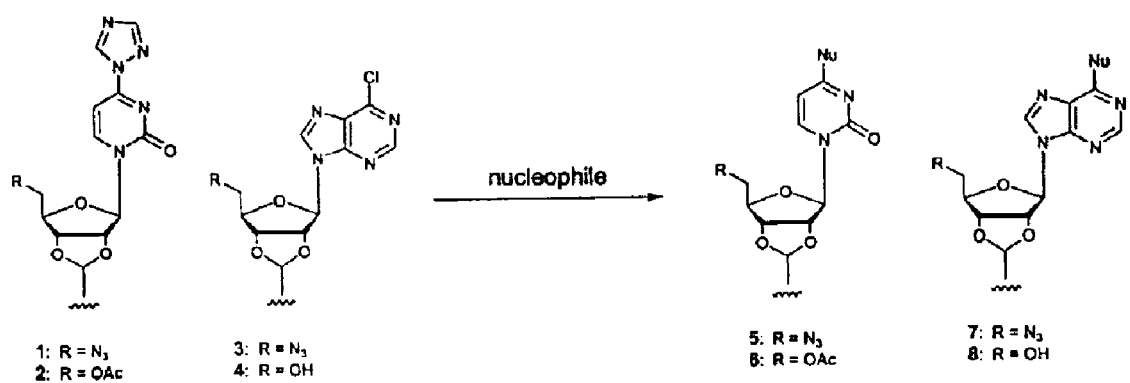
FIG. 6 is an exemplary chemical scheme for the synthesis of solid phase purine nucleoside analogs.

In the third exemplary synthesis (FIG. 6), a diversity generating reaction is provided. In one aspect, diversity is generated by nucleophilic aromatic substitution of the solid phase purine and pyrimidine compounds 1, 2, 3, and 4 to afford the variably substituted products 5, 6, 7, and 8.

Nucleophilic substitution reactions are well known in the art. One of skill in the art will recognize that a variety of nucleophiles are useful in the present invention, including, but not limited to, azides, amines, thiols, alkoxides, hydrazines, hydroxyamines, and tetraethylammonium cyanide.

Exemplary Synthesis 4

In the fourth exemplary synthesis (FIG. 7), diversity generating reactions are provided to diversify the 5' end of solid phase purine and pyrimidine compounds. In exemplary reaction a, cycloaddition of a variably substituted alkyne to the 5'-azido functionality of solid phase pyrimidine 1 and purine 2 compounds generates the variably substituted 5'-triazole products 3, 4, 5, and 6.

Akyne substituents are well known in the art. One of skill in the art would realize that a variety of alkyne substituents are useful in the present invention. Examples of alkyne substituents include, but are not limited to alkyls, aryls, methyl halides, esters, and silanes.

Alternatively, the azides 1 and 2 are reduced to the corresponding amines 7 and 8 using stannous chloride and thiophenol. The free amines 7 and 8 are then treated with various acylation reagents (reaction c: HOBt/DIC activated carboxylic acids; reaction d: isocyanates; reaction e: isothiocyanates; and reaction f: aryl sulfonyl chlorides) to give the corresponding variably substituted amides (9 and 10), ureas (11 and 12), thioureas (13 and 14) and aryl sulfonamides (15 and 16).

Exemplary Synthesis 5

Figure 8:
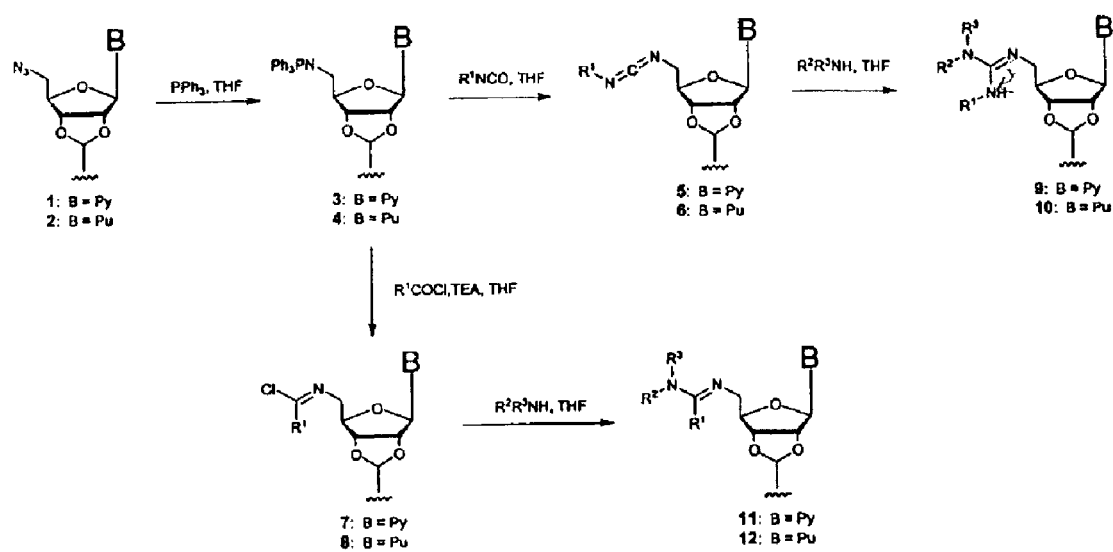
FIG. 8 is an exemplary chemical scheme for the synthesis of solid phase purine and pyrimidine nucleoside analogs.

In the fifth exemplary synthesis (FIG. 8), diversity generating reaction are provided to diversify the 5' end of solid phase purine and pyrimidine compounds. In this exemplary synthesis, the Staudinger reaction is used to produce variably substituted solid phase purine and pyrimidine compounds through phospinamine intermediates (Drewry et al., *Tetrahedron Lett*. 38: 3377–3380 (1997)).

The azides 1 and 2 are first transformed to their phospho-aza-ylide derivatives 3 and 4 with triphenylphosphine. Intermediate solid phase phosphinamines 3 and 4 are treated with isocyanates to give the variably substituted carbodiimides 5 and 6. Alternatively, treatment with acid chlorides results in the formation of the variably substituted imino chlorides 7 and 8. To afford further diversification, the carbodiimides, 5 and 6, and imino chlorides, 7 and 8, are then quenched with excess amine to yield the variably substituted guanidines 9 and 10 and the variably substituted amidines 11 and 12, respectively.

Exemplary Synthesis 6

Figure 9:
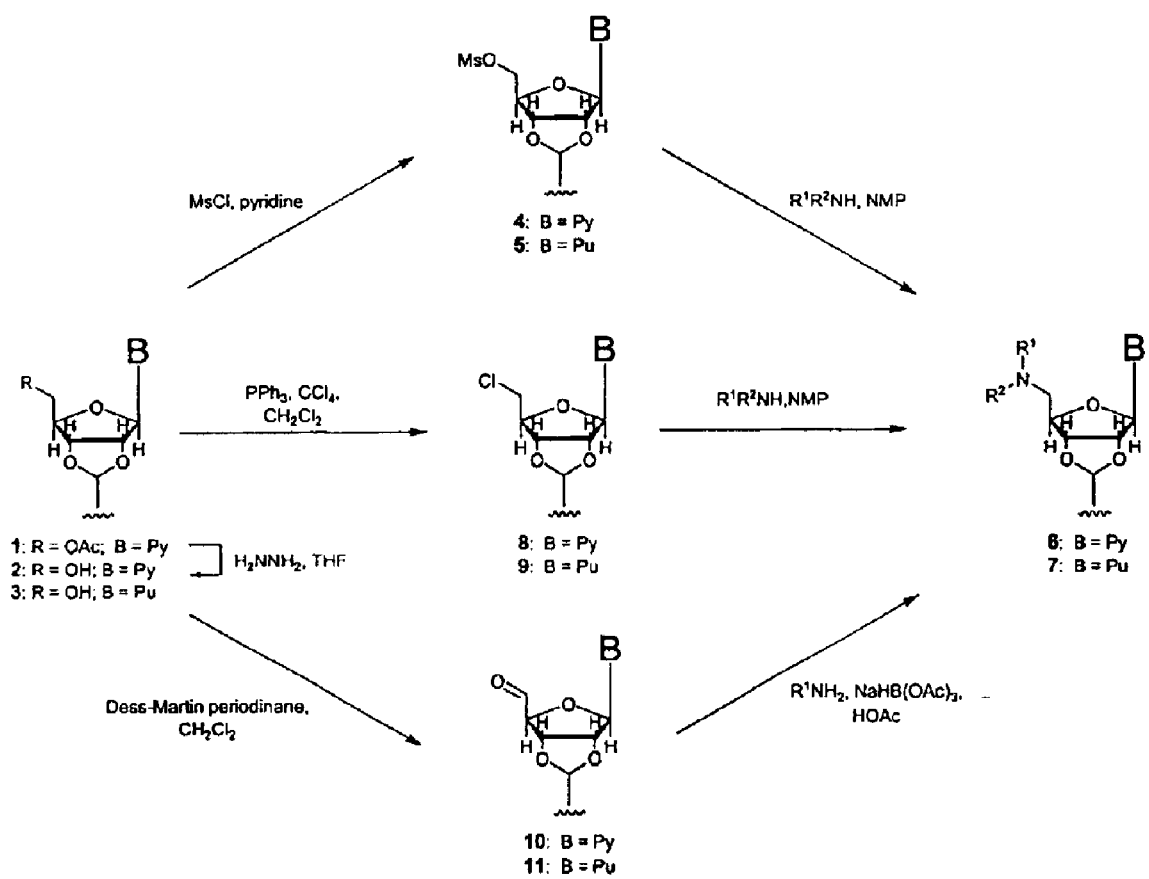
FIG. 9 is an exemplary chemical scheme for the synthesis of solid phase purine and pyrimidine nucleoside analogs.

In the sixth exemplary synthesis (FIG. 9), three routes containing diversity generating reactions are provided to yield the variably substituted 5'-amines 6 and 7. The routes begin with the 5'-alcohol functionality of solid phase pyrimidine 2 and purine 3 compounds.

First, a hydrazinolysis of the solid phase 5'-acetoxy-pyrimidine 1 deprotects the 5'-alcohol functionality to the corresponding unprotected 5'-alcohol pyrimidine 2 (Roush et al., *J. Am. Chem. Soc*. 117: 2236–2250 (1995)). Both 5'-alcohol compounds 2 and 3 are converted into the 5'-mesylates 4 and 5 using mesyl chloride in pyridine (Ceulemans et al., *Nucleosides Nucleotides* 14: 117–128 (1995)). Displacement of the 5'-mesylate with the appropriate amine provides the variably substituted pyrimidine and purine 5'-amines 6 and 7.

Alternatively, chlorination of the 5'-position of 2 and 3 using triphenylphosphine and carbon tetrachloride leads to the 5'-chlorides 8 and 9 (Robins et al., *Nucleosides Nucleotides* 19: 69–86 (2000)). Displacement of the 5'-chloride with the appropriate amine provides the variably substituted pyrimidine and purine 5'-amines 6 and 7.

Yet another route to substituted 5'-amines is reductive amination. After oxidation of the 5'-alcohol 2 and 3 to the corresponding aldehydes 10 and 11 using Dess-Martin periodinane (Dess et al., *J. Org. Chem*. 4: 4155–4156 (1983)), treatment with the appropriate primary amine in the presence of sodium triacetoxyborohydride results in the monosubstituted 5'-amines 6 and 7.

Exemplary Synthesis 7

Figure 10:
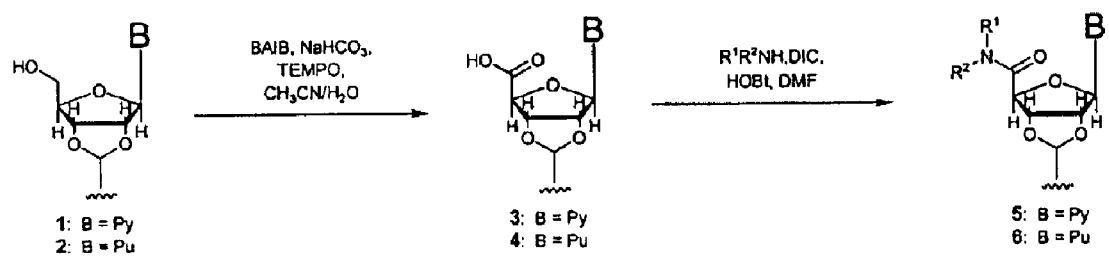
FIG. 10 is an exemplary chemical scheme for the synthesis of solid phase purine and pyrimidine nucleoside analogs.

In the seventh exemplary synthesis (FIG. 10), diversity generating reactions are provided to produce solid phase 5'-uronamide pyrimidine and purine compounds 5 and 6 from the 5'-alcohol pyrimidine and purine compounds 1 and 2. This exemplary synthesis begins with direct oxidation of the 5'-alcohol of 1 and 2 using 2,2,6,6-tetramethyl-piperidinyloxyl (TEMPO) as an oxidization catalyst and bisacetoxy-iodobenzene (BAIB) as the oxidant resulting in conversion to the corresponding carboxylic acids 3 and 4. Amide bond formation with the appropriate amines using HOBt/DIC activation leads to the variably substituted solid phase uronamides 5 and 6.

Exemplary Synthesis 8

Figure 11:
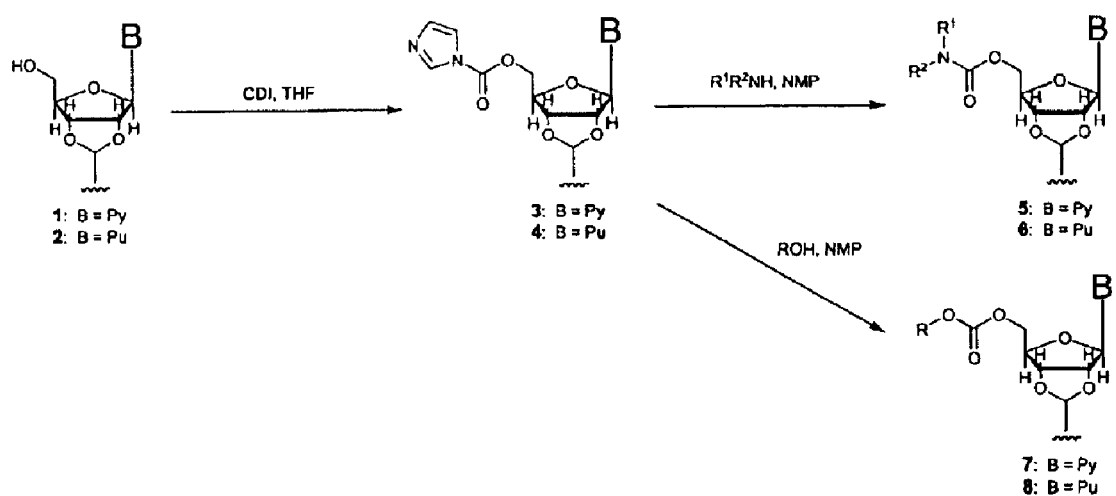
FIG. 11 is an exemplary chemical scheme for the synthesis of solid phase purine and pyrimidine nucleoside analogs.

In the eighth exemplary synthesis (FIG. 11), diversity generating reactions are provided to produce solid phase 5'-carbamate compounds 5 and 6 and solid phase 5'-carbanate compounds 7 and 8 from the 5'-alcohol pyrimidine and purine compounds 1 and 2 using 5'-imidazole intermediates 3 and 4. Carbonylation of 1 and 2 using carbonyldiimidazole (CDI) gives the intermediates 3 and 4, which are quenched with the appropriate amines to yield variably substituted 5'-carbamate compounds 5 and 6. Quenching with alcohols result in the formation of the carbonates 7 and 8.

Exemplary Synthesis 9

In the ninth exemplary synthesis (FIG. 12), solid phase purine 1 and pyrimidine compounds 2 are released from solid support to form the corresponding variably substituted solution phase compounds 3 and 4. Cleavage of the acetal linkage is accomplished with trifluoroacetic acid.

Figure 12:
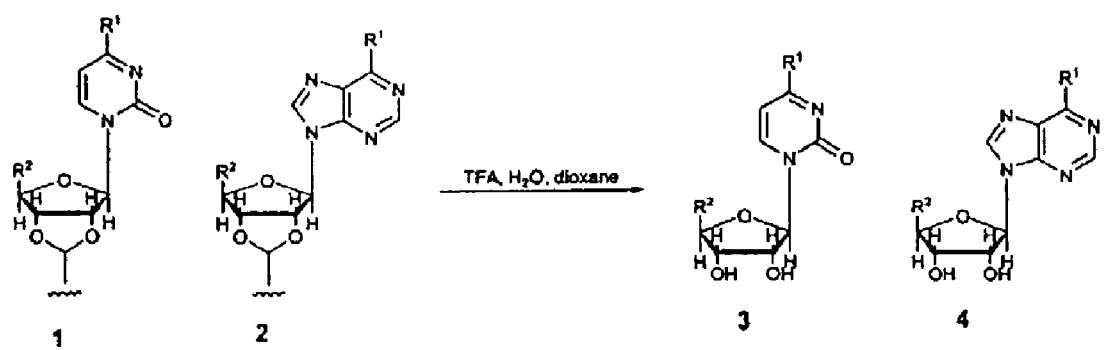
FIG. 12 is an exemplary chemical scheme for the synthesis of solution phase purine and pyrimidine nucleoside analogs.
Figure 13A:
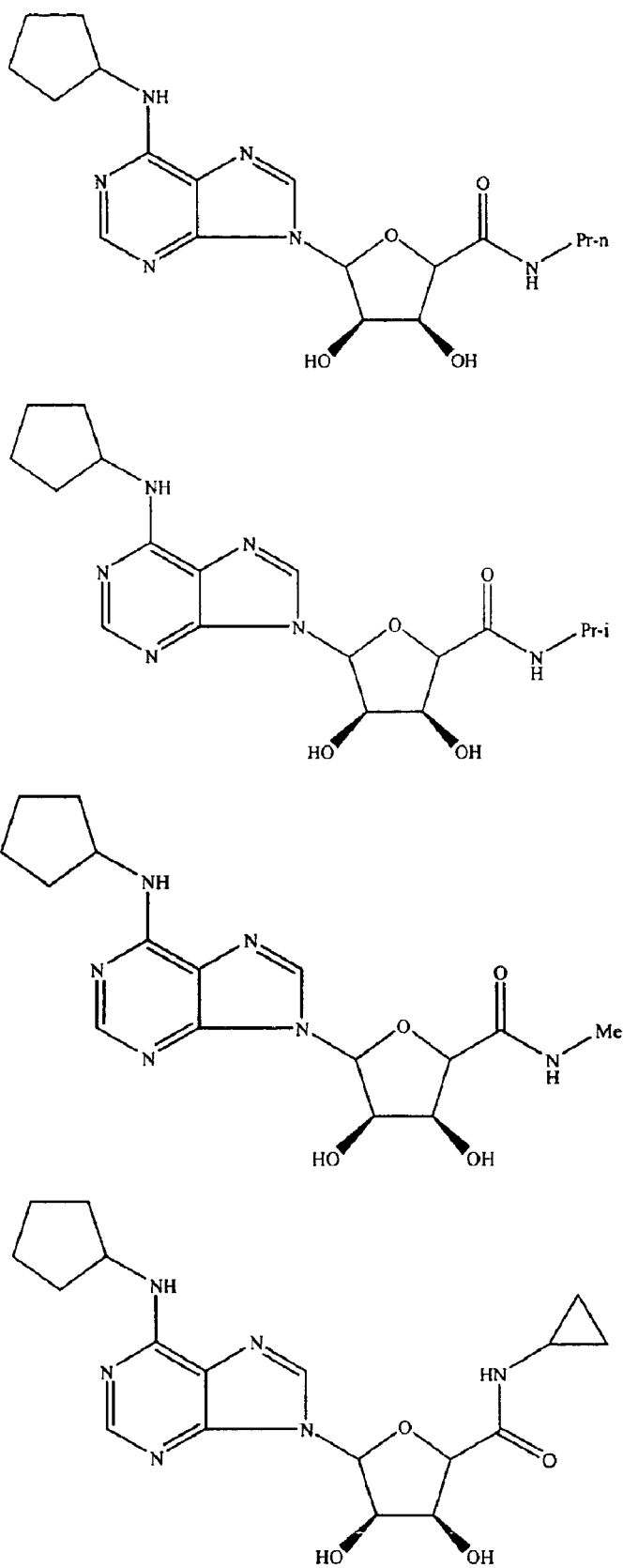
FIGS. 13(A–Q) illustrate an exemplary combinatorial library.
Figure 13B:
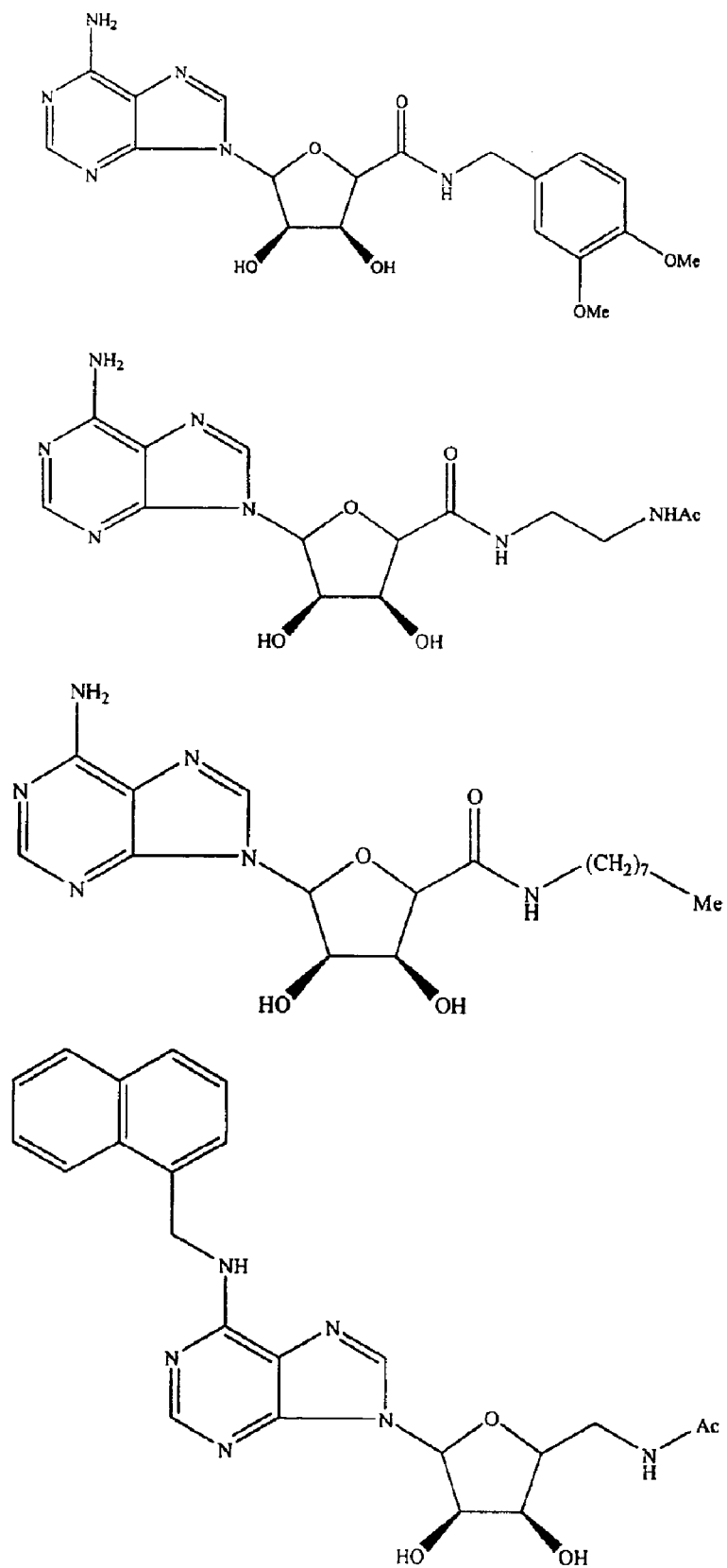
Figure 13C:
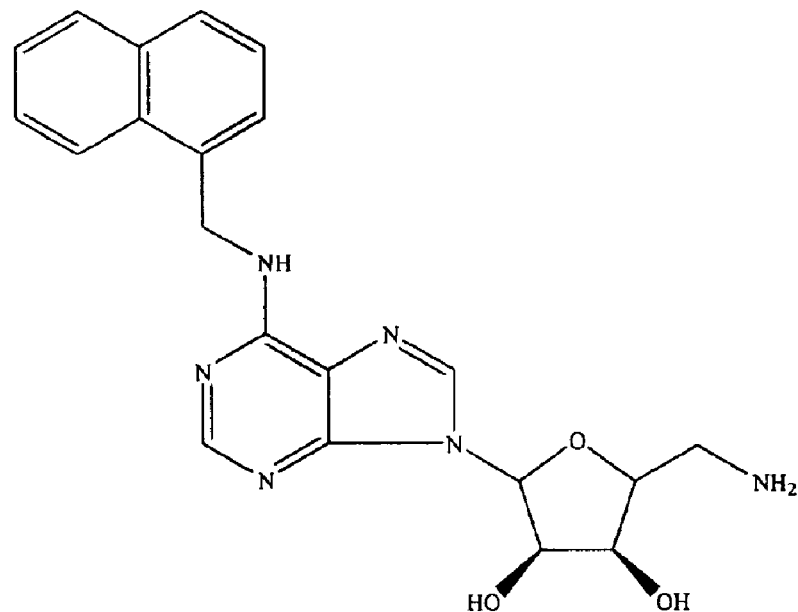
Figure 13C:
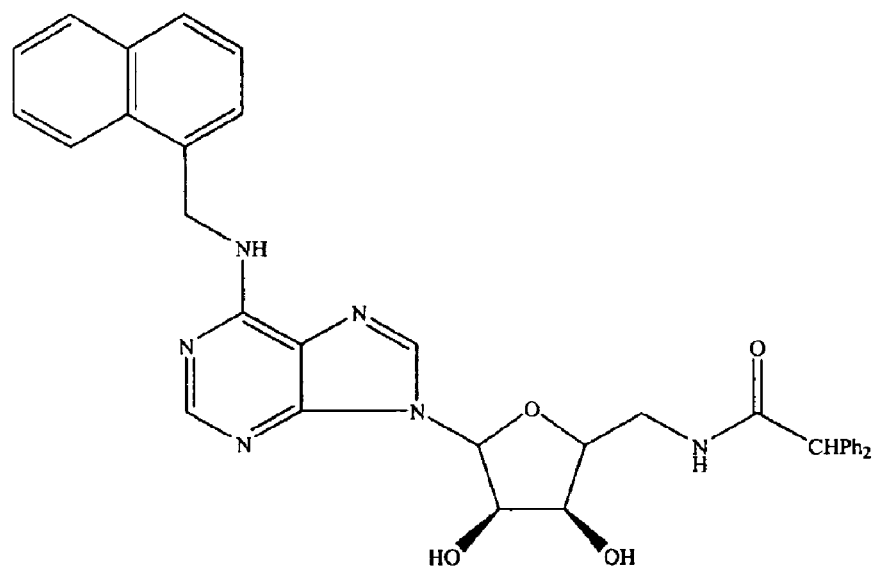
Figure 13C:
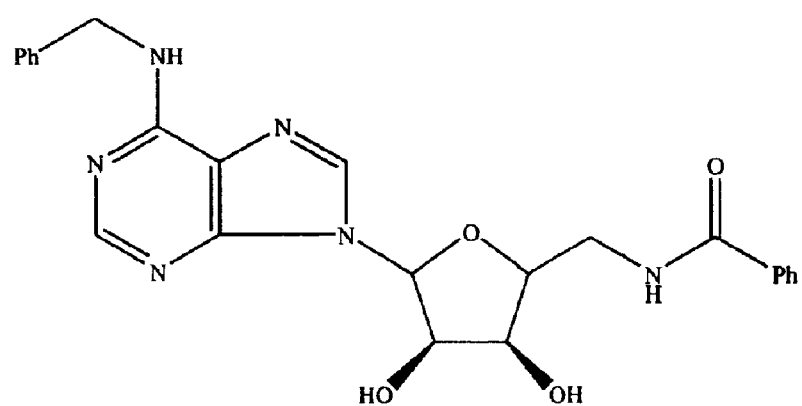
Figure 13D:
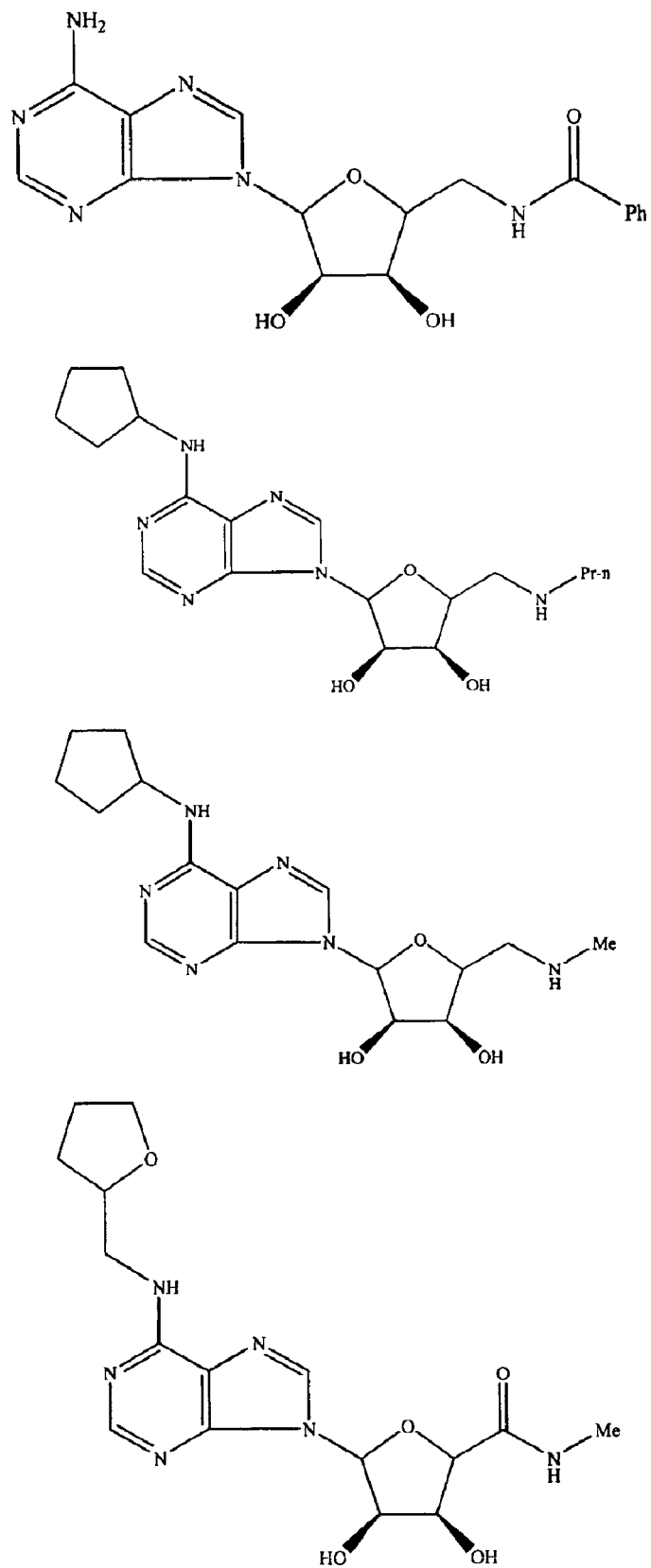
Figure 13E:
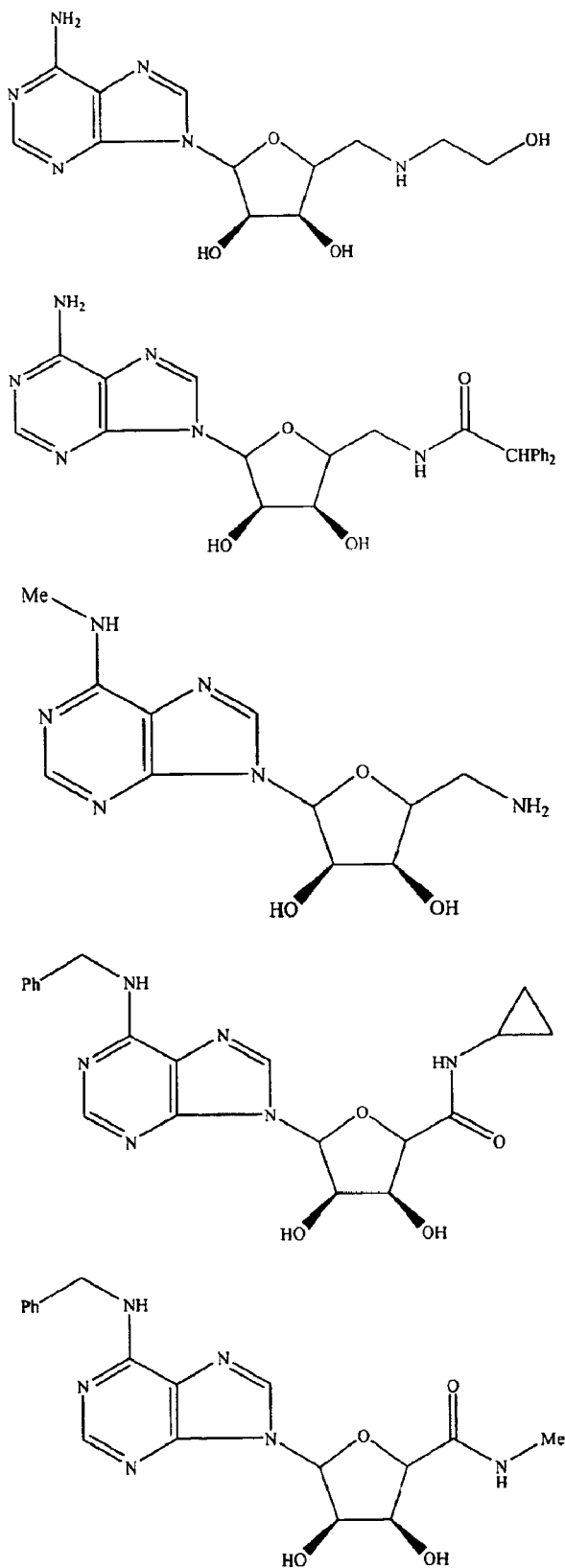
Figure 13F:
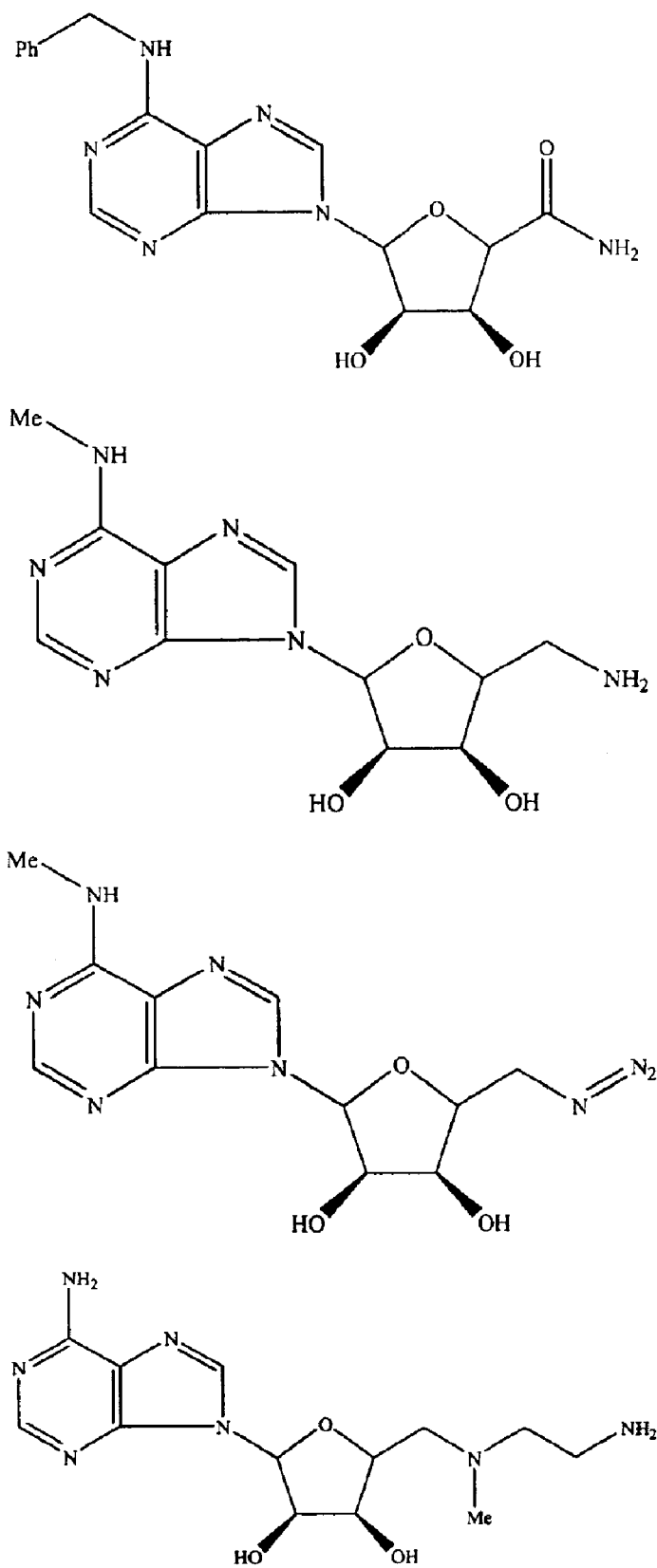
Figure 13G:
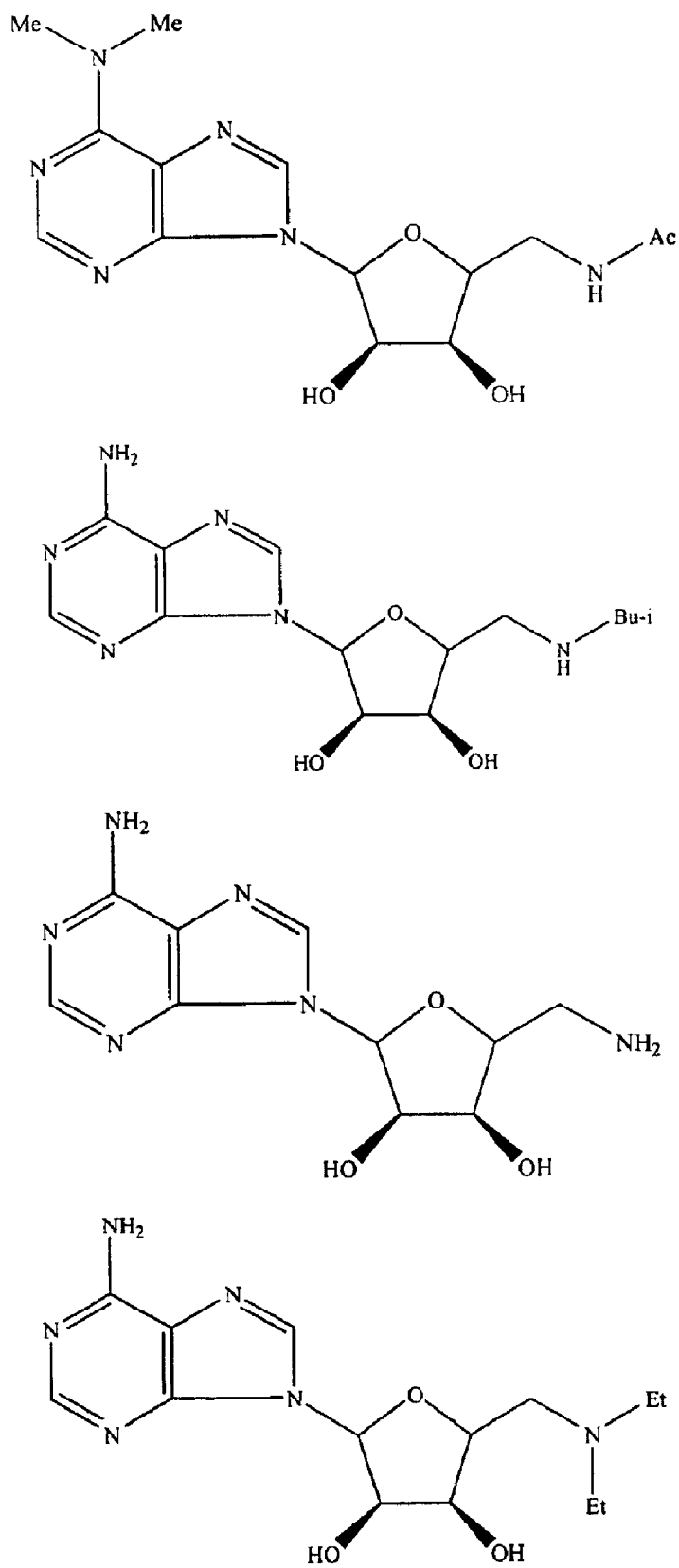
Figure 13H:
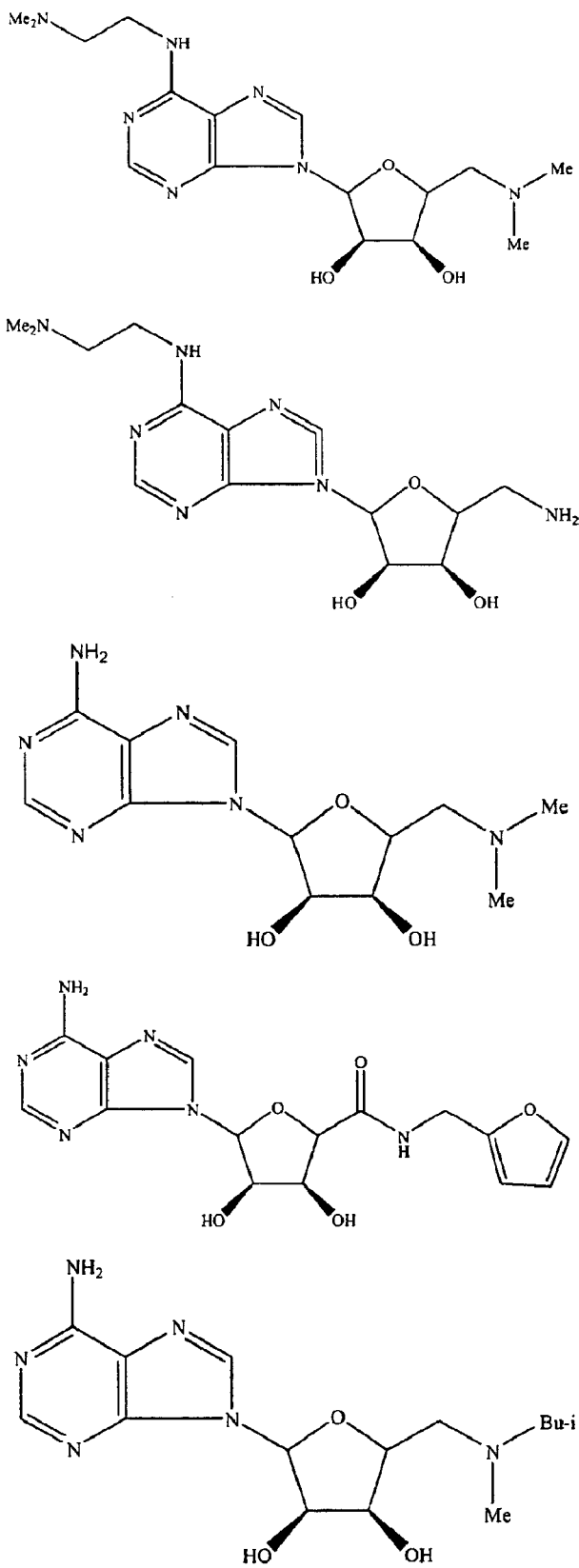
Figure 13I:
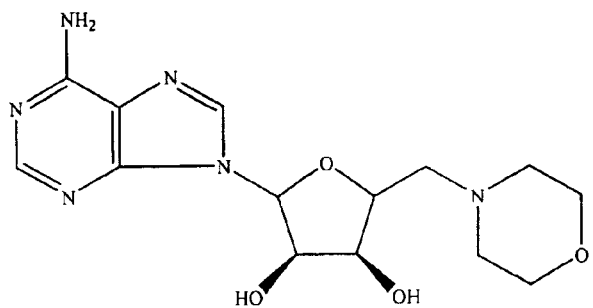
Figure 13I:
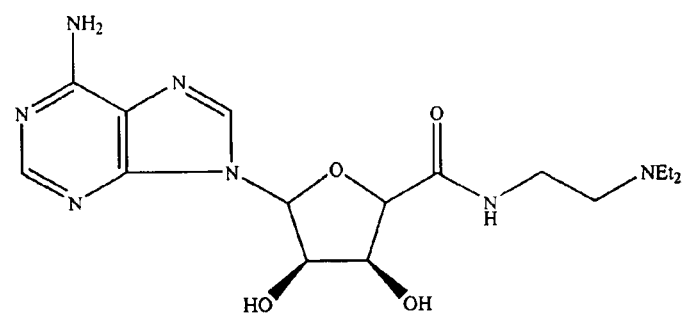
Figure 13I:
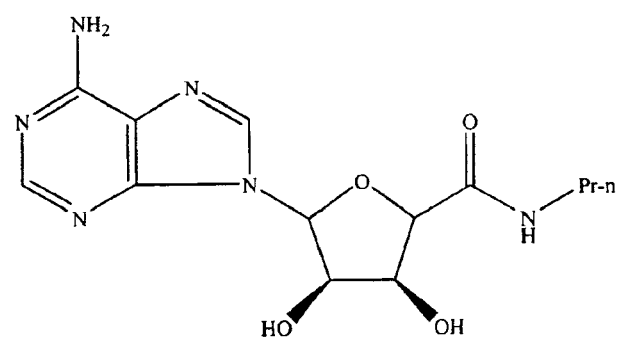
Figure 13I:
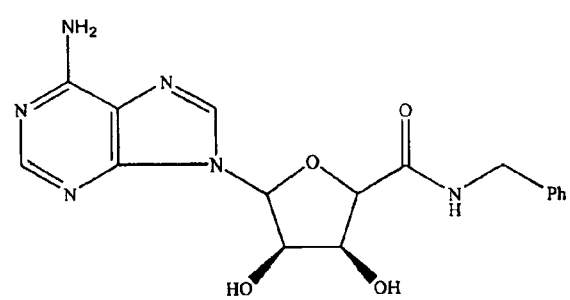
Figure 13I:
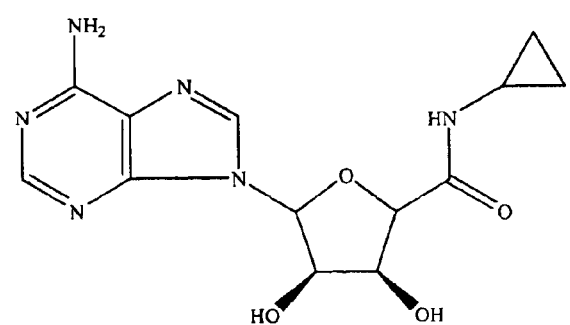
Figure 13J:
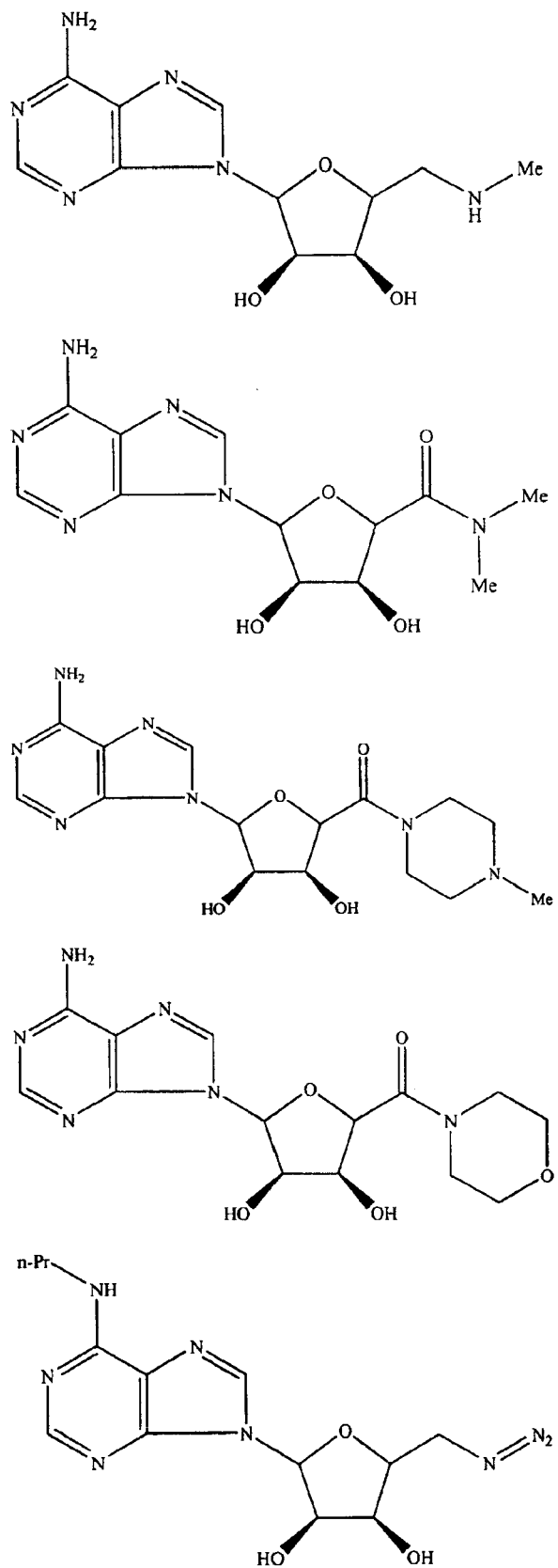
Figure 13K:
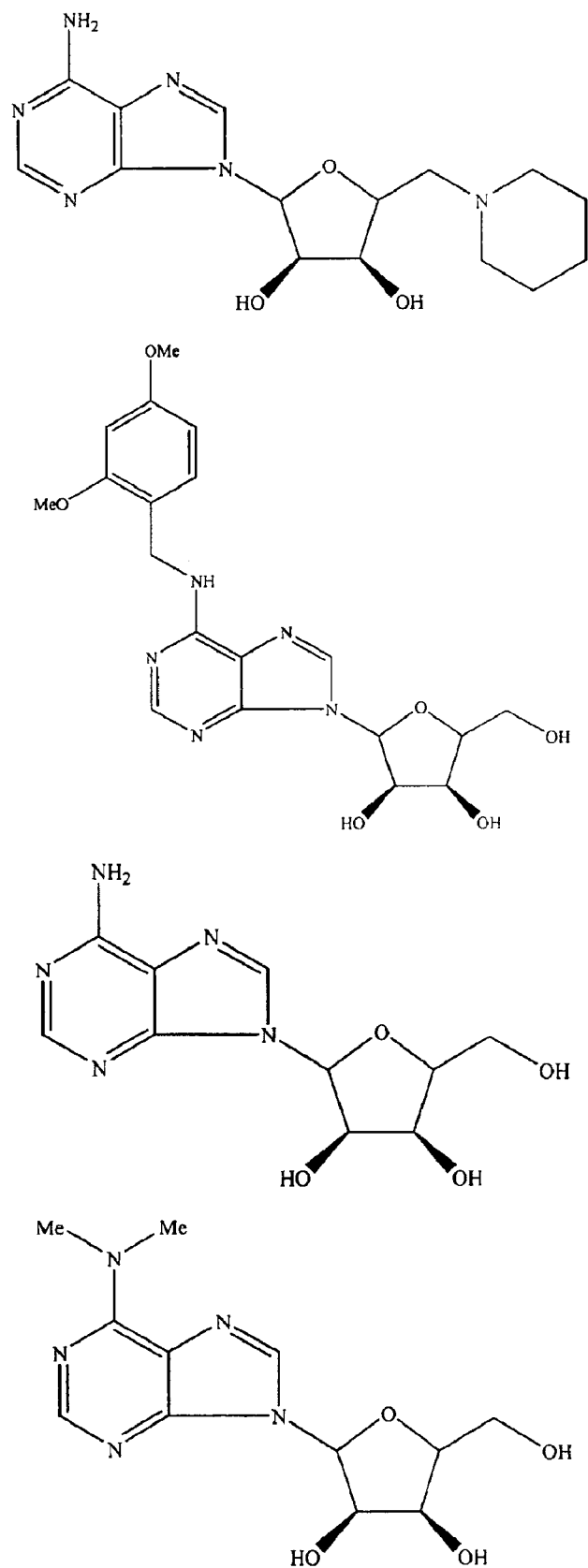
Figure 13L:
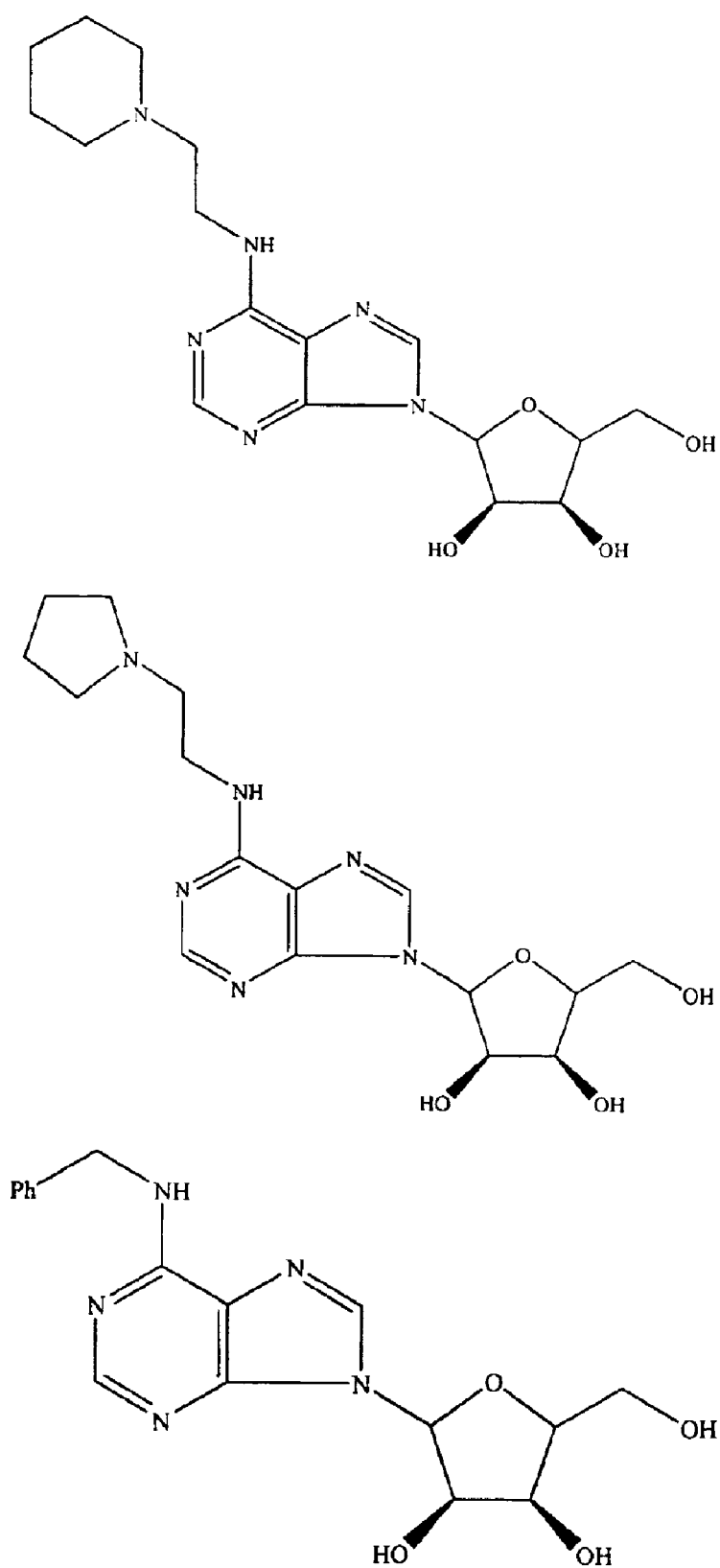
Figure 13M:
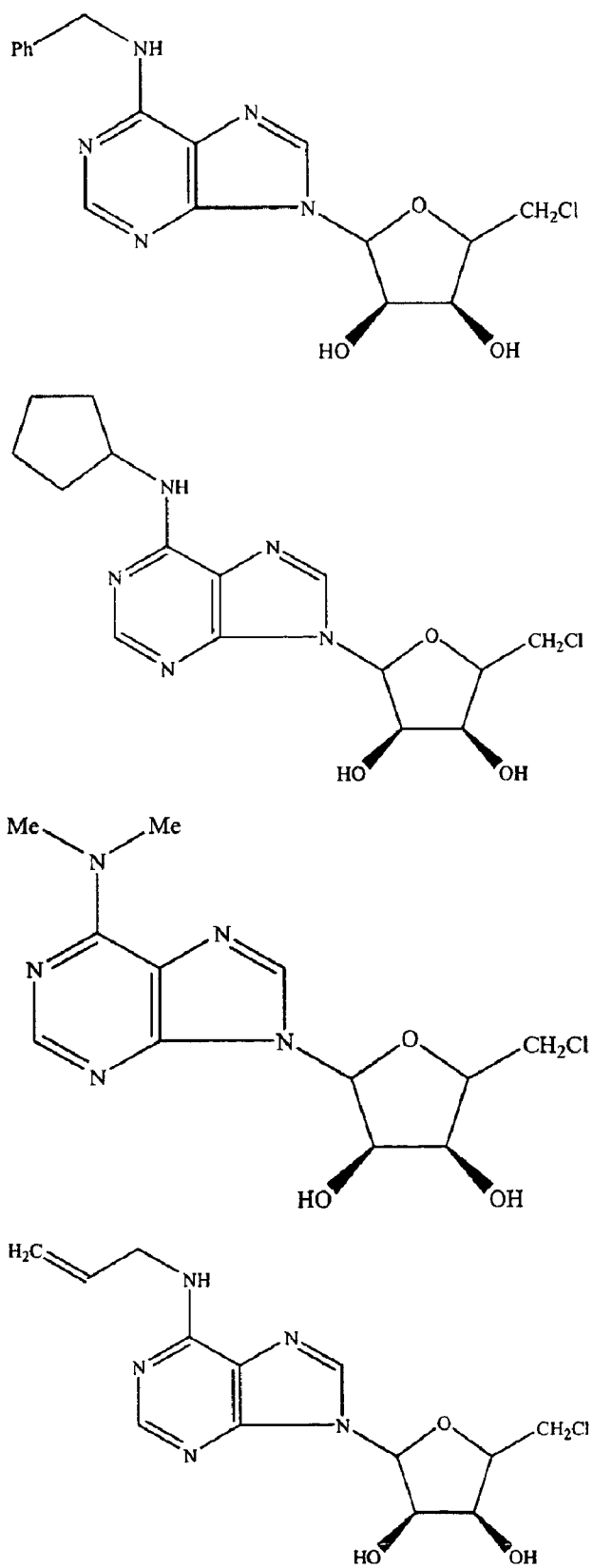
Figure 13N:
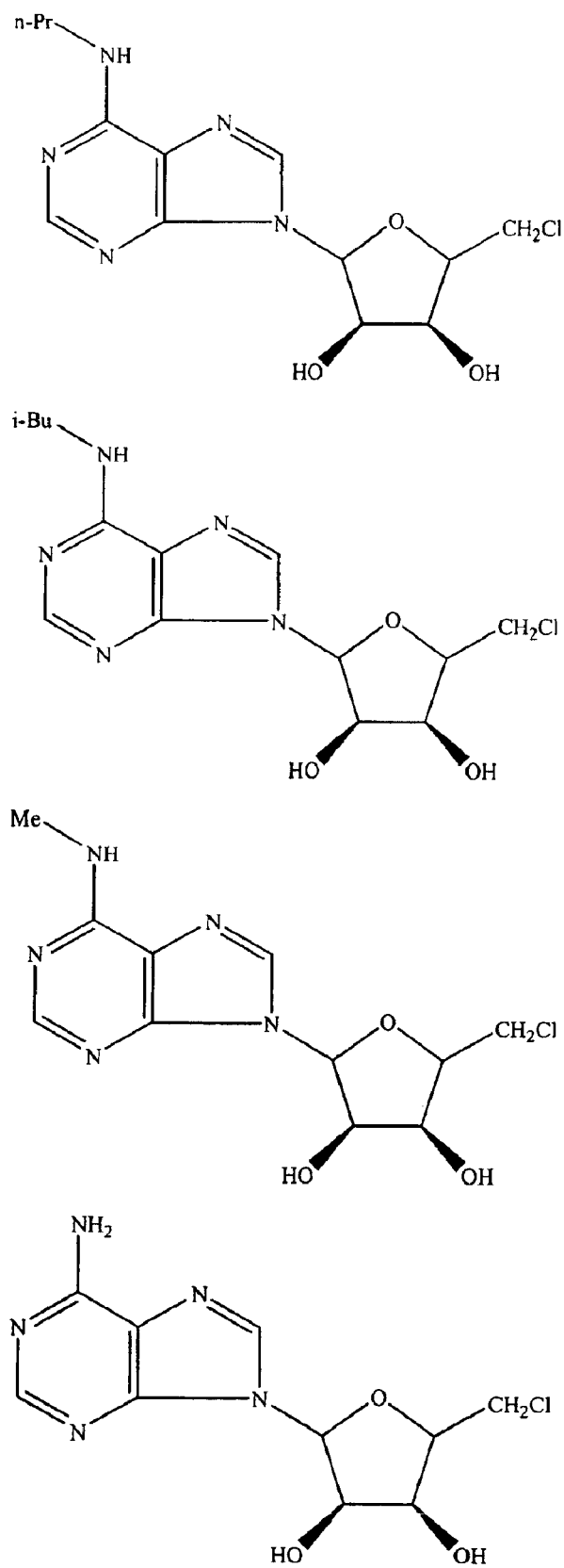
Figure 13O:
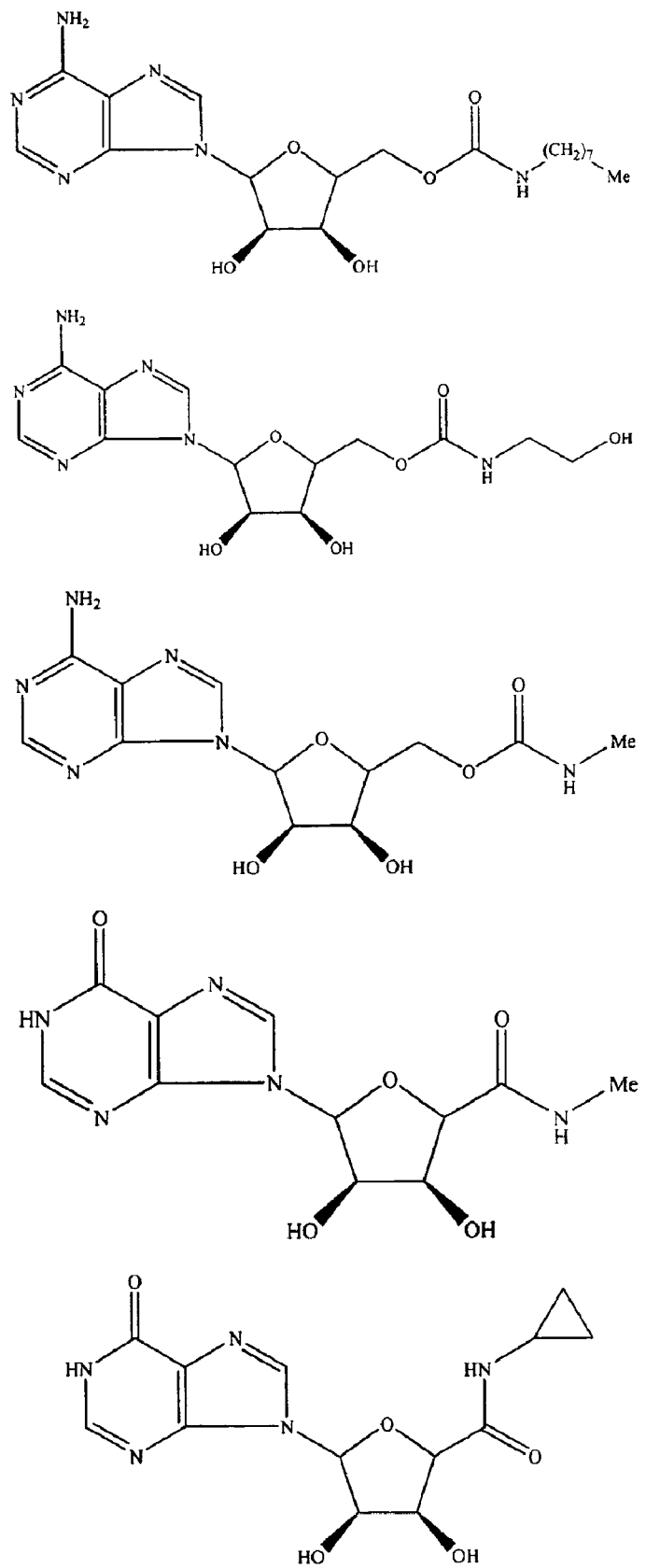
Figure 13P:
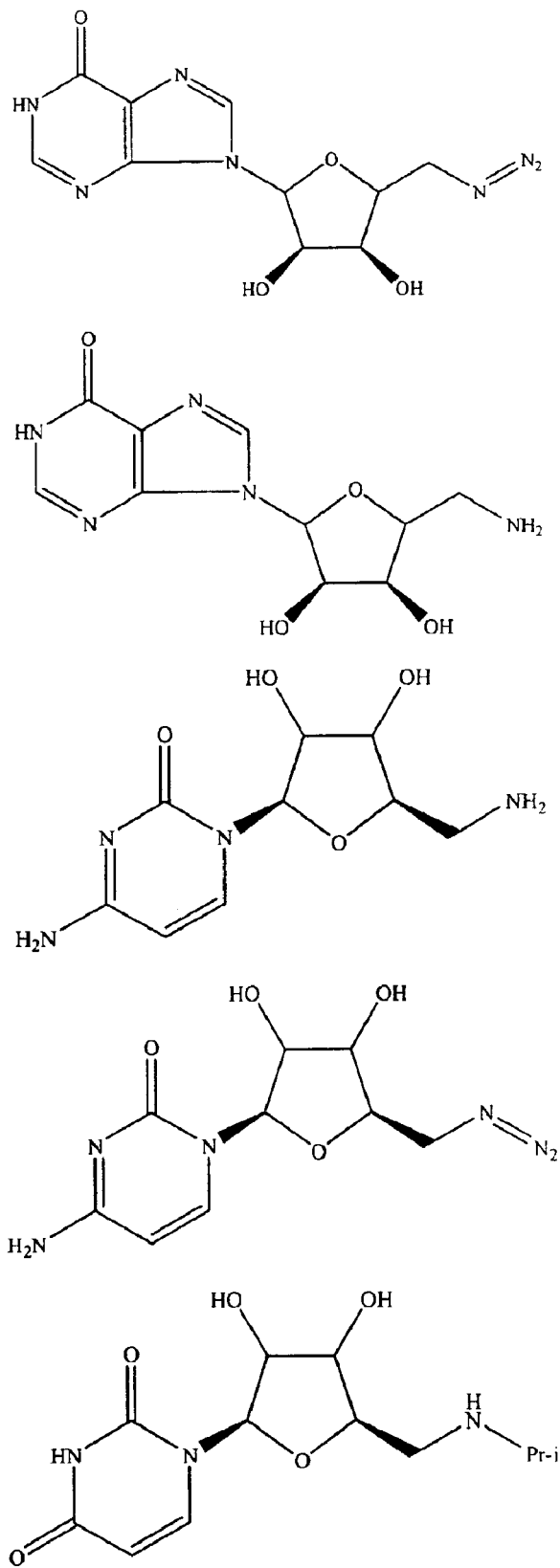
Figure 13Q:
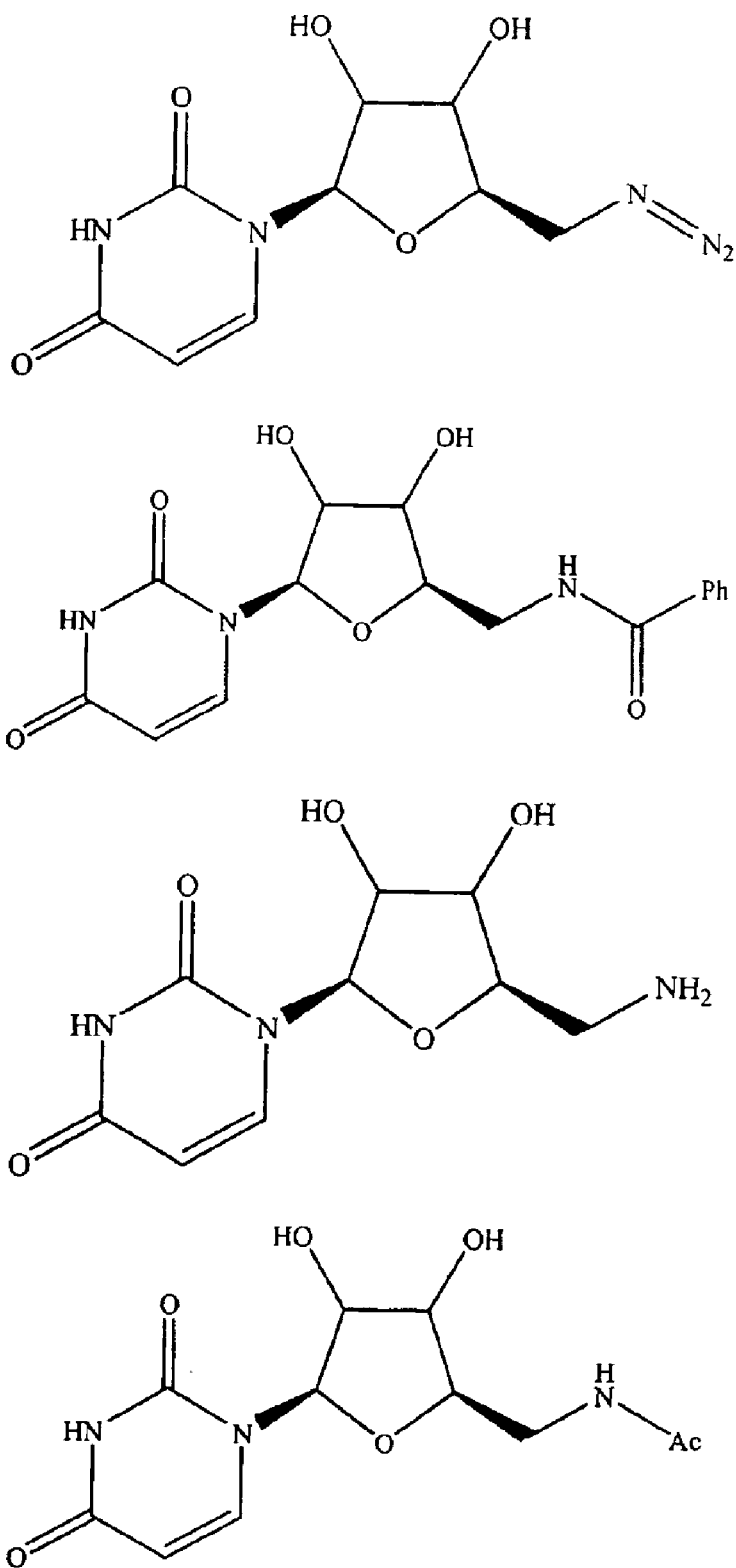
Figure 14A:
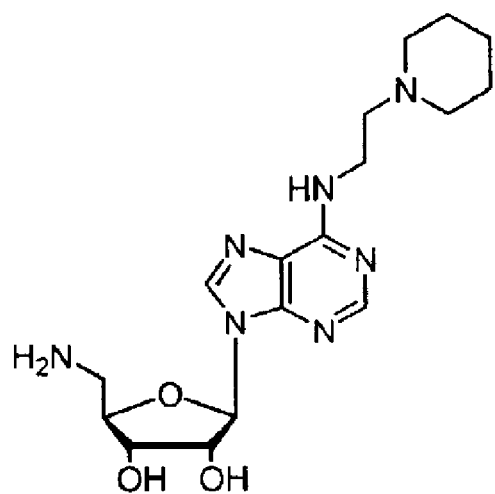
FIGS. 14(A–J) illustrate an exemplary combinatorial library.
Figure 14A:
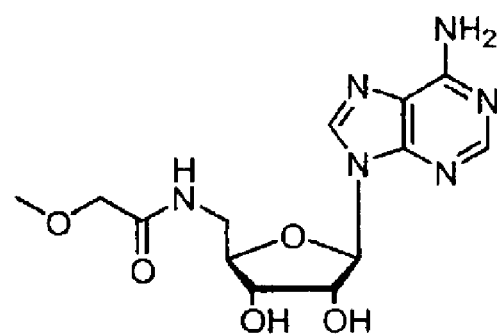
Figure 14A:
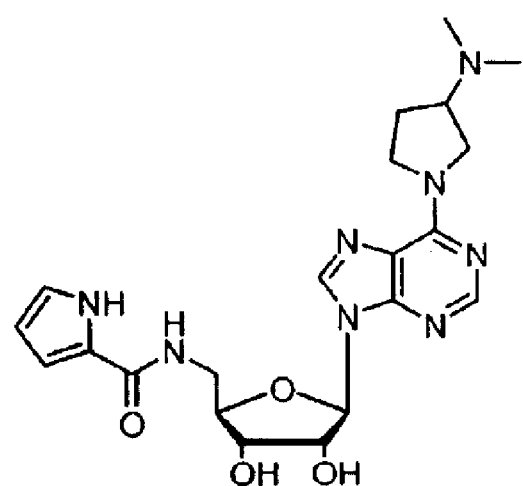
Figure 14B:
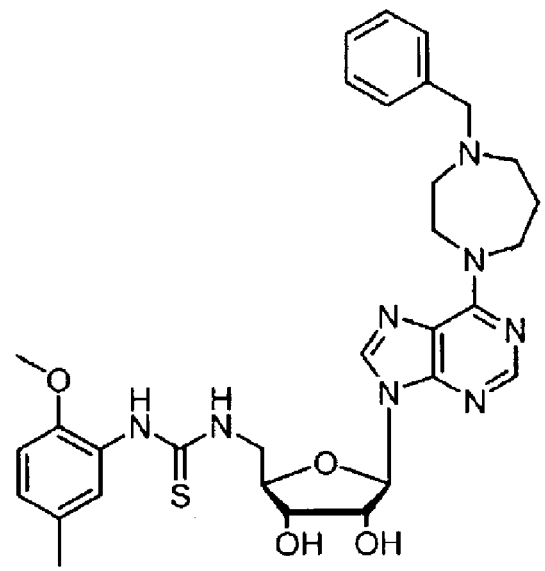
Figure 14B:
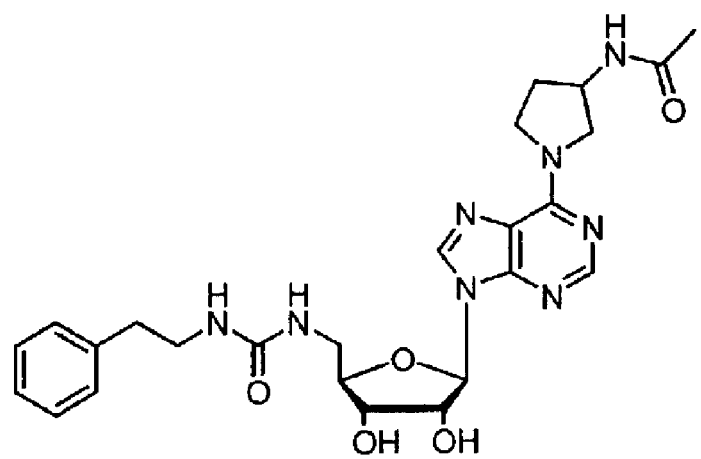
Figure 14B:
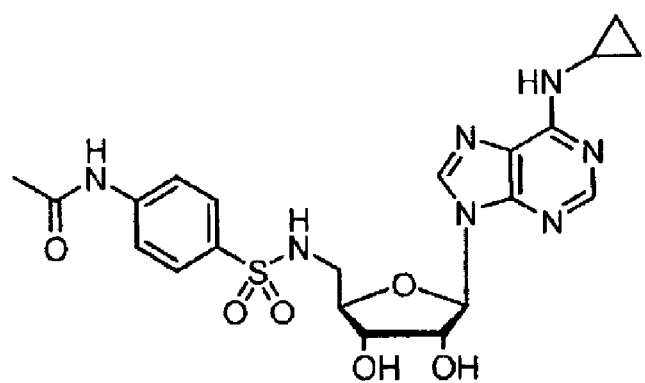
Figure 14C:
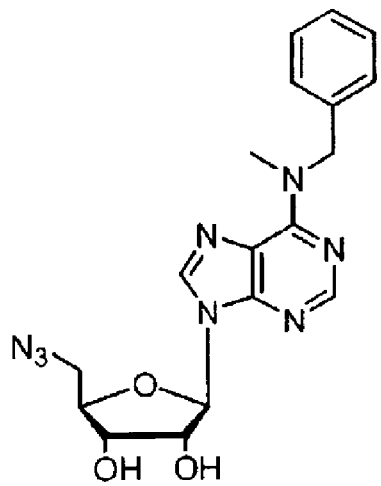
Figure 14C:
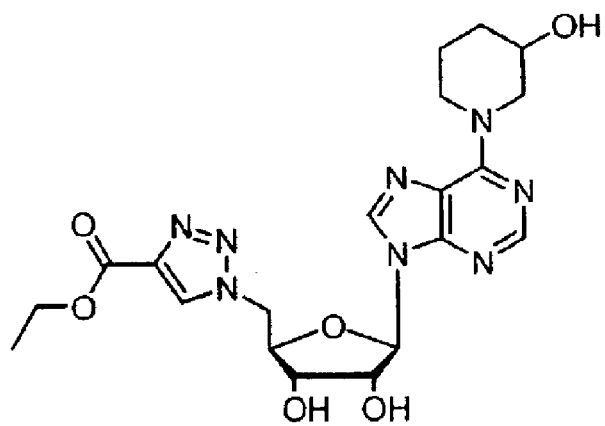
Figure 14C:
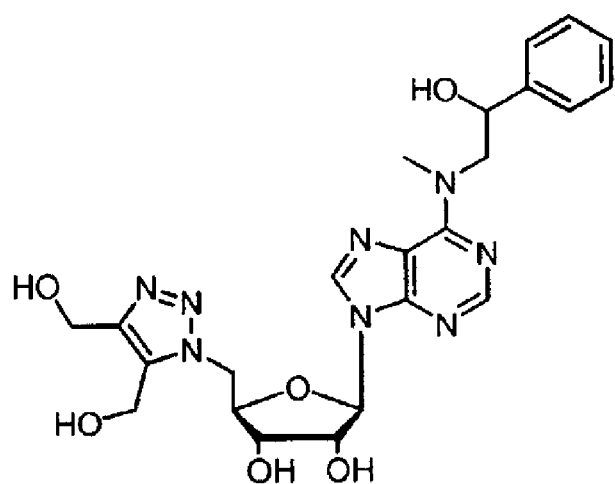
Figure 14D:
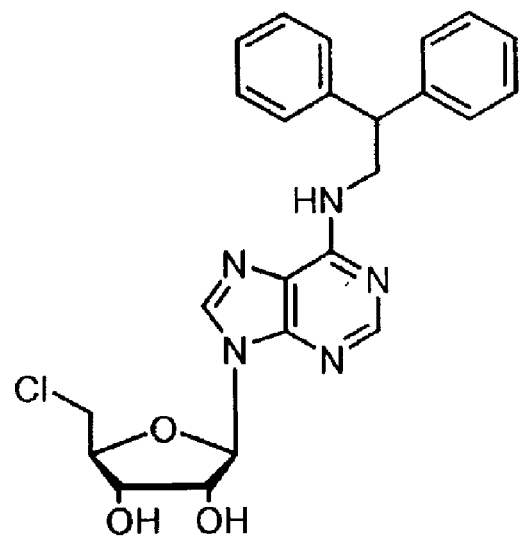
Figure 14D:
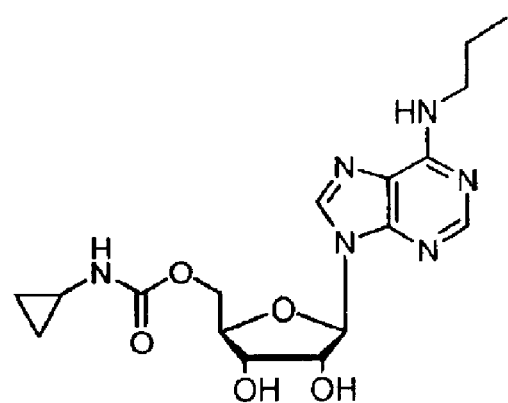
Figure 14D:
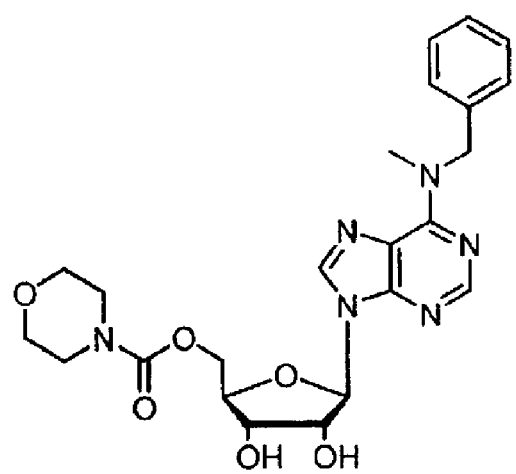
Figure 14E:
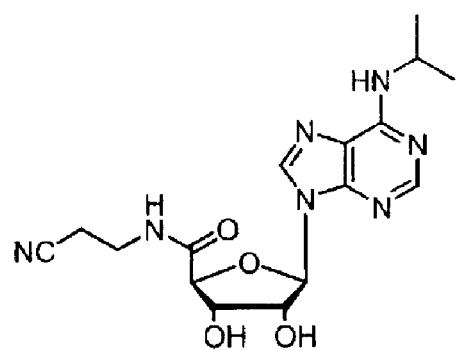
Figure 14E:
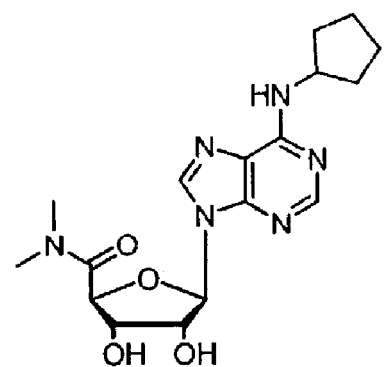
Figure 14E:
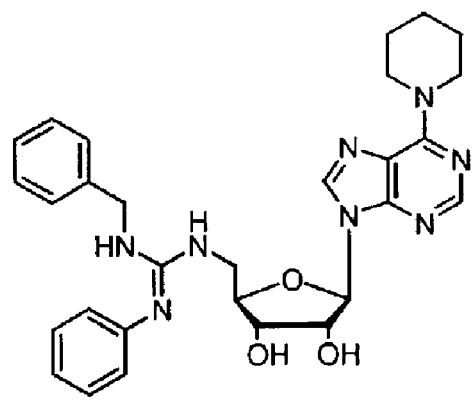
Figure 14E:
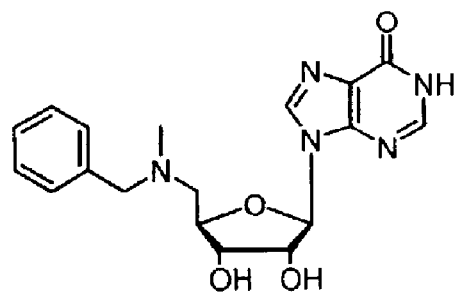
Figure 14F:
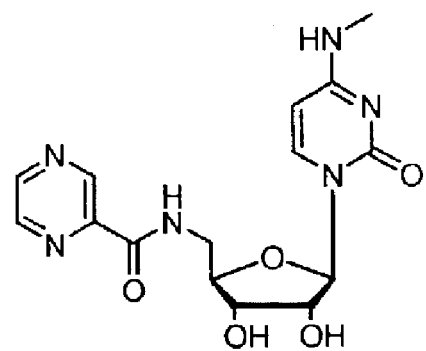
Figure 14F:
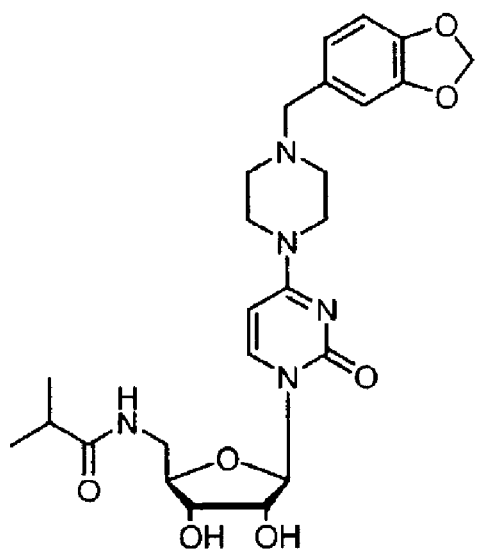
Figure 14F:
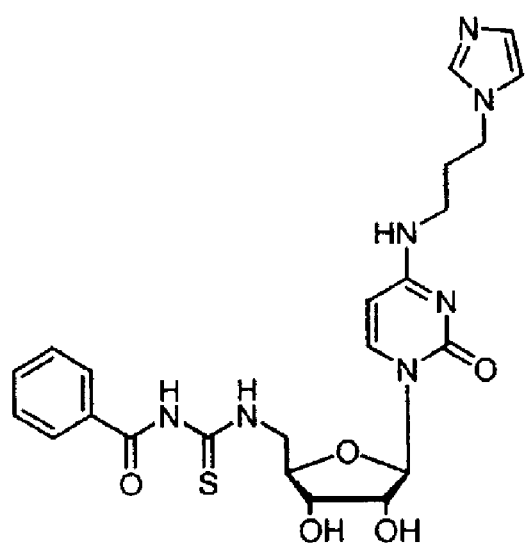
Figure 14G:
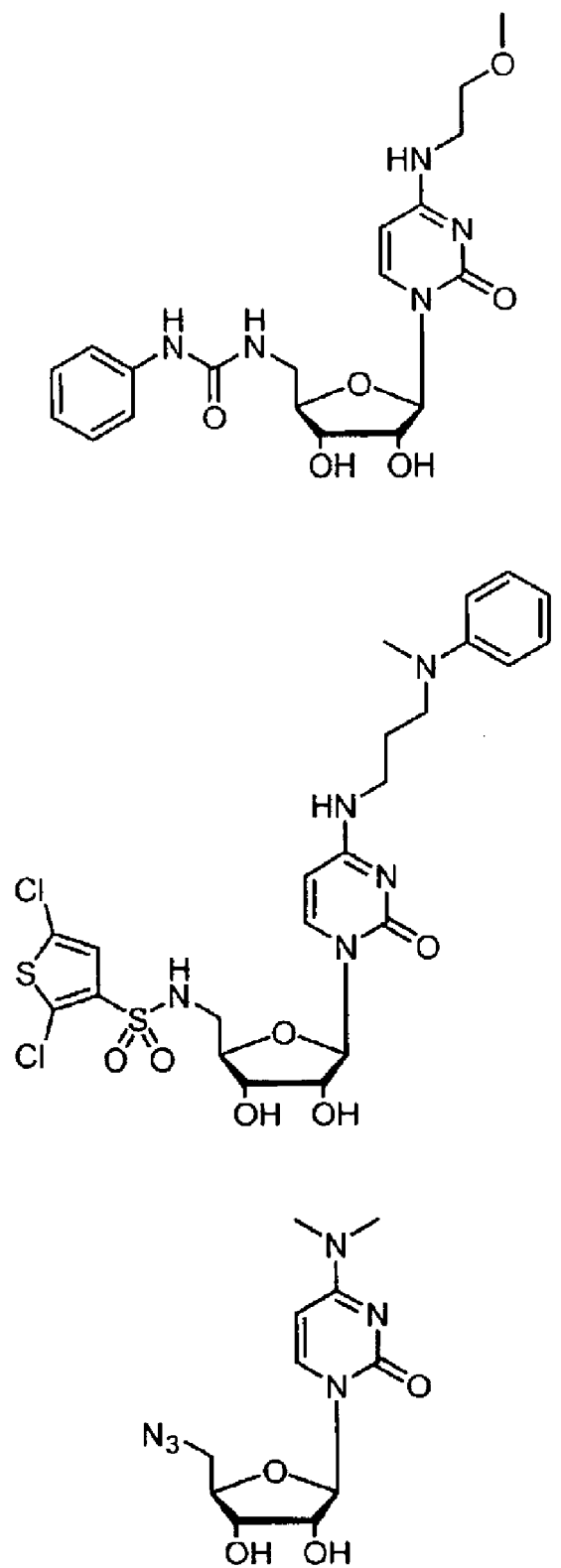
Figure 14H:
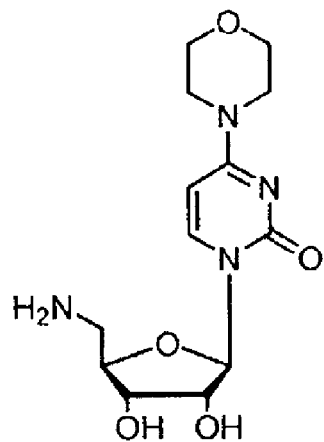
Figure 14H:
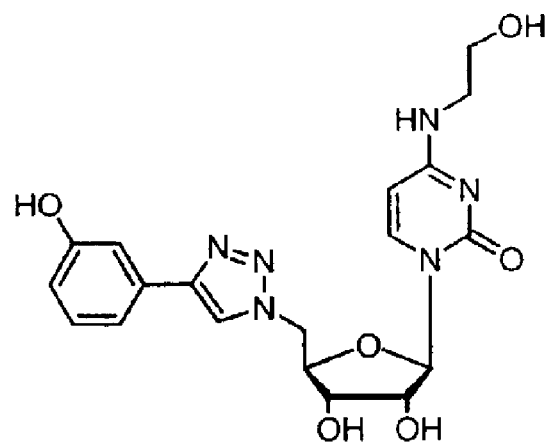
Figure 14H:
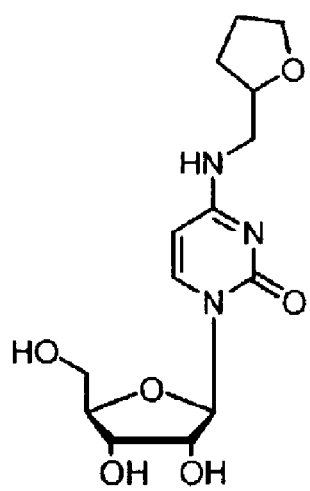
Figure 14I:
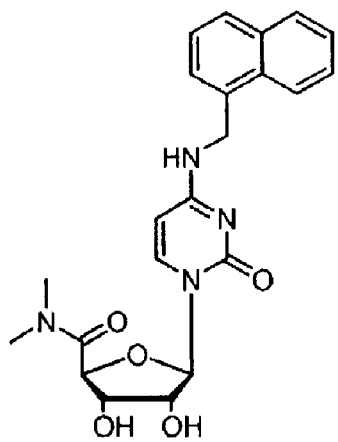
Figure 14I:
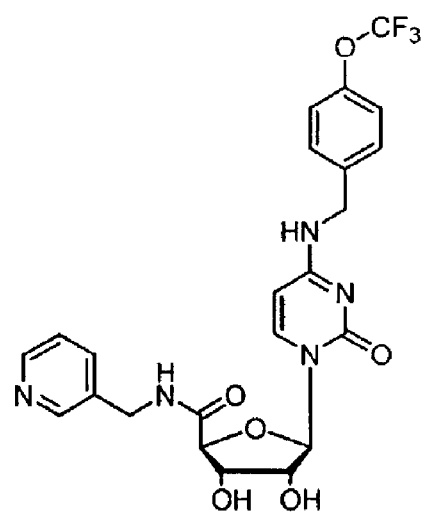
Figure 14I:
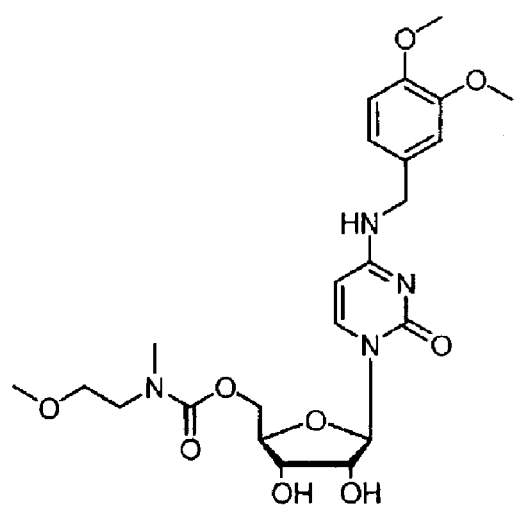
Figure 14J:
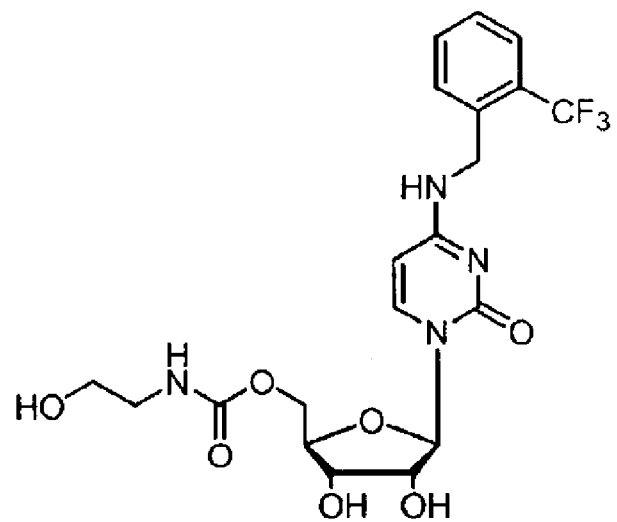
Figure 14J:
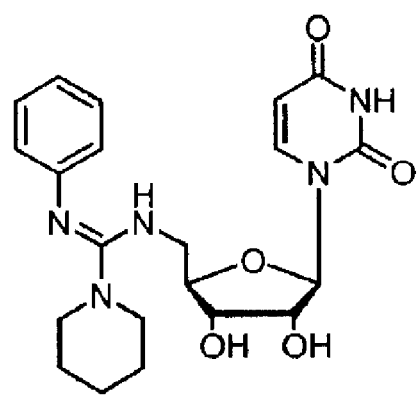
Figure 14J:
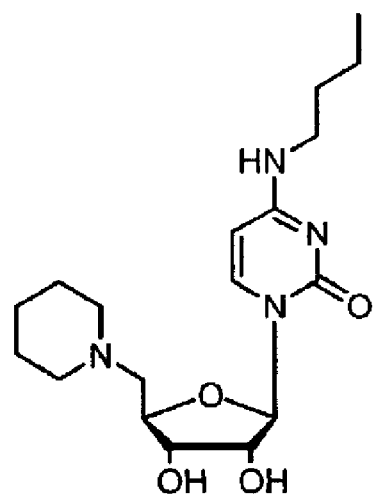

One of skill in the art would recognize that a variety of substituents are useful as the variable base substituent $R^1$ and the variable substituent $R^2$ moieties in FIG. 12. For example, useful $R^1$ substituents include, but are not limited to, those presented in FIGS. 13A–Q and FIGS. 14A–J, such as free amines, aminocycloalkyls, aminoaryls, aminoalkyls, and alkylethers. Likewise, useful $R^2$ substituents include, but are not limited to, those presented in FIGS. 13A–Q and FIGS. 14A–J, such as variably substituted amides, aminoalkyls, azides, and heterocycloalkyls.

Combinatorial Libraries

The present invention provides combinatorial libraries of nucleoside analogs. The libraries can be used as tools for drug discovery; i.e., as a means to discover novel lead compounds by screening the library against a variety of biological targets and to develop structure-activity relationship (SAR) data. In certain aspects, the compounds are agonists or antagonists of therapeutic targets.

The combinatorial libraries of nucleoside analogs of the present invention are either in the solid phase or in the solution phase. When in the solid phase, the libraries are typically bound to a solid support as described above. Typically, the combinatorial libraries of the present invention comprises at least 50 members. In certain embodiments, the combinatorial libraries comprise about to about 50 to about 500 members, more preferably 500 to about 2000 members, and still more preferably about 2000 to about 7000, and in certain instances, the libraries contain about 7000 to about 15,000 members. In other embodiments, the combinatorial libraries comprise at least 15,000 members and as many as 25,000 members.

In another aspect, the present invention provides a library of at least 500 compounds having the formula:

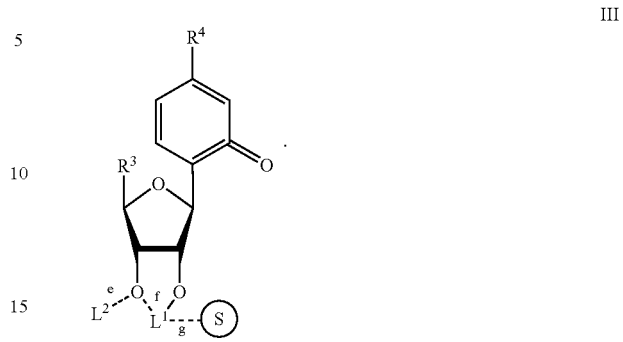

III

In this aspect, the ring substituent $R^3$ is typically selected from $—SR^5$, $—NR^6R^7$, $—NR^8—NR^9R^{10}$, $—NR^{11}—OR^{12}$ or $—OR^{13}$. The substituents $R^5$, $R^6$, $R^7$, $R^8$, $R^9$, $R^{10}$, $R^{11}$, $R^{12}$ and $R^{13}$ are typically selected from hydrogen, an optionally substituted alkyl, an optionally substituted heteroalkyl, an optionally substituted aryl, an optionally substituted heteroaryl, or an optionally substituted heterocycloalkyl.

The substituent $R^4$ is typically selected from:

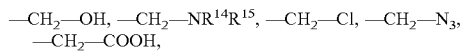

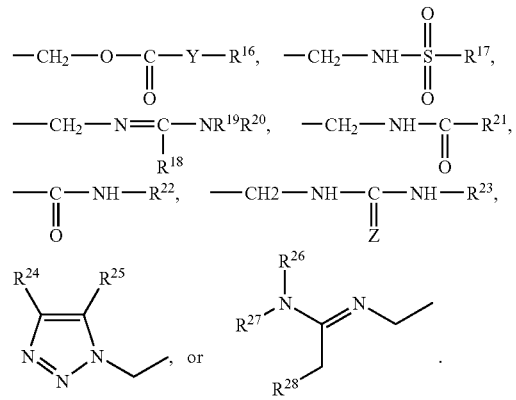

The substituents $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, and $R^{28}$ are typically selected from hydrogen, an optionally substituted alkyl, an optionally substituted heteroalkyl, an optionally substituted aryl, an optionally substituted heteroaryl, or an optionally substituted heterocycloalkyl. The substituent Z that is double bonded to carbon is typically an oxygen or sulfur. The substituent Y is typically an oxygen or a secondary amine.

The dashed bonds denoted by e, f and g are single bonds or absent. The dashed bonds e, f, and g are not all single bonds simultaneously nor all absent simultaneously. Rather, if e is a single bond then f is absent and g is absent. In addition, if e is absent then f is a single bond and g is a single bond.

$L^1$ is a linker moiety or hydrogen. $L^1$ is hydrogen when e is a single bond and $L^1$ is a linker moiety when e is absent.

$L^2$ is hydrogen or absent wherein $L^2$ is hydrogen when e is a single bond and $L^2$ is absent when e absent.

S is an optionally present solid phase. Typically, S is not present when e is a single bond and S is present when e is absent.

In an exemplary embodiment, the present invention provides a library of at least 500 compounds having the formula:

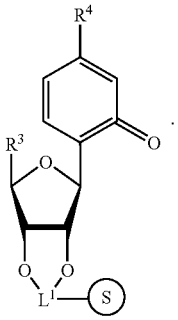

In this exemplary embodiment, the ring substituent $R^3$, the substituent $R^4$, the optionally present solid phase S are as described above. $L^1$, however is limited to a linker moiety in this embodiment. Linker molecules of use in the present invention are described above. In a further embodiment, the linker molecule $L^1$ has the formula:

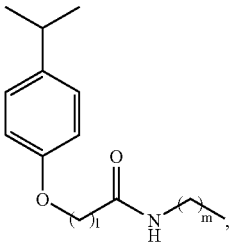

wherein the parenthetical subscripts l and m are integers typically selected from about 1 to about 50.

In another exemplary embodiment, the present invention provides a library of at least 500 compounds having the formula:

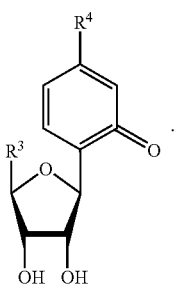

In this exemplary embodiment, the ring substituent $R^3$ and the substituent $R^4$ are as described above.

In another aspect, the present invention provides a library of at least 500 compounds having the formula:

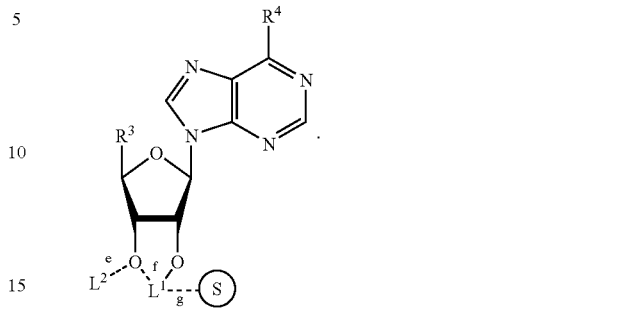

IV

In this aspect, the ring substituent $R^3$ is typically selected from $-SR^5$, $-NR^6R^7$, $-NR^8-NR^9R^{10}$, $-NR^{11}-OR^{12}$ or $-OR^{13}$. The substituents $R^5$, $R^6$, $R^7$, $R^8$, $R^9$, $R^{10}$, $R^{11}$, $R^{12}$ and $R^{13}$ are typically selected from hydrogen, an optionally substituted alkyl, an optionally substituted heteroalkyl, an optionally substituted aryl, an optionally substituted heteroaryl, or an optionally substituted heterocycloalkyl.

The substituent $R^4$ is typically selected from:

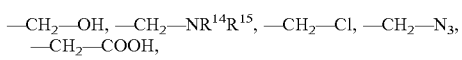

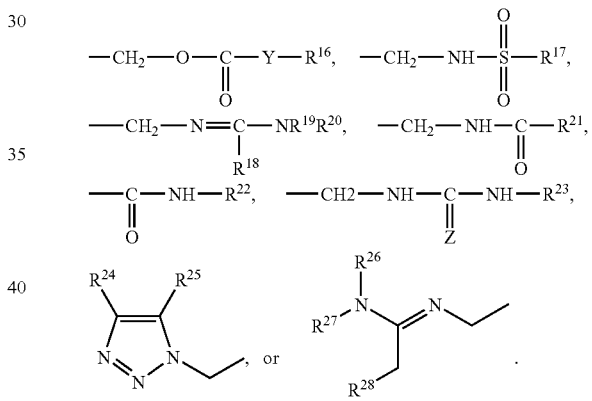

The substituents $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, and $R^{28}$ are typically selected from hydrogen, an optionally substituted alkyl, an optionally substituted heteroalkyl, an optionally substituted aryl, an optionally substituted heteroaryl, or an optionally substituted heterocycloalkyl. The substituent Z that is double bonded to carbon is typically an oxygen or sulfur. The substituent Y is typically an oxygen or a secondary amine.

The dashed bonds denoted by e, f and g are single bonds or absent. The dashed bonds e, f, and g are not all single bonds simultaneously nor all absent simultaneously. Rather, if e is a single bond then f is absent and g is absent. In addition, if e is absent then f is a single bond and g is a single bond.

$L^1$ is a linker moiety or hydrogen. $L^1$ is hydrogen when e is a single bond and $L^1$ is a linker moiety when e is absent.

$L^2$ is hydrogen or absent wherein $L^2$ is hydrogen when e is a single bond and $L^2$ is absent when e absent.

S is an optionally present solid phase. Typically, S is not present when e is a single bond and S is present when e is absent.

In an exemplary embodiment, the present invention provides a library of at least 500 compounds having the formula:

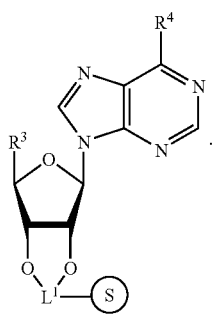

In this exemplary embodiment, the ring substituent $R^3$, the substituent $R^4$, the optionally present solid phase S are as described above. $L^1$, however is limited to a linker moiety in this embodiment. Linker molecules of use in the present invention are described above. In a further embodiment, the linker molecule $L^1$ has the formula:

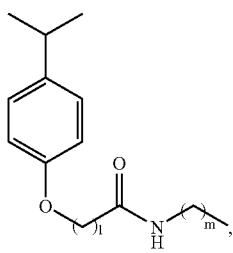

wherein the parenthetical subscripts l and m are integers typically selected from about 1 to about 50.

In another exemplary embodiment, the present invention provides a library of at least 500 compounds having the formula:

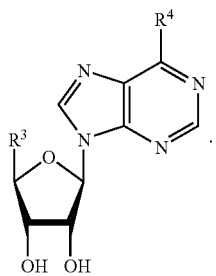

In this exemplary embodiment, the ring substituent $R^3$ and the substituent $R^4$ are as described above.

Methods of Making Combinatorial Libraries

The present invention also provides methods of making combinatorial libraries. Methods for the synthesis of large numbers of diverse compounds that can be screened for various possible physiological or other activities are advantageous. Techniques have been developed in which individual units are added sequentially as part of the chemical synthesis to produce all, or a substantial number, of all the possible compounds which can result from all the different choices possible at each sequential stage of the synthesis. Many diverse compounds are produced by a series of reactions of a multiplicity of synthons in various combinations. Each compound in a combinatorial library results from the reaction of a subset of synthons.

As such, in another aspect, the present invention provides a method of preparing a combinatorial chemistry library typically comprising pyrimidine nucleoside analog compounds. The combinatorial chemistry library of compounds has the formula:

III

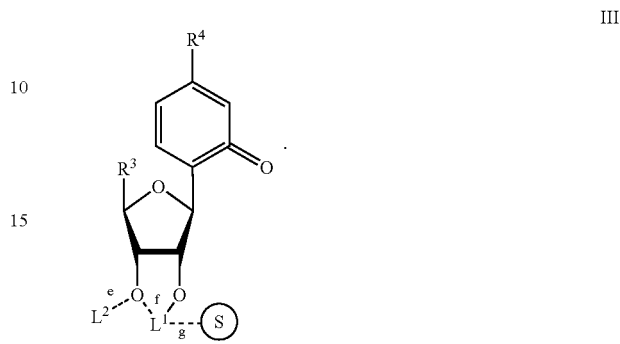

In the method of the present aspect, a combinatorial chemistry intermediate is subjected to at least one diversity generating reaction to form the combinatorial chemistry library of compounds. The chemistry intermediate has the formula:

I

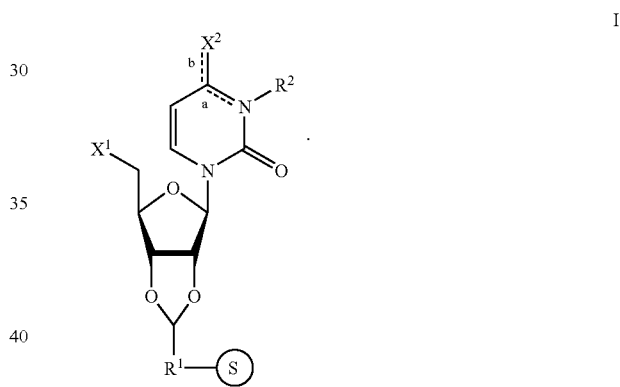

Compounds of Formula I and III comprise the same characteristics and substituent groups as disclosed above.

In another aspect, the present invention provides a method of preparing a combinatorial chemistry library typically comprising purine nucleoside analog compounds. The combinatorial chemistry library of compounds has the formula:

IV

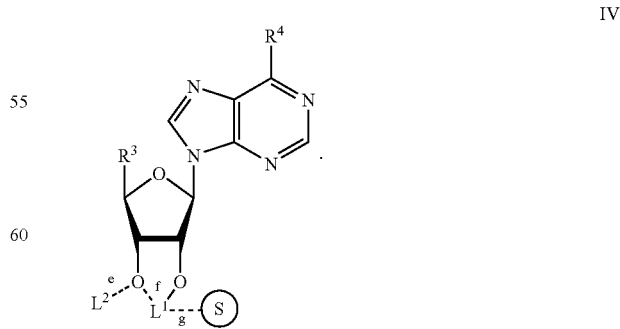

In the method of the present aspect, a combinatorial chemistry intermediate is subjected to at least one diversity generating reaction to form the combinatorial chemistry library of compounds. The chemistry intermediate has the formula:

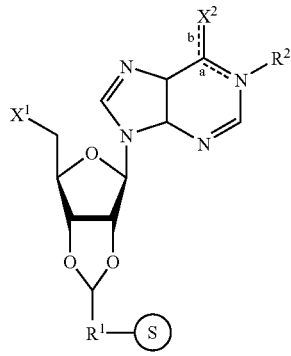

Compounds of Formula I, II, III and IV comprise the same characteristics and substituent groups as disclosed above.

A diversity generating step is defined above (see, e.g., Definitions Section and Exemplary Schemes 3–8). In an exemplary embodiment, a diversity generating reaction comprises contacting compounds of Formulae I or II with a reagent to produce chemical diversification. The reagent is typically reactive to the 5'-substituent $X^1$ or the ring substituent $X^2$ of the compounds of Formulae I or II. The final library of compounds formed by a diversity generating reaction or reactions is within the disclosed library of compounds described above for compounds of Formulae III or IV. Diversity generating reagents are well known in the art. Those of skill in the art will recognize that a variety of reagents may be used to react with the 5'-substituent $X^1$ or the ring substituent $X^2$ of compounds of Formulae I or II to produce a library of compounds within the scope of compounds of Formulae III or IV. Exemplary diversity generating reactions are presented above (see, Exemplary Syntheses 3–8 above).

Solid supports upon which the combinatorial syntheses of the present invention are performed are described above.

Diversity generating reaction are typically conducted in parallel. Parallel synthetic reactions are defined above (see, Definitions section). As will be appreciated by those of skill in the art, the process of library formation and parallel synthesis can be carried out in a number of formats. For example, preparation of the combinatorial libraries can be by the "split resin approach." The split resin approach is described by, for example, Rutter et al., U.S. Pat. No. 5,010,175, Simon et al., WO PCT 91/19735, and Gallop et al., *J. Med. Chem.*, 37: 1233–1251 (1994), all of which are incorporated herein by reference.

In an exemplary embodiment, the parallel synthesis is conducted using a macroporous (macroreticular) polystyrene based resin. In another exemplary embodiment, Nanokan technology is used to perform the parallel synthesis wherein prior to each diversity generating step, the resin aliquots are encapsulated in two dimensional bar-coded microreactors (see, e.g., Nicolaou et al., *Am. Chem. Soc.* 122: 9954–9967 (2000)). Small quantities are traced into discrete wells of mirotiter plates through an automated sorting procedure for high throughput purification applications.

The libraries of the present invention may be solution phase or solid phase. To form a solution phase library, the solid phase library is contacted with a cleavage agent. To produce a solid phase library, the solid phase library is not contacted with a cleavage agent. Thus, contacting the libraries of Formulae III and IV with a cleaving agent is optional.

In an exemplary embodiment, the libraries of Formulae III and IV are contacted with a cleaving reagent to form libraries having the formalae:

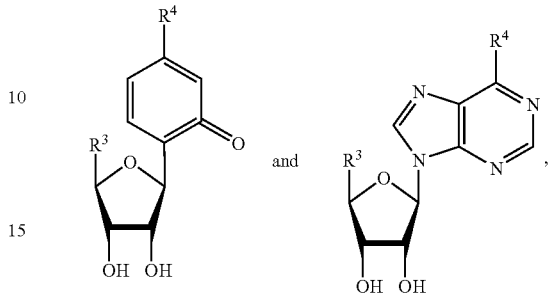

In this exemplary embodiment, the ring substituent $R^3$ and the substituent $R^4$ are as described above fro the compounds of Formulae III and IV.

Methods of cleaving compounds from the solid support with cleavage agents to form solution phase compounds are well known in the art. One skilled in the art would realize that the appropriate cleavage agent depends upon the linker moiety used. Linker moieties useful in the present invention are disclosed above (see, e.g., Definitions Section and Compounds Section). Thus, both acidic and basic cleavage agents are useful in the present invention. In an exemplary embodiment, mild acidic conditions are used to cleave the solid phase compounds of the present invention from the solid support. In another exemplary embodiment, TFA is the acidic cleavage agent. In a another exemplary embodiment, 5% TFA is used to cleave the solid phase compounds of the present invention from the solid support.

Methods of Screening Combinatorial Libraries

The present invention provides methods of using the combinatorial library of Formulae III or IV in assays to discover biologically active compounds or ligands. Thus, another aspect of the invention is a method for identifying compounds having a desired characteristic, which comprises synthesizing a combinatorial library of Formulae III or IV and testing the library, either attached to or detached from the solid phase, in an assay which identifies compounds having the desired characteristic. Typically, the desired characteristic of the present invention is agonism of a purine receptor.

Thus, in another aspect, the present invention provides a method of screening a library of compounds for an agonist of a purine receptor, the method comprising:
  (i) preparing a library of compounds of Formula III; and
  (ii) screening the library by contacting the purine receptor with the library.

In another aspect, the present invention provides a method of screening a library of compounds for an agonist of a purine receptor, the method comprising:
  (i) preparing a library of compounds of Formula IV; and
  (ii) screening the library by contacting the purine receptor with the library.

In an exemplary embodiment, the purine receptors is a P1 or P2 purine receptor. In another exemplary embodiment, the purine receptor is an $A_1$, $A_{2A}$, $A_{2B}$, or A3 purine receptor.

A further aspect of the present invention is determining the structure of any compound identified as a modulator. It is within the scope of the present invention that chemical structures of compounds identified as having a desired characteristic can be determined by deconvolution of the library (see, Smith et al., *Bio. Med. Chem. Lett.* 4: 2821 (1994); Kurth et al., *J. Org. Chem.* 59: 5862 (1994); Murphy et al., *J. Am. Chem. Soc.* 117: 7029 (1995); Campell et al., *J. Am. Chem. Soc.* 118: 5381 (1995); and Erb et al., *Proc. Natl. Acad. Sci.* USA 91: 11422 (1994)). In addition, deconvolution procedures can be verified by analysis of the cleaved compound, such as by mass spectrometry.

Exemplary agonists of Formulae III and IV are set forth in FIGS. 13A–Q and FIGS. 14A–J.

EXAMPLES

General Experimental Details

Melting points were taken on a Thomas Hoover Uni-Melt apparatus and are uncorrected. Nuclear magnetic resonance (NMR) spectra were obtained at 400 MHz with a Bruker DPX-400 instrument. The chemical shift values are reported in parts per million (ppm) relative to tetramethylsilane as an internal standard. Multiplicity, coupling constants and integrations are listed in brackets. Infrared (IR) spectra were obtained on a Nicolet AVATAR 360 FT-IR E.S.P. spectrophotometer. On bead conversions were monitored by on-bead IR, by cleavage followed by reverse phase liquid chromatography coupled with mass spectrometry (LC-MS) analysis (Agilent Series 1100), or by standard staining tests, if applicable. The purity of final compounds was determined using LC-MS analysis together with ultraviolet (UV) trace analysis at 220, 255 and 280 nm. Thin-layer chromatography was performed on Merck (EM Science) Silica gel F254 sheets. Materials obtained from commercial suppliers were used without purification. 6-Chloroinosine 4 (FIG. 5) was obtained from General Intermediates of Canada, Inc. The loading and directed sorting of Irori nanokan microreactors was performed at Irori (Discovery Partners International). To ensure proper solvent and reagent diffusion, the nanokan microreactors were short-time evacuated ("burped") for 1 min prior to the reactions and washing steps using a Labconco vacuum desiccator cabinet (Model No. 55300-00).

1. Synthesis of FIG. 4 Compounds

1.1 Synthesis of 6-(4-Formyl-phenoxy)-hexanoic acid ethyl ester 3

A mixture of 4-hydroxybenzaldehyde 1 (3, 0.60 kg, 4.91 mol), ethyl-6-bromohexanoate 2 (4, 1.10 kg, 4.91 mol), and $K_2CO_3$ (1.36 kg, 9.83 mol) in DMF (2 L) was stirred at 50° C. for 20 h. The mixture was filtered to remove remaining $K_2CO_3$. The resulting solution was concentrated in vacuo, diluted with EtOAc (3 L) and subsequently washed with saturated aqueous NaCl (3×1.5 L). The organic layer was dried ($MgSO_4$), filtered and concentrated in vacuo to give an off white solid (3, 1.23 kg, 4.66 mol, 95%) with no need for further purification: M.p.: 33–35 ° C. $^1$H NMR (400 MHz, $CDCl_3$) δ=9.87 (s, $^1$H), 7.81 (d, J=8.7, 2H), 6.97 (d, J=8.7, 2H), 4.12 (q, J=7.1, 2H), 4.04 (t, J=6.4, 2H), 2.33 (t, J=7.4, 2H), 1.82 (m, 2H), 1.69 (m, 2H), 1.53 (m, 2H), 1.25 (t, J=7.1, 3H); $^{13}$C NMR (400 MHz, $CDCl_3$) δ=191.0, 173.7, 164.3, 132.1 (2C), 130.1, 114.9 (2C), 68.3, 60.5, 34.4, 29.0, 25.8, 24.8, 14.4; IR (film) ν=2941, 1719, 1688, 1595, 1579, 1509, 1466, 1392, 1307, 1252, 1213, 1155, 1108, 1030, 999, 832 cm−1; HRMS (MALDI-FTMS) m/z 287.1254 (287.1254 calculated for $C_{15}H_{20}O_4Na$, (M+Na)+).

1.2 Synthesis of 6-(4-Dimethoxymethyl-phenoxy)-hexanoic acid ethyl ester 4

A mixture of 3 (424 g, 1.60 mol), trimethylorthoformate (0.37 L, 3.40 mol) and p-toluenesulfonic acid monohydrate (15 g, 79 mmol) in MeOH (1 L) was stirred for 5 h at room temperature. Triethylamine (11 mL, 79 mmol) was added, the resulting solution was concentrated in vacuo, diluted with EtOAc (2 L) and subsequently washed with $H_2O$ (2×1 L) and saturated aqueous NaCl (1×1 L). The organic layer was dried ($MgSO_4$), filtered and concentrated in vacuo to yield an amber liquid (4, 481 g, 1.55 mol, 97%) with no need for further purification: $^1$H-NMR (400 MHz, $CDCl_3$) δ=7.33 (d, J=8.7, 2H), 6.97 (d, J=8.7, 2H), 5.33 (s, 1H), 4.11 (q, J=7.1, 2H), 3.95 (t, J=6.4, 2H), 3.29 (s, 6H), 2.32 (t, J=7.4, 2H), 1.79 (m, 2H), 1.69 (m, 2H), 1.49 (m, 2H), 1.24 (t, J=7.1, 3H); $^{13}$C-NMR (400 MHz, $CDCl_3$) δ=173.7, 159.3, 130.4, 128.0 (2C), 114.2 (2C), 103.2, 67.8, 60.4, 52.7 (2C), 34.4, 29.1, 25.8, 24.8, 14.4; IR(film) ν=2937, 1723, 1610, 1513, 1241, 1171, 1104, 1046, 980, 828 cm−1; HRMS (MALDI-FTMS) not detectable due to instability; detected: m/z 287.1254 (287.1252 calculated for parent aldehyde 3 $C_{17}H_{27}O_5Na$, (M+Na)+).

1.3 Synthesis of 6-{4-(4-(2,4-Dioxo-3,4-dihydro-2H-pyrimidin-1-yl)-6-hydroxymethyl-tetrahydro-furo(3,4-d)(1,3)dioxol-2-yl)-phenoxy}-hexanoic acid ethyl ester 6

Uridine 5 (7, 50 g, 0.21 mol) together with 4 (70 g, 0.23 mol) was dissolved in DMF (150 mL). p-Toluenesulfonic acid monohydrate (3.8 g, 20 mmol) was added, the mixture was placed on a Buechi R-134 rotavapor and agitated under reduced pressure (70 mbar) at 50° C. for 15 h. The mixture was then neutralized with triethylamine (2.8 ml, 20 mmol) and subsequently concentrated in vacuo. The resulting residue was suspended in EtOAc (400 mL), filtered and washed with 1:1 EtOAc/$H_2O$ (400 mL), $H_2O$ (2×200 mL), 1:1 $H_2O$/$Et_2O$ (200 mL) and $Et_2O$ (2×200 mL) to give a colorless solid as a mixture of 2 diastereomers (6, 77 g, 0.16 mol, 76%). Upon recrystallisation from EtOH/EtOAc one of the diastereomers exclusively crystallized: M.p.: 176–178° C.; $^1$H-NMR (400 MHz, $(CD_3)_2SO_3$) δ=11.38 (s, 1H), 7.82 (d, J=8.1, 1H), 7.42 (d, J8.6, 2H), 6.95 (d, J=8.6, 2H), 5.94 (s, 1H), 5.90 (s, 1H), 5.64 (d, J=8.1, 1H), 5.10 (t, J=5.2, 1H), 4.99 (m, 1H), 4.82 (m, 1H), 4.23 (m, 1H), 4.04 (q, J=7.1, 2H), 3.97 (t, J=6.3, 2H), 3.60 (m, 2H), 2.30 (t, J=7.4, 2H), 1.71 (m, 2H), 1.58 (m, 2H), 1.41 (m, 2H), 1.16 (t, J=7.1, 3H); $^{13}$C-NMR (400 MHz, (CD3)2SO) δ=172.8, 163.2, 159.7, 150.3, 142.1, 128.4 (2C), 128.0, 114.2 (2C), 106.5, 101.7, 91.3, 86.4, 84.2, 81.6, 67.4, 61.3, 59.6, 33.4, 28.3, 25.0, 24.2, 14.1; IR (film) ν=3467, 2933, 1692, 1677, 1248, 1116, 1077, 828; HRMS (MALDI-FTMS) m/z 513.1851 (513.1849 calculated for $C_{24}H_{30}N_2O_9Na$ (M+Na)+).

1.4 Synthesis of 6-{4-(4-Azidomethyl-6-(2,4-dioxo-3,4-dihydro-2H-pyrimidin-1-yl)-tetrahydro-furo(3,4-d)(1,3)dioxol-2-yl)-phenoxy}-hexanoic acid ethyl ester 7

A 3 L round bottom flask containing the uridine derivative 6 (99 g, 0.20 mol), DCM (250 mL) and pyridine (250 mL) was placed in a chilled water bath (4° C.). Methanesulfonyl chloride (19.1 mL, 0.25 mol) was added over a period of 15 min, the solution was allowed to warm to room temperature and left to stir for 18 h. The mixture was then concentrated in vacuo, diluted with EtOAc (1.75 L), washed with $H_2O$ (3×1 L), dried ($MgSO_4$), filtered and concentrated in vacuo to yield a colorless oil (107.0 g, 188 mmol, 93%). as a mixture of two diastereomers. Sodium azide ($NaN_3$, 11.5 g, 177 mmol) was added to the oil (50 g, 88 mmol) in DMF (200 mL) and stirred at 45° C. for 18 h. The resulting mixture was concentrated in vacuo, diluted with EtOAc (500 mL), washed with saturated aqueous NaCl (2×500 mL) and $H_2O$ (2×500 mL), dried ($MgSO_4$), filtered and concentrated in vacuo to yield a colorless foam (7, 40.0 g, 77.6 mmol, 88%) as a mixture of two diastereomers: $^1$H-NMR (400 MHz, CDCl$_3$) δ=9.60 (s, 1H, 1H'), 7.44 (d, J=8.7, 2H), 7.39 (d, J=8.7, 2H), 7.31 (d, J=8.0, 1H, 1H'), 6.93 (d, J=8.7, 2H), 6.91 (d, J=8.7, 2H'), 6.04 (s, 1H'), 5.96 (s, 1H), 5.80 (d, J=8.0, 1H, 1H'), 5.77 (s, 1H), 5.72 (s, 1H'), 5.17–4.92 (m, 2H, 2H'), 4.44 (m, 1H), 4.34 (m, 1H'), 4.15 (m, 2H, 2H'), 3.99 (q, J=6.3, 2H, 2H'), 3.69 (m, 2H, 2H'), 2.36 (m, 2H, 2H'), 1.82 (m, 2H, 2H'), 1.72 (m, 2H, 2H'), 1.52 (m, 2H, 2H'), 1.27 (m, 3H, 3H') $^{13}$C-NMR (400 MHz, CDCl$_3$) δ=174.0, 174.0, 164.5, 163.3, 160.9, 160.8, 150.3, 150.3, 143.0, 142.8, 128.6 (2C), 128.5 (2C), 127.7, 127.6, 115.1 (2C), 114.9 (2C), 108.5, 104.7, 103.5, 103.4, 95.2, 95.1, 86.3, 85.5, 84.0, 83.9, 82.4, 81.8, 68.5, 68.1, 60.7, 60.7, 52.9, 52.7, 34.6, 34.4, 29.3, 29.1, 26.0, 26.0, 25.1, 25.0, 14.7, 14.7; IR (film) ν=3198, 2938, 2097, 1684, 1245, 1069, 832, 809; HRMS (MALDI-FTMS) m/z 538.1916 (538.1908 calculated for C$_{24}$H$_{29}$N$_5$O$_8$Na (M+Na)+).

1.5 Synthesis of 6-{4-(4-Azidomethyl-6-(2,4-dioxo-3,4-dihydro-2H-pyrimidin-1-yl)-tetrahydro-furo(3,4-d)(1,3)dioxol-2-yl)-phenoxy}-hexanoic acid 8

A solution of sodium hydroxide (NaOH, 20.8 g, 522 mmol) in H$_2$O (125 mL) was added to a suspension of 7 (89.8 g, 174 mmol) in EtOH (400 mL) and stirred for 4 h at room temperature. The solvent was removed and the resulting residue was diluted with H$_2$O (300 mL). The suspension was then treated dropwise with 1M aqueous HCl (522 mmol, 522 mL) to afford a white precipitate, which was subsequently partitioned with EtOAc (1.5 L). The organic layer was then washed with H$_2$O (2×1 L), dried (MgSO$_4$), filtered and concentrated in vacuo to give a white foam (8, 80.2 g, 164 mmol, 95%) as a mixture of two diastereomers: $^1$H-NMR (400 MHz, (CD$_3$)$_2$SO$_3$) δ=12.01 (s, 1H, 1H'), 11.49 (s, 1H, 1H'), 7.78 (d, J=8.0, 1H), 7.74 (d, J=8.0, 1H'), 7.43 (d, J=8.5, 2H), 7.37 (d, J 8.5, 2H'), 6.96 (d, J=8.5, 2H), 6.93 (d, J=8.5, 2H'), 6.07 (s, 1H'), 5.93 (s, 1H), 5.91 (s, 1H, 1H'), 5.67 (d, J=8.0, 1H), 5.66 (d, J=8.0, 1H'), 5.20–4.81 (m, 2H, 2H'), 4.31 (m, 1H, 1H'), 3.96 (m, 2H, 2H'), 3.62 (m, 2H, 2H'), 2.22 (m, 2H, 2H'), 1.70 (m, 2H, 2H'), 1.54 (m, 2H, 2H'), 1.41 (m, 2H, 2H'); $^{13}$C-NMR (400 MHz, (CD$_3$)$_2$SO$_3$) δ=175.3, 175.3, 164.1, 164.0, 160.7, 160.6, 151.2, 151.2, 144.3, 143.7, 129.3 (2C), 129.3 (2C), 128.6, 128.6, 115.1 (2C), 115.0 (2C), 107.6, 103.5, 103.1, 102.8, 93.5, 92.5, 85.9, 85.1, 83.2, 82.8, 82.6, 81.5, 68.3, 68.3, 52.7, 52.5, 34.5, 34.5, 29.2, 29.1, 26.0, 25.9, 25.1, 25.1; IR (film) ν=3354, 3183, 2941, 2101, 1684, 1245, 1069, 1050, 1023, 995, 824; HRMS (MALDI-FTMS) mn/z 510.1600 (510.1595 calculated for C$_{22}$H$_{25}$N$_5$O$_8$Na (M+Na)+).

1.6 Synthesis of 6-{4-(4-(2,4-Dioxo-3,4-dihydro-2H-pyrimidin-1-yl)-6-hydroxymethyl-tetrahydro-furo(3,4-d)(1,3)dioxol-2-yl)-phenoxy}-hexanoic acid 15

A solution of NaOH (12.6 g, 315 mmol) in H$_2$O (100 mL) was added to a suspension of 6 (50 g, 102 mmol) in MeOH (750 mL) and stirred for 8 h at room temperature. Approximately half of the solvent was removed in vacuo and the remainder was treated dropwise with 1 M aqueous HCl (315 mmol, 315 mL). The white precipitate was filtered, washed with H$_2$O (2×200 mL) and Et$_2$O (3×200 mL) and dried in vacuo to afford a white powder (15, 46.7 g, 100 mmol, 99%) as a mixture of two diastereomers: M.p.: 158–160° C.; $^1$H-NMR (400 MHz, (CD$_3$)$_2$SO$_3$) δ=11.95 (s, 1H, 1H'), 11.38 (s, 1H, 1H'), 7.85 (d, J=8.0, 1H), 7.77 (d, J=8.0, 1H'), 7.41 (d, J=8.5, 2H), 7.37 (d, J=8.5, 2H'), 6.96 (d, J=8.5, 2H), 6.93 (d, J=8.5, 2H'), 6.04 (s, 1H'), 5.93 (m, 1H, 1H'), 5.90 (s, 1H), 5.64 (d, J=8.0, 1H), 5.63 (d, J=8.0, 1H'), 5.2 (broad, 1H, 1H'), 4.99–4.83 (m, 2H, 2H'), 4.23 (m, 1H), 4.13 (m, 1H'), 3.97 (m, 2H, 2H'), 3.62 (m, 2H, 2H'), 2.20 (m, 2H, 2H'), 1.70 (m, 2H, 2H'), 1.54 (m, 2H, 2H'), 1.41 (m, 2H, 2H'); $^{13}$C -NMR (400 MHz, (CD$_3$)$_2$SO$_3$) δ=176.0, 176.0, 164.1, 164.1, 160.6, 160.5, 151.2, 151.2, 143.0, 143.0, 129.3 (2C), 129.3 (2C), 128.9, 128.9, 115.1 (2C), 115.0 (2C), 107.4, 103.4, 102.8, 102.6, 92.2, 91.3, 87.3, 85.1, 84.8, 83.7, 82.6, 80.8, 68.3, 68.3, 62.2, 62.2, 35.1, 35.1, 29.3, 29.3, 26.1, 26.1, 25.4, 25.4; IR (film) ν=3467, 3132, 2938, 1696, 1677, 1245, 1108, 1077, 1046, 1019, 976, 828, 809; HRMS (MALDI-FTMS) m/z 485.1534 (485.1536 calculated for C$_{22}$H$_{26}$N$_2$O$_9$Na (M+Na)+).

1.7 Synthesis of Resin Bound 5'-azido pyrimidine Scaffold 12

A solution of 8 (66 g, 136 mmol), N-hydroxybenzotriazole (HOBt, 18.4 g, 136 mmol) and diisopropylcarbodiimide (DIC, 17.1 g, 136 mmol) in DMF (500 mL) was added to aminomethyl resin (11, 70 g, 105 mmol) and agitated for 10 h at room temperature. The complete conversion was confirmed by a negative bromophenol blue test. Resin 12 was then washed with DMF (4×500 mL), THF (4×500 mL), DCM (4×500 mL) and MeOH (4×500 mL) and dried in vacuo. IR (on bead) ν=3081w, 3054w, 3023w, 2920m, 2851w, 2097m, 1693s, 1610m, 1511m, 1491m, 1375m, 1243s, 1169m, 1076s, 1024m, 979m, 703s.

1.8 Synthesis of Resin Bound 5'-azido-4-triazolo-pyrimidine Scaffold 14

Phosphorus oxychloride (POCl$_3$, 16.8 mL, 180 mmol) was added over a period of 10 min to a stirred solution of 1,2,4-triazole (13, 62.2 g, 900 mmol) in MeCN (500 mL), upon which a white precipitate formed immediately. Subsequently, triethylamine (TEA, 134 mL, 960 mmol) was added over a period of 10 min. The slurry was then added to resin 12 (68.2 g, 60 mmol) and agitated for 5 h at room temperature. The bright yellow resin was washed with MeCN (3×500 mL), DMF (4×500 mL), THF (4×500 mL), DCM (4×500 mL) and MeCN (4×500 mL) and dried in vacuo. IR (on bead) ν=3082w, 3058w, 3023w, 2926m, 2856w, 2101m, 1680s, 1630w, 1548m, 1509m, 1470m, 1449w, 1400w, 1375m, 1283m, 1248s, 1174w, 1097s, 937m, 700s.

1.9 Synthesis of Resin Bound 5'-hydroxy pyrimidine Scaffold 16

Resin 16 was synthesized according to the procedure for resin bound 5'-azido pyrimidine scaffold 12, except that 5'-hydroxy uridine derivative 15 was used instead of 5'-azido uridine derivative 8. IR (on bead) ν=3082w, 3054w, 3025w, 2920w, 2852w, 1679s, 1652m, 1597s, 1574w, 1508m, 1488m, 1449m, 1309w, 1258s, 1216m, 1161s, 1024w, 697s.

1.10 Resin Bound 5'-acetoxy pyrimidine Scaffold 17

A solution of 4-dimethylaminopyridine (DMAP, 3.6 g, 30 mmol) and acetic anhydride (Ac$_2$O, 10 mL, 100 mmol) in THF (200 mL) was added to resin 16 (22.3 g, 20 mmol) and agitated for 10 h at room temperature. The resin was subsequently washed in 10 min intervals with THF (4×200 mL), DMF (4×200 mL), DCM (4×200 mL), MeOH (4×200 mL) and dried in vacuo. IR (on bead) ν=3085w, 3058w, 3021w, 2920m, 2849w, 1687s, 1613w, 1512m, 1488m, 1457s, 1383w, 1302w, 1242s, 1171w, 1079s, 701s.

1.11 Resin Bound 5'-acetoxy-4-triazolo-pyrimidine Scaffold 18

Resin 18 was synthesized according to the procedure for resin bound 5'-azido-4-triazolo pyrimidine scaffold 14, except that 5'-acetoxy uridine resin 16 was used instead of 5'-azido uridine resin 12. IR (on bead) ν=3120w, 3082w, 3058w, 3021w, 2920m, 2849w, 1738w, 1668s, 1614w, 1543m, 1508s, 1464m, 1453s, 1419w, 1396w, 1374w, 1285s, 1246s, 1164w, 1118m, 1075s, 697s.

2. Synthesis of FIG. 5 Compounds

2.1 6-(4-Dimethoxymethyl-phenoxy)-hexanoic acid allyl ester 3

Sodium hydride (5.0 g, 0.21 mol) was slowly added to allyl alcohol (2, 1.2 L). To this solution the ethyl ester 1 (232 g, 0.78 mmol) was added in allyl alcohol (0.2 L) and stirred for 6 h at room temperature. The reaction mixture was concentrated in vacuo, diluted with EtOAc (1 L) and washed with saturated aqueous NaCl (3×0.5 L). The organic layer was dried (MgSO$_4$), filtered and concentrated in vacuo to yield a yellow liquid (3, 220 g, 0.68 mmol, 88%): $^1$H-NMR (400 MHz, CDCl$_3$) δ=7.33 (d, J=8.2, 2H), 6.90 (d, J=8.2, 2H), 5.94 (m, 1H), 5.32 (s, 1H), 5.31 (d, J=12.3, 1H), 5.22 (d, J=10.4, 1H), 4.58 (m, 2H), 3.97 (m, 2H), 3.29 (s, 6H), 2.39 (m, 2H), 1.79 (m, 2H), 1.69 (m, 2H), 1.52 (m, 2H); $^{13}$C-NMR (400 MHz, (CD3)2SO) δ=175.0, 160.8, 133.9, 131.7, 129.1 (2C), 118.4, 115.2 (2C), 104.7, 68.9, 66.1, 53.2 (2C), 35.0, 30.2, 26.8, 25.9; IR (film) ν=2930, 1735, 1614, 1513, 1353, 1299, 1241, 1167, 1097, 1050, 980, 933, 828; HRMS (MALDI-FTMS) not detectable due to instability; detected: m/z 299.1263 (calculated for parent aldehyde C$_6$H$_{20}$O$_4$Na (M+Na)+ 299.1259).

2.2 6-{4-(4-(6-Chloro-purin-9-yl)-6-hydroxymethyl-tetrahydro-furo(3,4-d)(1,3)dioxol-2-yl)-phenoxy}-hexanoic acid allyl ester 5

A mixture of 6-chloroinosine (4, 32.5 g, 113 mmol) and the acetal linker 3 (47.5 g, 147 mmol) was dissolved in DMF (230 mL). p-Toluenesulfonic acid monohydrate (1.1 g, 5.7 mmol) was added, and the solution was placed on a Buechi R-134 rotavapor and agitated under reduced pressure (70 mbar) at 50° C. for 15 h. The solvent was removed in vacuo, the resulting residue was dissolved in EtOAc (1 L) and neutralized with triethyl amine (0.8 mL, 5.7 mmol). The solution was then washed with saturated aqueous NaCl (3×1 L), H$_2$O (1 L), dried (MgSO$_4$), filtered and concentrated. The resulting residue was taken up in EtOAc and triturated with hexanes, upon which the product precipitated as a white powder (5, 59.3 g, 109 mmol, 96%, mixture of two diastereomers): M.p.: 103–105° C.; $^1$H-NMR (400 MHz, CDCl$_3$) δ=8.78 (s, 1H), 8.77 (s, 1H'), 8.41 (s, 1H), 8.33 (s, 1H'), 7.47 (d, J=8.6 ,2H), 7.37 (d, J=8.6, 2H'), 6.95 (d, J=8.5, 2H), 6.89 (d, J=8.5, 2H'), 6.24 (s, 1H), 6.19 (m, 1H, 1H'), 6.02 (s, 1H'), 5.91 (m, 1H, 1H'), 5.37–5.18 (m, 4H, 4H'), 4.77 (m, 1H, 1H'), 4.72 (s, 1H, 1H'), 4.58 (m, 2H, 2H'), 4.04–3.85 (m, 4H, 4H'), 2.37 (m, 2H, 2H'), 1.81 (m, 2H, 2H'), 1.71 (m, 2H, 2H'), 1.52 (m, 2H, 2H'); $^{13}$C -NMR (400 MHz, CDCl$_3$) δ=173.4, 173.4, 160.5, 160.4, 152.0, 151.8, 150.8, 150.7, 132.8, 132.6, 132.3, 132.3, 132.1, 132.1, 128.2 (2C), 128.0 (2C), 127.5, 127.5, 118.3, 118.3, 114.8, 114.8, 114.6 (2C), 114.6 (2C), 108.0, 104.9, 93.5, 91.6, 86.4, 86.4, 84.3, 83.8, 83.3, 80.5, 67.9, 67.8, 65.1, 65.1, 63.2, 62.9, 34.2, 34.2, 28.9, 28.9, 25.7, 25.7, 24.7, 24.7; IR (film) ν=3233, 3109, 3073, 2934, 1727, 1595, 1396, 1245, 1194, 1167, 1101, 1073, 984, 832; HRMS (MALDI-FTMS) m/z 567.1627(567.1617 calculated for C$_{26}$H$_{29}$N$_4$O$_7$ClNa (M+Na)+).

2.3 6-{4-(4-(6-Chloro-purin-9-yl)-6-hydroxymethyl-tetrahydro-furo(3,4-d)(1,3)dioxol-2-yl)-phenoxy}-hexanoic acid 6

A mixture of 5 (59.31 g, 108.8 mmol), tetrakis (triphenylphosphine)palladium (Pd(PPh$_3$)$_4$, 12.6 g, 10.9 mmol), and dimedone (45.7 g, 326.4 mmol) in dry DCM (600 mL) was stirred in a nitrogen atmosphere for 3.5 h at room temperature. 500 ml of the solvent was removed in vacuo and the remaining volume was loaded on a silica plug. After the dimedone byproducts were removed by washing the plug with MeOH/DCM 1:100, the product was eluted with MeOH/DCM 1:10. The fraction containing the product was concentrated in vacuo to afford 6 as a white powder (46.6 g, 92.3 mmol, 85%) as a mixture of two diastereomers: M.p.: 127–129° C.; $^1$H-NMR (400 MHz, CDCl$_3$) δ=11.50 (s, 1H, 1H'), 8.79 (s, 1H), 8.78 (s, 1H'), 8.42 (s, 1H), 8.34 (s, 1H'), 7.47 (d, J=8.6, 2H), 7.37 (d, J=8.6, 2H'), 6.95 (d, J=8.5, 2H), 6.90 (d, J=8.5, 2H'), 6.24 (s, 1H), 6.19 (m, 1H, 1H'), 6.02 (s, 1H'), 5.37–5.19 (m, 2H, 2H'), 4.73 (s, 1H, 1H'), 4.57 (m, 1H, 1H'), 4.04–3.86 (m, 4H, 4H'), 2.40 (m, 2H, 2H'), 1.82 (m, 2H, 2H'), 1.72 (m, 2H, 2H'), 1.55 (m, 2H, 2H'); $^{13}$C-NMR (400 MHz, CDCl$_3$) δ=178.8, 178.8, 160.6, 160.5, 152.3, 152.2, 150.6, 150.6, 133.4, 133.3, 132.2, 132.2, 128.3 (2C),128.1, 128.0 (2C), 127.6, 114.9, 114.9, 114.8 (2C), 114.7 (2C), 108.1, 105.1, 94.0, 92.0, 86.4, 86.3, 84.2, 83.5, 83.5, 80.5, 68.0, 67.9, 63.3, 63.0, 34.0, 34.0, 29.0, 29.0, 25.8, 25.8, 24.6, 24.6; IR (film) ν=3292, 3109, 3074, 2938, 1708, 1595, 1392, 1245, 1225, 1194, 1108, 1069, 828; HRMS (MALDI-FTMS) m/z 527.1285 (527.1304 calculated for C$_{23}$H$_{25}$N$_4$O$_7$ClNa (M+Na)+).

2.4 Resin Bound 5'-hydroxy-6-chloro-purine Scaffold 8

A mixture of 6 (56.8 g, 113 mmol), N-((Dimethylamino)-1H-1,2,3-triazolo(4,5-b)pyridin-1-ylmethylene)-N-methylmethanaminium hexafluorophosphate N-oxide (HATU, 42.8 g, 113 mmol), diisopropyl ethyl amine (19.6 mL, 113 mmol) in DMF (500 mL) was added to aminomethyl resin (7, 50.0 g, 75 mmol) and agitated for 1 h at room temperature. The complete conversion was confirmed by a negative bromophenol blue test. The resin was then washed with DMF (4×500 mL), THF (4×500 mL), DCM (4×500 mL) and MeOH (4×500 mL), and subsequently dried in vacuo. IR (on bead) ν=3056w, 3025w, 2920m, 2849w, 1652m, 1610w, 1590m, 1562m, 1515m, 1488m, 1453m, 1437m, 1395m, 1336m, 1302w, 1246s, 1200s, 1171m, 1079s, 1020m, 700s.

2.5 Resin Bound 5'-azido-6-chloro-purine Scaffold 9

Diethylazodicarboxylate (DEAD, 59 mL, 375 mmol) was slowly added to a stirred solution of triphenyl phosphine (PPh$_3$, 98.3 g, 375 mmol) in anhydrous THF (400 mL). The mixture was kept at room temp via water bath. Diphenyl phosphoryl azide (DPPA, 80.75 mL, 375 mmol) was added and the solution was then transferred to a solid phase peptide synthesis reactor containing resin 8 (86.5 g, 75 mmol). The mixture was allowed to react for 10 h at room temperature using N$_2$ agitation. The resin was subsequently washed with THF (4×400 mL), DMF (4×400 mL), DCM (4×400 mL) and MeOH (4×400 mL) and dried in vacuo. IR (on bead) v=3056w, 3021w, 2970w, 2924m, 2861w, 2104m, 1750w, 1652m, 1610w, 1594m, 1562m, 1515m, 1488m, 1449m, 1437m, 1396w, 1336w, 1246s, 1196m, 1171m, 1063s, 1028m, 700s.

2.6 General Procedure for the Formation of Nucleophilic Aromatic Reactions to Form 10 and 11

The sorted nanokan microreactors containing resins 8 and 9 were placed into amber Quoparc bottles on J-Kem BTS 3000 benchtop shakers equipped with heated reaction blocks. The nanokans were then subjected to the proper conditions for different nucleophiles as described in FIG. 5. For example, using primary and secondary amines as nucleophiles, the conditions are 24 h agitation at 50° C. with 0.4 M amine in NMP. After the analysis of control nanokans showed a complete conversion, the microreactors were washed with NMP (4×), 1,4-dioxane (4×) and alternating DCM and MeCN (4×). The microreactors were subsequently dried in vacuo.

3. Synthesis of FIG. 6 Compounds

3.1 General Procedure for the Formation of Nucleophilic Aromatic Reactions to Form 5–8

The sorted nanokan microreactors containing resins 1, 2, 3, and 4 were placed into amber Quoparc bottles on J-Kem BTS 3000 benchtop shakers equipped with heated reaction blocks. The nanokans were then subjected to the proper conditions for different nucleophiles as described in FIG. 6. For example, using primary and secondary amines as nucleophiles, the conditions are 24 h agitation at 50° C. with 0.4 M amine in NMP. After the analysis of control nanokans showed a complete conversion, the microreactors were washed with NMP (4×), 1,4-dioxane (4×) and alternating DCM and MeCN (4×). The microreactors were subsequently dried in vacuo.

4. Synthesis of FIG. 7 Compounds

4.1 General Procedure for the Formation of 5'-triazole Scaffolds 3–6

Figure 7:
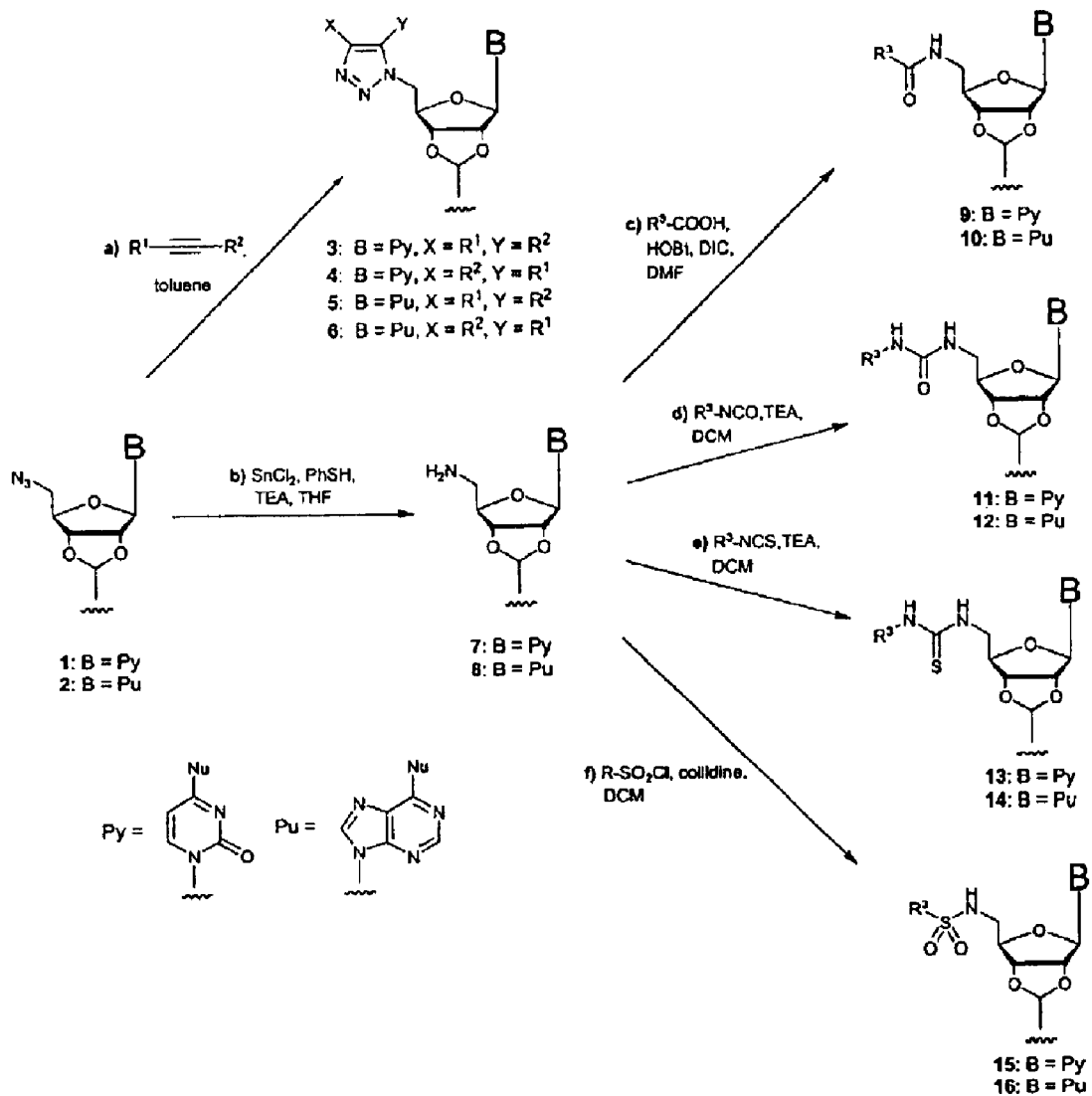
FIG. 7 is an exemplary chemical scheme for the synthesis of solid phase purine and pyrimidine nucleoside analogs.

The nanokan microreactors containing 5'-azido scaffolds of the general structures 1 and 2 were agitated in a 20% v/v solution of validated acetylene in toluene using the conditions described in FIG. 7. The nanokans were then washed with NMP (4×), 1,4-dioxane (4×) and alternating DCM and MeCN (4×) and subsequently dried in vacuo.

4.2 General Procedure for the Formation of 5'-amino Scaffolds 7 and 8

A solution of stannous chloride (SnCl$_2$, 142 g, 0.75 mol) and thiophenol (PhSH, 308 mL, 3 mol) in THF (5 L) was prepared and cooled to 0° C. Triethylamine (TEA, 523 ml, 3.75 mol) was added and the resulting precipitate was filtered off. The remaining solution was then added to the nanokan microreactors containing 5'-azido scaffolds of the general structures 1 and 2 and agitated for 2.5 h at room temperature. The nanokans were then washed with THF (4×), DMF (4×), DCM (4×) and MeOH (4×) and subsequently dried in vacuo.

4.3 General Procedure for the Formation of 5'-aminoacyl Scaffolds 9 and 10

The nanokan microreactors containing 5'-amino scaffolds of the general structure 7 and 8 were agitated in a 0.4 M solution of carboxylic acid, N-hydroxybenzotriazole (HOBt) and diisopropylcarbodiimide (DIC) in DMF for 24 h at room temperature. The nanokans were then washed with DMF (4×), 1,4-dioxane (4×) and alternating DCM and MeOH (4×) and subsequently dried in vacuo.

4.4 General Procedure for the Formation of 5'-urea Scaffolds 11 and 12

The nanokan microreactors containing 5'-amino scaffolds of the general structure 7 and 8 were agitated in a solution containing 0.4 M of isocyanate and 0.6 M triethylamine (TEA) in DCM for 24 h at room temperature. The nanokans were then washed with DMF (4×), 1,4-dioxane (4×) and alternating DCM and MeOH (4×) and subsequently dried in vacuo.

4.5 General Procedure for the Formation of 5'-thiourea Scaffolds 13 and 14

The nanokan microreactors containing 5'-amino scaffolds of the general structure 7 and 8 were agitated in a solution containing 0.4 M of thioisocyanate and 0.6 M triethylamine (TEA) in DCM for 24 h at room temperature. The nanokans were then washed with DMF (4×), 1,4-dioxane (4×) and alternating DCM and MeOH (4×) and subsequently dried in vacuo.

4.6 General Procedure for the Formation of 5'-aryl sulfonamido Scaffolds 15 and 16

The nanokan microreactors containing 5'-amino scaffolds of the general structure 7 and 8 were agitated in a solution containing 0.4 M of aryl sulfonyl chloride and 0.6 M collidine in DCM for 32 h at room temperature. The nanokans were then washed with DMF (4×), 1,4-dioxane (4×) and alternating DCM and MeOH (4×) and subsequently dried in vacuo.

5. Synthesis of FIG. 8 Compounds

5.1 General Procedure for the Formation of 5'-triphenylphosphinamino Scaffolds 3 and 4

The nanokan microreactors containing 5'-azido scaffolds of the general structure 1 and 2 were agitated in a 0.4 M solution of triphenylphosphine (PPh$_3$) in dry THF for 6 h at room temperature. The nanokans were evacuated in 2 h intervals to allow evolving N$_2$ to leave the microreactor. The nanokans were then washed with dry THF (3×) and subsequently dried in vacuo.

5.2 General Procedure for the Formation of 5'-carbodiimide Scaffolds 5 and 6

The nanokan microreactors containing 5'-triphenylphosphinamino scaffolds of the general structure 3 and 4 were agitated in a 0.4 M solution of isocyanate in dry THF for 90 min at room temperature. The solution was removed and the nanokans were subjected to the next reaction step without any washing or drying procedure.

5.3 General Procedure for the Formation of 5'-iminochloride Scaffolds 7 and 8

The nanokan microreactors containing 5'-triphenylphosphinamino scaffolds of the general structure 3 and 4 were agitated in a solution containing 0.4 M of carboxylic acid chloride and 0.3 M triethylamine (TEA) in dry THF for 90 min at 50° C. The solution was removed and the nanokans were subjected to the next reaction step without any washing or drying procedure.

5.4 General Procedure for the Formation of 5'-guanidino and 5'-amidino Scaffolds 9–12

The nanokan microreactors containing 5'-carbodiimide and 5'-iminochloride scaffolds of the general structure 5–8 were agitated in a 0.6 M solution of amine in dry THF for 24 h at room temperature. The solution was removed and the nanokans were subjected to the next reaction step without any washing or drying procedure. The nanokans were then washed with DMF (4×), 1,4-dioxane (4×) and alternating DCM and MeOH (4×) and subsequently dried in vacuo.

6. Synthesis of FIG. 9 Compounds

6.1 General Procedure for the Deprotection of 5'-acetoxy Resins 1 to the 5'-hydroxy Resins 2

The nanokan microreactors containing 5'-acetoxy scaffolds 1 were agitated in a 0.4 M solution of hydrazine ($H_2NNH_2$) in THF for 48 h at room temperature. The nanokans were then washed with THF (2×), NMP (4×) and THF (4×) and dried in vacuo.

6.2 General Procedure for the Formation of 5'-mesyl Scaffolds 4 and 5

The nanokan microreactors containing 5'-hydroxy scaffolds 2 and 3 were agitated in a 0.4 M solution of mesyl chloride (MsCl) in pyridine for 5 h at room temperature. The nanokans were then washed with DMF (4×), 1,4-dioxane (4×) and alternating DCM and MeCN (4×) and subsequently dried in vacuo.

6.3 General Procedure for the Formation of 5'-chloro Scaffolds 8 and 9

The nanokan microreactors containing 5'-hydroxy scaffolds 2 and 3 were agitated in a solution containing 0.4 M triphenylphosphine ($PPh_3$) and 0.4 M carbon tetrachloride ($CCl_4$) in DCM for 5 h at room temperature. The nanokans were then washed with DMF (4×), 1,4-dioxane (4×) and alternating DCM and MeCN (4×) and subsequently dried in vacuo.

6.4 General Procedure for the Formation of 5'-aldehyde Scaffolds 10 and 11

The nanokan microreactors containing 5'-hydroxy scaffolds 2 and 3 were agitated in a 0.2 M solution of Dess-Martin periodinane in DCM for 12 h at room temperature. The nanokans were then washed with DMF (4×), 1,4-dioxane (4×) and alternating DCM and MeCN (4×) and subsequently dried in vacuo.

6.5 General Procedure for the Formation of Substituted 5'-amino pyrimidine Scaffolds 6

The nanokan microreactors containing 5'-mesyl scaffolds 4 were agitated in a 0.4 M solution of amine in NMP for 24 h at room temperature. The nanokans were then washed with DMF (4×), 1,4-dioxane (4×) and alternating DCM and MeCN (4×) and subsequently dried in vacuo.

6.6 General Procedure for the Formation of Substituted 5'-amino purine Scaffolds 7

The nanokan microreactors containing 5'-chloro scaffolds 9 were agitated in a 0.4 M solution of amine in NMP for 24 h at 75° C. The nanokans were then washed with DMF (4×), 1,4-dioxane (4×) and alternating DCM and MeCN (4×) and subsequently dried in vacuo.

7. Synthesis of FIG. 10 Compounds

7.1 General Procedure for the Formation of 5'-carboxy Scaffolds 3 and 4

The nanokan microreactors containing 5'-hydroxy scaffolds 1 and 2 were agitated in a suspension containing 0.2 M bisacetoxy-iodobenzene (BAIB), 0.2 M bicarbonate ($NaHCO_3$) and 0.01 M 2,2,6,6-tetramethyl-piperidinyloxyl (TEMPO) in MeCN/$H_2O$ 1:1 for 5 h at room temperature. The nanokans were then washed with 1:1 MeCN/$H_2O$ 1:1 (2×), $H_2O$ (2×), DMF (4×), 1,4-dioxane (4×) and MeCN (4×) and subsequently dried in vacuo.

7.2 General Procedure for the Formation of 5'-carboxamido Scaffolds 5 and 6

A solution of 0.4 M N-hydroxybenzotriazole (HOBt) and 0.4 M diisopropylcarbodiimide (DIC) in DMF was added to the nanokan microreactors containing 5'-carboxy scaffolds 3 and 4 and agitated for 10 min at room temperature. The appropriate amount of amine (0.4 M) was added and the nanokans were agitated for 24 h at room temperature. The nanokans were then washed with DMF (4×), 1,4-dioxane (4×) and alternating DCM and MeCN (4×) and subsequently dried in vacuo.

8. Synthesis of FIG. 11 Compounds

8.1 General Procedure for the Formation of Substituted 5'-carbonylimidazolo Scaffolds 3 and 4

The nanokan microreactors containing 5'-hydroxy scaffolds 1 and 2 were agitated in a 0.4 M solution of carbonyldiimidazole (CDI) in dry THF for 5 h at room temperature. The nanokans were then washed with dry THF (4×) and subsequently dried in vacuo.

8.2 General Procedure for the Formation of 5'-carbamate Scaffolds 5 and 6

The nanokan microreactors containing 5'-carbonylimidazolo scaffolds 3 and 4 were agitated in a 0.4 M solution of amine in NMP for 24 h at 50° C. (primary amines) or 48 h at 75° C. (secondary amines). The nanokans were then washed with DMF (4×), 1,4-dioxane (4×) and alternating DCM and MeCN (4×) and subsequently dried in vacuo.

8.2 General Procedure for the Formation of 5'-carbonate Scaffolds 7 and 8

The nanokan microreactors containing 5'-carbonylimidazolo scaffolds 3 and 4 were agitated in a 2 M solution of alcohol in NMP for 48 h at 75° C. The nanokans were then washed with DMF (4×), 1,4-dioxane (4×) and alternating DCM and MeCN (4×) and subsequently dried in vacuo.

9. Synthesis of FIG. 12 Compounds

9.1 General Procedure for the Cleavage of the Nucleoside Analogs 1 and 2 off the Solid Support to Form Nucleoside Analogs 3 and 4

The Nanokan microreactors were sorted into IRORI 96'-well cleavage blocks with attached deep well collection plates. 250 µL of a solution of 5% trifluoroacetic acid (TFA), 5% $H_2O$ in 1,4-dioxane (cleavage cocktail) was added to the top plates containing the nanokans, and the plates were subsequently evacuated for 1 min. Another 100 µL aliquot was added to each well and the cleavage blocks were incubated at 50° C. for 6 h. The cleavage solution containing

What is claimed is:

1. A compound having the formula:

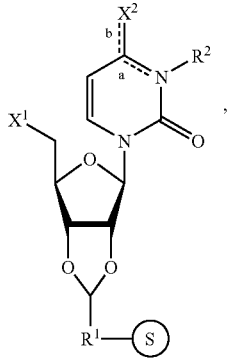

I wherein:
- $X^1$ is an optionally substituted azidyl or hydroxyl;
- $X^2$ is an optionally substituted triazolyl, or together with a double bond attached to the ring form a carbonyl;
- $R^1$ is a linker moiety;
- $R^2$ is hydrogen, an optionally substituted alkyl, an optionally substituted heteroalkyl, an optionally substituted aryl, an optionally substituted heteroaryl, an optionally substituted heterocycloalkyl, or is absent;
- the dashed bonds denoted by a and b are single or double bonds wherein a is a single bond when b is a double bond and a is a double bond when b is a single bond; and
- S is a solid phase.

2. The compound of claim 1, wherein $X^1$ is azidyl, $X^2$ is triazolyl, $R^2$ is absent, and the dashed bond a is a double bond and the dashed bond b is a single bond.

3. The compound of claim 1, wherein $X^1$ is azidyl, the dashed bond b is a double bond together with $X^2$ form a carbonyl, $R^2$ is hydrogen, and the dashed bond a is a single bond.

4. The compound of claim 1, wherein $X^1$ is hydroxyl, $X^2$ is triazolyl, $R^2$ is absent, and the dashed bond a is a double bond and the dashed bond b is a single bond.

5. The compound of claim 1, wherein $R^1$ is wherein l and m are integers each independently selected from about 1 to about 50.

6. The compound of claim 1, wherein S is an optionally substituted macroreticular polystyrene based resin.

7. The compound having the formula:

II wherein:
- $X^1$ is an optionally substituted azidyl or hydroxyl;
- $X^2$ is chloro, or together with a double bond attached to the ring form a carbonyl;
- $R^1$ is a linker moiety;
- $R^2$ is selected from hydrogen, an optionally substituted alkyl, an optionally substituted heteroalkyl, an optionally substituted aryl, an optionally substituted heteroaryl, an optionally substituted heterocycloalkyl, or is absent;
- the dashed bonds denoted by a and b are single or double bonds wherein a is a single bond when b is a double bond and a is a double bond when b is a single bond; and
- S is a solid phase.

8. The compound of claim 7, wherein $X^1$ is azidyl, $X^2$ is chloro, $R^2$ is absent, and the dashed bond a is a double bond and the dashed bond b is a single bond.

9. The compound of claim 7, wherein $X^1$ is azidyl, the dashed bond b is a double bond together with $X^2$ form a carbonyl, $R^2$ is hydrogen, and the dashed bond a is a single bond.

10. The compound of claim 7, wherein $X^1$ is hydroxyl, $X^2$ is chloro, $R^2$ is absent, the dashed bond a is a double bond and the dashed bond b is a single bond.

11. The compound of claim 7, wherein $R^1$ is wherein l and m are integers independently selected from about 1 to about 50.

12. The compound of claim 7, wherein S is an optionally substituted macroreticular polystyrene based resin.

13. A library of at least 500 compounds having the formula:

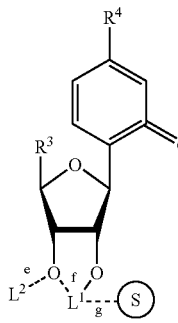

III wherein:

R³ is —SR⁵, —NR⁶R⁷, —NR⁸—NR⁹R¹⁰, —NR¹¹—OR¹² or —OR¹³, wherein R⁵, R⁶, R⁷, R⁸, R⁹, R¹⁰, R¹¹, R¹² and R¹³ are each members independently selected from hydrogen, an optionally substituted alkyl, an optionally substituted heteroalkyl, an optionally substituted aryl, an optionally substituted heteroaryl, and an optionally substituted heterocycloalkyl;

R⁴ is —CH₂—OH, —CH₂—NR¹⁴R¹⁵, —CH₂—Cl, —CH₂—N₃, —CH₂—COOH,

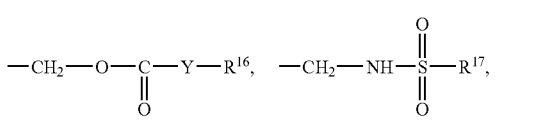

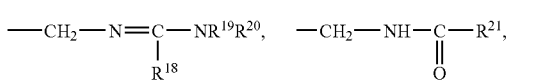

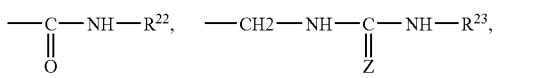

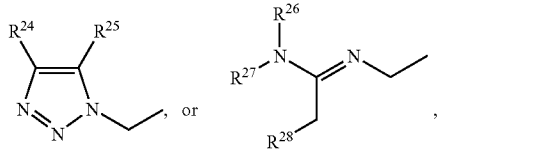

wherein R¹⁴, R¹⁵, R¹⁶, R¹⁷, R¹⁸, R¹⁹, R²⁰, R²¹, R²², R²³, R²⁴, R²⁵, R²⁶, R²⁷, and R²⁸ are each members independently selected from hydrogen, an optionally substituted alkyl, an optionally substituted heteroalkyl, an optionally substituted aryl, an optionally substituted heteroaryl, and an optionally substituted heterocycloalkyl;

Z is an oxygen or sulfur;

Y is an oxygen or a secondary amine;

the dashed bonds denoted by e, f and g are single bonds or absent wherein if e is a single bond then f is absent and g is absent, and if e is absent then f is a single bond and g is a single bond;

L¹ is a linker moiety or hydrogen wherein L¹ is hydrogen when e is a single bond and L¹ is a linker moiety when e is absent;

L² is hydrogen or absent wherein L² is hydrogen when e is a single bond and L² is absent when e absent; and S is an optionally present solid phase.

14. A library of at least 500 compounds having the formula:

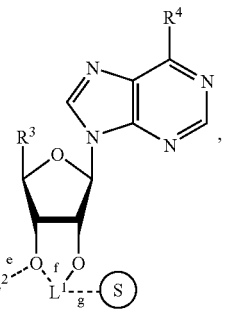

IV wherein:

R³ is —SR⁵, —NR⁶R⁷, —NR⁸—NR⁹R¹⁰, —NR¹¹—OR¹² or —OR¹³, wherein R⁵, R⁶, R⁷, R⁸, R⁹, R¹⁰, R¹¹, R¹² and R¹³ are each members independently selected from hydrogen, an optionally substituted alkyl, an optionally substituted heteroalkyl, an optionally substituted aryl, an optionally substituted heteroaryl, and an optionally substituted heterocycloalkyl;

R⁴ is —CH₂—OH, —CH₂—NR¹⁴R¹⁵, —CH₂—Cl, —CH₂—N₃, —CH₂—COOH,

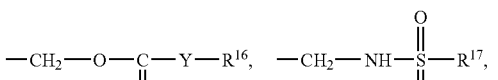

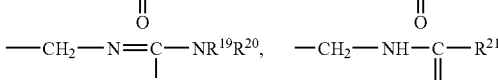

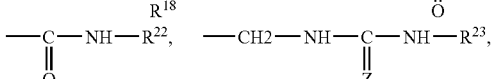

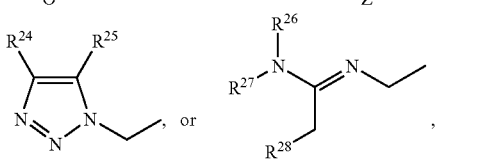

wherein R¹⁴, R¹⁵, R¹⁶, R¹⁷, R¹⁸, R¹⁹, R²⁰, R²¹, R²², R²³, R²⁴, R²⁵, R²⁶, R²⁷, and R²⁸ are each members independently selected from hydrogen, an optionally substituted alkyl, an optionally substituted heteroalkyl, an optionally substituted aryl, an optionally substituted heteroaryl, and an optionally substituted heterocycloalkyl;

Z is an oxygen or sulfur;

Y is an oxygen or a secondary amine;

the dashed bonds denoted by e, f and g are single bonds or absent wherein if e is a single bond then f is absent and g is absent, and if e is absent then f is a single bond and g is a single bond;

L¹ is a linker moiety or hydrogen wherein L¹ is hydrogen when e is a single bond and L¹ is a linker moiety when e is absent;

L² is hydrogen or absent wherein L² is hydrogen when e is a single bond and L² is absent when e absent; and S is an optionally present solid phase.

15. A method for the preparation of a combinatorial chemistry library of compounds having the formula:

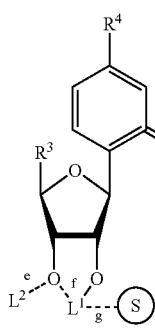
III wherein:
R$^3$ is —SR$^5$, —NR$^6$R$^7$, —NR$^8$—NR$^9$R$^{10}$, —NR$^{11}$—OR$^{12}$ or —OR$^{13}$,
  wherein R$^4$, R$^5$, R$^6$, R$^7$, R$^8$, R$^9$, R$^{10}$, R$^{11}$, R$^{12}$ and R$^{13}$ are each member independently selected from hydrogen, an optionally substituted alkyl, an optionally substituted heteroalkyl, an optionally substituted aryl, an optionally substituted heteroaryl, and an optionally substituted heterocycloalkyl;
R$^4$ is —CH$_2$—OH, —CH$_2$—NR$^{14}$R$^{15}$, —CH$_2$—Cl, —CH$_2$—N$_3$, —CH$_2$—COOH,

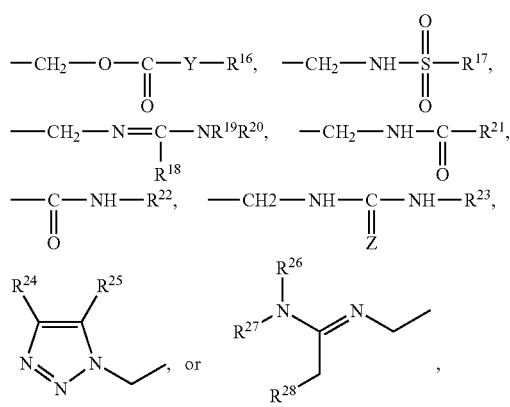

wherein R$^{14}$, R$^{15}$, R$^{16}$, R$^{17}$, R$^{18}$, R$^{19}$, R$^{20}$, R$^{21}$, R$^{22}$, R$^{23}$, R$^{24}$, R$^{25}$, and R$^{26}$, are each members independently selected from hydrogen, an optionally substituted alkyl, an optionally substituted heteroalkyl, an optionally substituted aryl, an optionally substituted heteroaryl, and an optionally substituted heterocycloalkyl;
Z is an oxygen or sulfur;
Y is an oxygen or a secondary amine;
the dashed bonds denoted by e, f and g are single bonds or absent wherein if e is a single bond then f is absent and g is absent, and if e is absent then f is a single bond and g is a single bond;
L$^1$ is a linker moiety or hydrogen wherein L$^1$ is hydrogen when e is a single bond and L$^1$ is a linker moiety when e is absent;
L$^2$ is hydrogen or absent wherein L$^2$ is hydrogen when e is a single bond and L$^2$ is absent when e absent; and
S is an optionally present solid phase;
the method comprising subjecting a combinatorial chemistry intermediate to at least one diversity generating reaction to form the combinatorial chemistry library of compounds, the combinatorial chemistry intermediate having the formula:

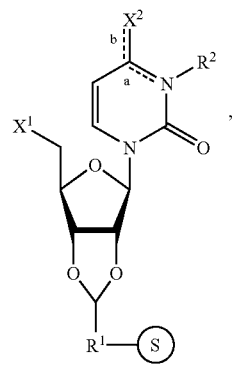
I wherein:
X$^1$ is an optionally substituted azidyl or hydroxyl;
X$^2$ is an optionally substituted triazolyl, or together with a double bond attached to the ring form a carbonyl;
R$^1$ is a linker moiety;
R$^2$ is hydrogen, an optionally substituted alkyl, an optionally substituted heteroalkyl, an optionally substituted aryl, an optionally substituted heteroaryl, an optionally substituted heterocycloalkyl, or is absent;
the dashed bonds denoted by a and b are single or double bonds wherein a is a single bond when b is a double bond and a is a double bond when b is a single bond; and
S is a solid phase.

16. A method for the preparation of a combinatorial chemistry library of compounds having the formula:

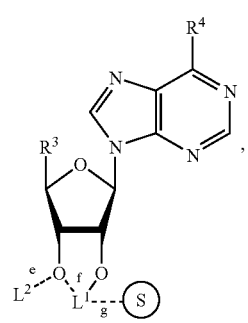
IV wherein:
R$^3$ is —SR$^5$, —NR$^6$R$^7$, —NR$^8$—NR$^9$R$^{10}$, —NR$^{11}$—OR$^{12}$ or —OR$^{13}$,
  wherein R$^5$, R$^6$, R$^7$, R$^8$, R$^9$, R$^{10}$, R$^{11}$, R$^{12}$ and R$^{13}$ are each members independently selected from hydrogen, an optionally substituted alkyl, an optionally substituted heteroalkyl, an optionally substituted aryl, an optionally substituted heteroaryl, and an optionally substituted heterocycloalkyl;
R$^4$ is —CH$_2$—OH, —CH$_2$—NR$^{14}$R$^{15}$, —CH$_2$—Cl, —CH$_2$—N$_3$, —CH$_2$—COOH,

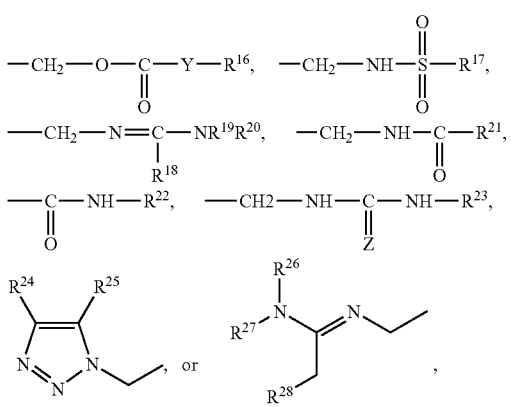

wherein $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, and $R^{28}$ are each members independently selected from hydrogen, an optionally substituted alkyl, an optionally substituted heteroalkyl, an optionally substituted aryl, an optionally substituted heteroaryl, and an optionally substituted heterocycloalkyl;

Z is an oxygen or sulfur;

Y is an oxygen or a secondary amine;

the dashed bonds denoted by e, f and g are single bonds or absent wherein if e is a single bond then f is absent and g is absent, and if e is absent then f is a single bond and g is a single bond;

$L^1$ is a linker moiety or hydrogen wherein $L^1$ is hydrogen when e is a single bond and $L^1$ is a linker moiety when e is absent;

$L^2$ is hydrogen or absent wherein $L^2$ is hydrogen when e is a single bond and $L^2$ is absent when e absent; and S is an optionally present solid phase;

the method comprising subjecting a combinatorial chemistry intermediate to at least one diversity generating reaction to form the combinatorial chemistry library of compounds, the combinatorial chemistry intermediate having the formula:

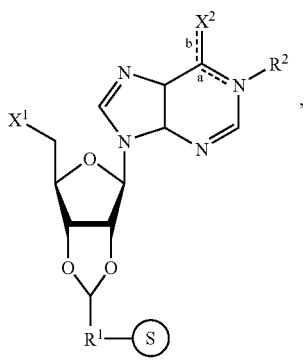

II wherein:

$X^1$ is an optionally substituted azidyl or hydroxyl;

$X^2$ is an optionally substituted triazolyl, or together with a double bond attached to the ring form a carbonyl;

$R^1$ is a linker moiety;

$R^2$ is hydrogen, an optionally substituted alkyl, an optionally substituted heteroalkyl, an optionally substituted aryl, an optionally substituted heteroaryl, an optionally substituted heterocycloalkyl, or is absent;

the dashed bonds denoted by a and b are single or double bonds wherein a is a single bond when b is a double bond and a is a double bond when b is a single bond; and S is a solid phase.

17. A method of screening a library of compounds for an agonist of a purine receptor, the method comprising:

(i) preparing a library of compounds having the formula:

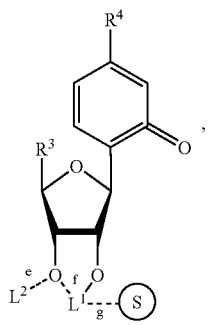

III wherein:

$R^3$ is $-SR^5$, $-NR^6R^7$, $-NR^8-NR^9R^{10}$, $-NR^{11}-OR^{12}$ or $-OR^{13}$, wherein $R^5$, $R^6$, $R^7$, $R^8$, $R^9$, $R^{10}$, $R^{11}$, $R^{12}$ and $R^{13}$ are each members independently selected from hydrogen, an optionally substituted alkyl, an optionally substituted heteroalkyl, an optionally substituted aryl, an optionally substituted heteroaryl, and an optionally substituted heterocycloalkyl;

$R^4$ is $-CH_2-OH$, $-CH_2-NR^{14}R^{15}$, $-CH_2-Cl$, $-CH_2-N_3$, $-CH_2-COOH$,

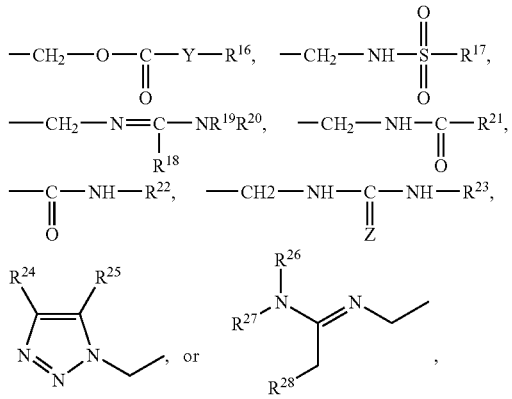

wherein $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, and $R^{28}$ are each members independently selected from hydrogen, an optionally substituted alkyl, an optionally substituted heteroalkyl, an optionally substituted aryl, an optionally substituted heteroaryl, and an optionally substituted heterocycloalkyl;

Z is an oxygen or sulfur;

Y is an oxygen or a secondary amine;

the dashed bonds denoted by e, f and g are single bonds or absent wherein if e is a single bond then f is absent and g is absent, and if e is absent then f is a single bond and g is a single bond;

$L^1$ is a linker moiety or hydrogen wherein $L^1$ is hydrogen when e is a single bond and $L^1$ is a linker moiety when e is absent;

$L^2$ is hydrogen or absent wherein $L^2$ is hydrogen when e is a single bond and $L^2$ is absent when e absent; and S is an optionally present solid phase; and (ii) screening the library by contacting the purine receptor with the library.

18. A method of screening a library of compounds for an agonist of a purine receptor, the comprising:

(i) preparing a library of compounds having the formula:

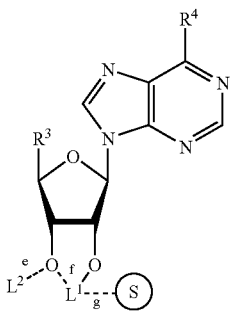

IV wherein:

$R^3$ is —$SR^5$, —$NR^6R^7$, —$NR^8$—$NR^9R^{10}$, —$NR^{11}$—$OR^{12}$ or —$OR^{13}$, wherein $R^5$, $R^6$, $R^7$, $R^8$, $R^9$, $R^{10}$, $R^{11}$, $R^{12}$ and $R^{13}$ are each members independently selected from hydrogen, an optionally substituted alkyl, an optionally substituted heteroalkyl, an optionally substituted aryl, an optionally substituted heteroaryl, and an optionally substituted heterocycloalkyl;

$R^4$ is —$CH_2$—OH, —$CH_2$—$NR^{14}R^{15}$, —$CH_2$—Cl, —$CH_2$—$N_3$, —$CH_2$—COOH,

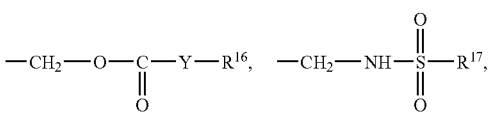

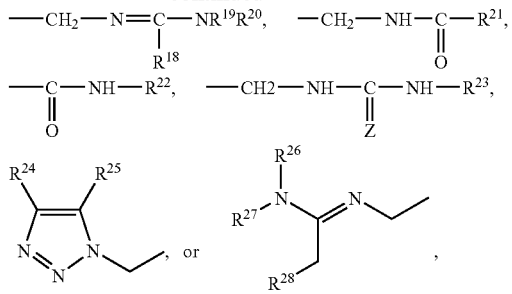

wherein $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, and $R^{28}$ are each members independently selected from hydrogen, an optionally substituted alkyl, an optionally substituted heteroalkyl, an optionally substituted aryl, an optionally substituted heteroaryl, and an optionally substituted heterocycloalkyl;

Z is an oxygen or sulfur;

Y is an oxygen or a secondary amine;

the dashed bonds denoted by e, f and g are single bonds or absent wherein if e is a single bond then f is absent and g is absent, and if e is absent then f is a single bond and g is a single bond;

$L^1$ is a linker moiety or hydrogen wherein $L^1$ is hydrogen when e is a single bond and $L^1$ is a linker moiety when e is absent;

$L^2$ is hydrogen or absent wherein L is hydrogen when e is a single bond and $L^2$ is absent when e absent; and S is an optionally present solid phase; and (ii) screening the library by contacting the purine receptor with the library.

* * * * *